United States Patent
Moir et al.

(10) Patent No.: US 8,906,945 B2
(45) Date of Patent: Dec. 9, 2014

(54) INHIBITORS OF BACTERIAL TYPE III SECRETION SYSTEM

(75) Inventors: Donald T. Moir, Concord, MA (US); Daniel Aiello, Worcester, MA (US); Norton P. Peet, North Andover, MA (US); John D. Williams, Worcester, MA (US)

(73) Assignee: Microbiotix, Inc., Worcester, MA (US)

( * ) Notice: Subject to any disclaimer, the term of this patent is extended or adjusted under 35 U.S.C. 154(b) by 115 days.

(21) Appl. No.: 13/263,071

(22) PCT Filed: Apr. 6, 2010

(86) PCT No.: PCT/US2010/030120
§ 371 (c)(1),
(2), (4) Date: Oct. 5, 2011

(87) PCT Pub. No.: WO2010/118046
PCT Pub. Date: Oct. 14, 2010

(65) Prior Publication Data
US 2012/0114633 A1 May 10, 2012

Related U.S. Application Data

(60) Provisional application No. 61/212,021, filed on Apr. 6, 2009, provisional application No. 61/304,305, filed on Feb. 12, 2010, provisional application No. 61/304,978, filed on Feb. 16, 2010.

(51) Int. Cl.

| | |
|---|---|
| *A61K 31/34* | (2006.01) |
| *A61K 31/36* | (2006.01) |
| *A61K 31/38* | (2006.01) |
| *A61K 31/41* | (2006.01) |
| *A61K 31/44* | (2006.01) |
| *A61K 31/415* | (2006.01) |
| *A61K 31/496* | (2006.01) |
| *A61K 31/381* | (2006.01) |
| *A61K 31/5375* | (2006.01) |
| *A61K 31/4245* | (2006.01) |
| *A61K 45/06* | (2006.01) |
| *A61K 31/407* | (2006.01) |
| *A61K 31/216* | (2006.01) |
| *A61K 31/427* | (2006.01) |
| *A61K 31/16* | (2006.01) |
| *A61K 31/4184* | (2006.01) |
| *A61K 31/429* | (2006.01) |
| *A61K 31/167* | (2006.01) |
| *A61K 31/4152* | (2006.01) |

(52) U.S. Cl.
CPC ........... *A61K 31/4245* (2013.01); *A61K 31/496* (2013.01); *A61K 31/381* (2013.01); *A61K 31/5375* (2013.01); *A61K 45/06* (2013.01); *A61K 31/407* (2013.01); *A61K 31/216* (2013.01); *A61K 31/427* (2013.01); *A61K 31/16* (2013.01); *A61K 31/34* (2013.01); *A61K 31/4184* (2013.01); *A61K 31/429* (2013.01); *A61K 31/167* (2013.01); *A61K 31/4152* (2013.01); *A61K 31/36* (2013.01)
USPC ........... 514/357; 514/364; 514/406; 514/438; 514/466; 514/471

(58) Field of Classification Search
USPC ........... 549/438; 548/162; 514/357, 364, 406, 514/438, 466, 471
See application file for complete search history.

(56) References Cited

U.S. PATENT DOCUMENTS

2005/0143373 A1 6/2005 Alanine et al.
2005/0282824 A1 12/2005 Li

FOREIGN PATENT DOCUMENTS

WO    WO 2008/127275 A2    10/2008

OTHER PUBLICATIONS

Aiello et al., "A Novel Stereo-Specific Inhibitor of *P. aeruginosa* Type-Three Secretion", Abstracts of the Interscience conference on Antimicrobial Agents and Chemotherapy, 49: 183 (2009).
Babichev et al., "2-(2'—Benzothiazolylmethyl)- and 2-(2'—Benzimidazolylmethyl) hydroquinones" Chemical Abstracts Service, Database accession No. 1969: 115062 (1984).
Bartha et al., "Preparation of herbicidal aryloxypropionates", Chemical Abstracts Service, Database accession No. 1990:17758 (1990).
Cole et al., "Anti-Infective Innovations: Highlights from the 49th Interscience Conference on Antimicrobial Agents and Chemotherapy", Drugs of the Future 2009 Prous Science ESP, 34(12): 1005-1028 (2009).
Lesyk et al., New 5-substituted thiazolo[3,2-b][1,2,4]triazol-6-ones: Synthesis and anticancer evaluation: European Journal of Medicinal Chemistry, 42: 641-648 (2007).

*Primary Examiner* — Rebecca Anderson
(74) *Attorney, Agent, or Firm* — Yankwich & Associates, P.C.; Leon R. Yankwich; Michael R. Wesolowski

(57) ABSTRACT

Organic compounds showing the ability to inhibit effector toxin secretion or translocation mediated by bacterial type III secretion systems are disclosed. The disclosed type III secretion system inhibitor compounds are useful for combating infections by Gram-negative bacteria such as *Salmonella* spp., *Shigella flexneri*, *Pseudomonas* spp., *Yersinia* spp., enteropathogenic and enteroinvasive *Escherichia coli*, and *Chlamydia* spp. having such type III secretion systems.

7 Claims, 26 Drawing Sheets

| Structure | Compound Identifier | MW | AVG % Inhibition of exoT-lux at 50 μM (Z-score) | AVG % Inhibition of lac-lux at 50 μM (Z-score) | IC$_{50}$ (μM) for Inhibition of ExoS'-βLA Secretion |
|---|---|---|---|---|---|
| 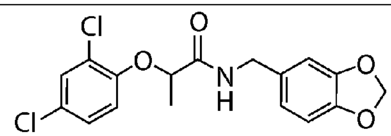 | MBX 1641 | 368 | 95% (15) | 15% (2.9) | 10 |
| 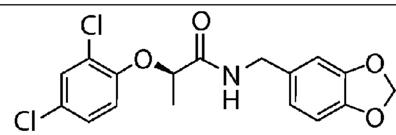 | MBX 1684 | 368 | 98.6% | n.d. | 6 |
| 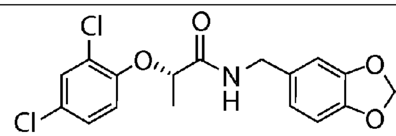 | MBX 1686 | 368 | <3% | n.d. | >100 |
| 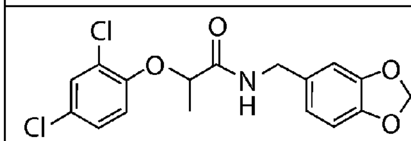 | MBX 1668 | 353 | <3% | n.d. | >100 |
| 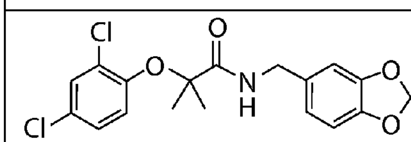 | MBX 1685 | 383 | <3% | n.d. | >100 |
| 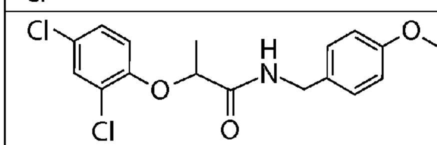 | 6375680 | 354 | 91% (12.8) | 7% (1.6) | 10 |
| 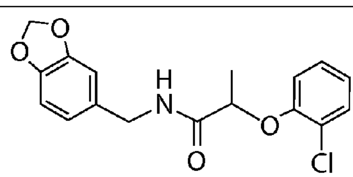 | 9153915 | 334 | 91% (14) | 17% (3) | 23 |

| Structure | Compound Identifier | MW | AVG % Inhibition of exoT-lux at 50 μM (Z-score) | AVG % Inhibition of lac-lux at 50 μM (Z-score) | IC$_{50}$ (μM) for Inhibition of ExoS'-βLA Secretion |
|---|---|---|---|---|---|
| (2,4-dichlorophenoxy)-N-(4-fluorobenzyl)propanamide | 6380194 | 342 | 90% (12.7) | 6% (1.3) | 9 |
| (2,4-dichlorophenoxy)-N-(4-methylbenzyl)propanamide | 6109233 | 338 | 87% (12.2) | 5% (1.1) | 5 |
| (2,4-dichlorophenoxy)-N-(2-methoxybenzyl)propanamide | 6374948 | 354 | 80% (11.2) | 8% (1.7) | 12 |
| (2-chlorophenoxy)-N-(2-fluorobenzyl)propanamide | 9101768 | 308 | 77% (11.8) | 17% (3.1) | |
| (2,4-dichlorophenoxy)-N-(furan-2-ylmethyl)propanamide | 5685325 | 314 | 74% (10.5) | 13% (2.9) | 25 |
| (4-bromo-2-chlorophenoxy)-N-(furan-2-ylmethyl)propanamide | 7945429 | 359 | 73% (10.2) | 7% (1.5) | |
| (2,4-dichlorophenoxy)-N-(2-cyclohexenylethyl)propanamide | 6467504 | 342 | 63% (8.9) | 18% (4.1) | >100 |
| N-(benzo[d][1,3]dioxol-5-ylmethyl)-2-(4-chloro-2-methylphenoxy)propanamide | 6116488 | 348 | 61% (8.6) | 9% (2.2) | 98 |

Fig. 8B

| Structure | Compound Identifier | MW | AVG % Inhibition of exoT-lux at 50 µM (Z-score) | AVG % Inhibition of lac-lux at 50 µM (Z-score) | IC$_{50}$ (µM) for Inhibition of ExoS'-βLA Secretion |
|---|---|---|---|---|---|
| [2,4-dichlorophenoxy propanoyl N-methyl-N-benzylamide] | 6468028 | 338 | 57% (8.1) | -1% (0) | 21 |
| [3,4-dichlorobenzyl amide of 2,4-dichlorophenoxypropanoic acid] | 7271715 | 393 | 31% (4.4) | 12% (2.8) | >100 |
| [2,4-dichlorophenoxy propanoyl N-(4-pyridylmethyl)amide] | 6372013 | 325 | 21% (3) | 6% (1.5) | 59 |
| [thiophen-2-ylmethyl amide of 2-methyl-4-chlorophenoxypropanoic acid] | 7290938 | 310 | 18% (2.6) | 7% (1.8) | |
| [(1,3-dimethylpyrazol-4-yl)methyl amide of 2,4-dichlorophenoxypropanoic acid] | 8804126 | 342 | 17% (2.6) | 15% (2.7) | 61 |
| [4-fluorobenzyl amide of 4-chloro-2-methylphenoxypropanoic acid] | 7306705 | 322 | 16% (2.3) | 19% (4.1) | |

Fig. 8C

| Structure | Compound Identifier | MW | AVG % Inhibition of exoT-lux at 50 μM (Z-score) | AVG % Inhibition of lac-lux at 50 μM (Z-score) | IC$_{50}$ (μM) for Inhibition of ExoS'-βLA Secretion |
|---|---|---|---|---|---|
| 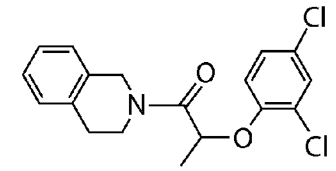 | 7229146 | 350 | 11% (1.5) | 9% (2) | 100 |
| 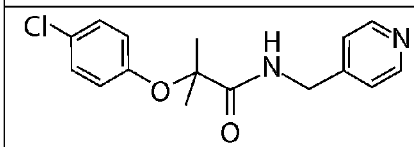 | 7350222 | 305 | 11% (1.5) | 9% (1.8) | |
| 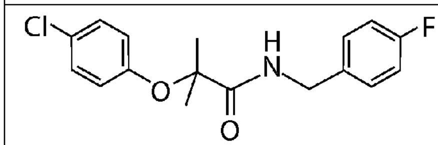 | 7329325 | 322 | 10% (1.4) | 12% (2.6) | |
| 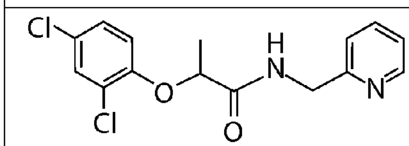 | 6374984 | 325 | 10% (1.4) | 9% (1.9) | 45 |
| 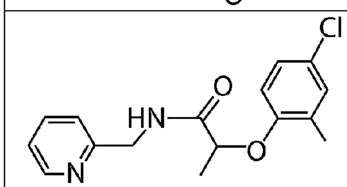 | 7256767 | 305 | 9% (1.3) | 7% (1.3) | |
| 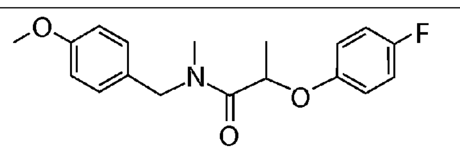 | 9082307 | 317 | 9% (1.4) | 24% (4.3) | |
| 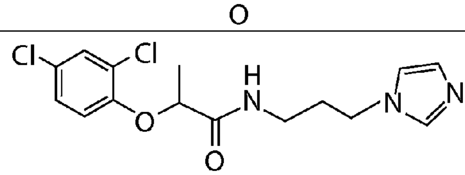 | 6455980 | 342 | 9% (1.3) | 10% (2.4) | |
| 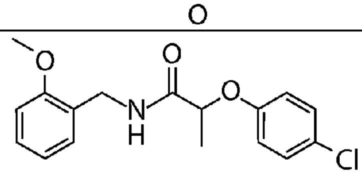 | 9077891 | 320 | 9% (1.4) | 12% (2.2) | |

Fig. 8D

| Structure | Compound Identifier | MW | AVG % Inhibition of exoT-lux at 50 µM (Z-score) | AVG % Inhibition of lac-lux at 50 µM (Z-score) | IC$_{50}$ (µM) for Inhibition of ExoS'-βLA Secretion |
|---|---|---|---|---|---|
| (4-chlorophenoxy-isobutyramide-benzenesulfonamide) | 7408089 | 383 | 9% (1.2) | 10% (2.3) | |
| (4-chlorophenoxy-isobutyramide-furfurylamine) | 7329995 | 294 | 9% (1.2) | 11% (2.2) | |
| (pyridylmethyl-amide-chloro-methylphenoxy) | 7251622 | 305 | 8% (1.1) | 10% (2.5) | |
| (2,4-dichlorophenoxy-propanamide-propyl-morpholine) | 6377124 | 361 | 8% (1.1) | 9% (2.1) | |
| (2-chlorophenoxy-propanamide-furfurylamine) | 9040226 | 280 | 8% (1.2) | 9% (1.7) | |
| (2,4-dichlorophenoxy-propanamide-ethyl-morpholine) | 6735480 | 347 | 6% (0.9) | 9% (2.1) | |
| (benzodioxole-methylamide-naphthyloxy-propanamide) | 9157203 | 349 | 6% (0.9) | 15% (2.7) | |

Fig. 8E

| Structure | Compound Identifier | MW | AVG % Inhibition of exoT-lux at 50 μM (Z-score) | AVG % Inhibition of lac-lux at 50 μM (Z-score) | IC$_{50}$ (μM) for Inhibition of ExoS'-βLA Secretion |
|---|---|---|---|---|---|
| (3-chlorophenethyl amide with 2,4-dichlorophenoxy propanamide) | 7314595 | 373 | 6% (0.8) | 18% (4.1) | >100 |
| (pyridin-2-ylmethyl amide with 3-chlorophenoxy propanamide) | 7301641 | 291 | 5% (0.7) | 11% (2.7) | |
| (benzyl amide with 2,4-difluorophenoxy propanamide) | 9085280 | 291 | 5% (0.8) | 16% (3) | |
| (benzo[d][1,3]dioxol-5-ylmethyl amide with 4-chloro-3,5-dimethylphenoxy propanamide) | 7409826 | 362 | 5% (0.6) | 7% (1.7) | |
| (pyridin-3-ylmethyl amide with 3,5-dimethylphenoxy propanamide) | 7400395 | 284 | 4% (0.7) | 14% (2.4) | |
| (2-methoxybenzyl amide with phenoxy propanamide) | 6184035 | 285 | 4% (0.6) | 10% (2.2) | |
| (pyridin-3-ylmethyl amide with 2,4-dichlorophenoxy propanamide) | 6373847 | 325 | 4% (0.5) | 3% (0.5) | |

Fig. 8F

| Structure | Compound Identifier | MW | AVG % Inhibition of exoT-lux at 50 µM (Z-score) | AVG % Inhibition of lac-lux at 50 µM (Z-score) | IC$_{50}$ (µM) for Inhibition of ExoS'-βLA Secretion |
|---|---|---|---|---|---|
| 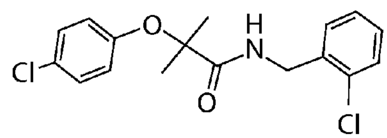 | 7249916 | 338 | 3% (0.4) | 12% (2.6) | |
| 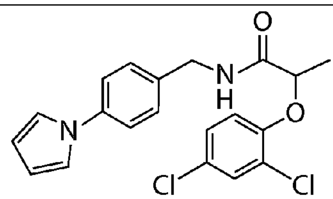 | 8894355 | 389 | 3% (0.5) | 12% (2.2) | |
| 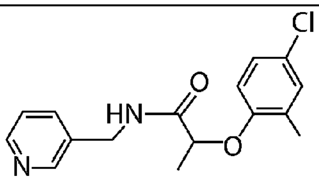 | 5701205 | 305 | 3% (0.4) | 5% (0.9) | |
| 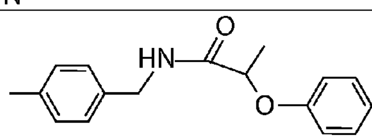 | 6171416 | 269 | 3% (0.4) | 31% (6.7) | |
| 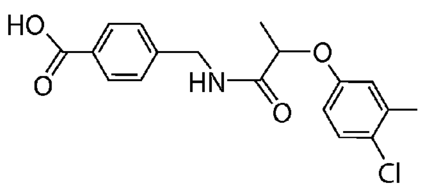 | 8815129 | 348 | 3% (0.4) | 16% (2.8) | |
| 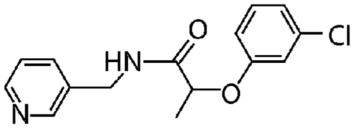 | 7313338 | 291 | 2% (0.3) | 5% (1.3) | |
| 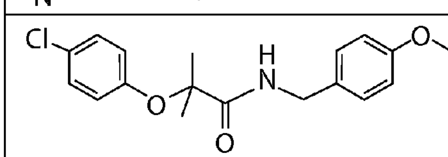 | 7323677 | 334 | 2% (0.2) | 11% (2.6) | |

Fig. 8G

| Structure | Compound Identifier | MW | AVG % Inhibition of exoT-lux at 50 µM (Z-score) | AVG % Inhibition of lac-lux at 50 µM (Z-score) | IC$_{50}$ (µM) for Inhibition of ExoS'-βLA Secretion |
|---|---|---|---|---|---|
| 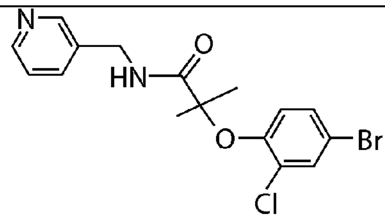 | 9087433 | 384 | 1% (0.1) | 14% (2.5) | |
| 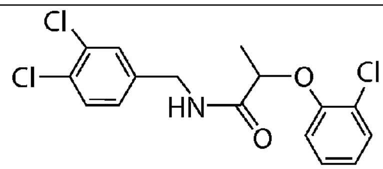 | 8815418 | 359 | 0% (0.1) | 28% (5.1) | |
| 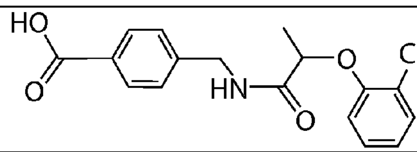 | 8815417 | 334 | 0% (0) | 9% (1.7) | |
| 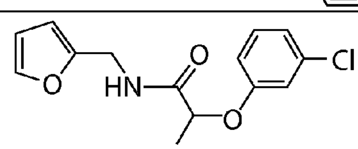 | 5699983 | 280 | 0% (0) | 13% (2.5) | |
| 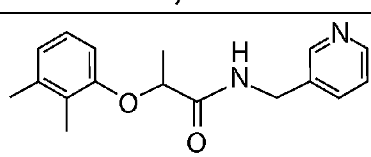 | 7403018 | 284 | 0% (-0.1) | 12% (2.7) | |
| 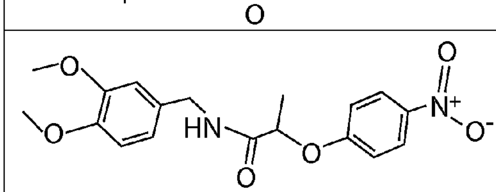 | 8817481 | 360 | 0% (-0.1) | 19% (3.4) | |
| 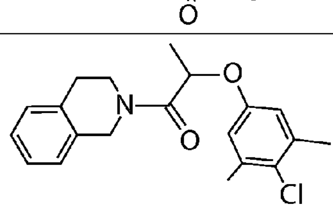 | 8815601 | 344 | -1% (-0.1) | 18% (3.2) | |

| Structure | Compound Identifier | MW | AVG % Inhibition of exoT-lux at 50 μM (Z-score) | AVG % Inhibition of lac-lux at 50 μM (Z-score) | IC$_{50}$ (μM) for Inhibition of ExoS'-βLA Secretion |
|---|---|---|---|---|---|
| 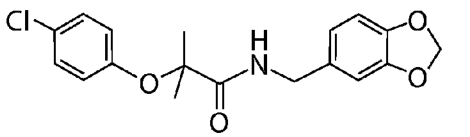 | 7337117 | 348 | -1% (-0.1) | 13% (3.1) | |
| 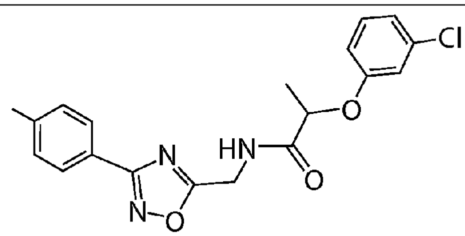 | 7994174 | 372 | -1% (-0.2) | 8% (1.3) | |
| 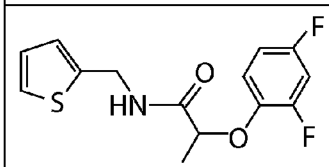 | 9093717 | 297 | -1% (-0.2) | 13% (2.4) | |
| 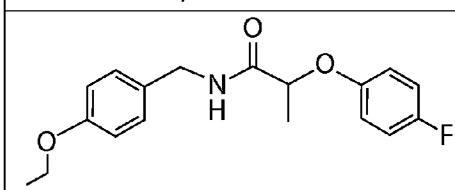 | 9146843 | 317 | -1% (-0.2) | 20% (3.5) | |
| 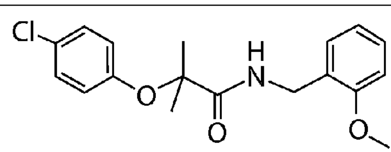 | 7346733 | 334 | -2% (-0.2) | 12% (2.8) | |
| 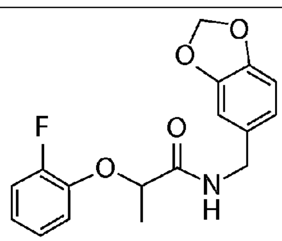 | 7339628 | 317 | -2% (-0.2) | 16% (3.8) | >100 |

| Structure | Compound Identifier | MW | AVG % Inhibition of exoT-lux at 50 µM (Z-score) | AVG % Inhibition of lac-lux at 50 µM (Z-score) | IC$_{50}$ (µM) for Inhibition of ExoS'-βLA Secretion |
|---|---|---|---|---|---|
| 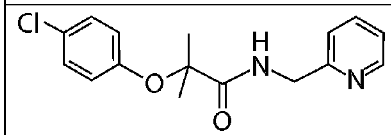 | 7320598 | 305 | -2% (-0.2) | 5% (1.4) | |
| 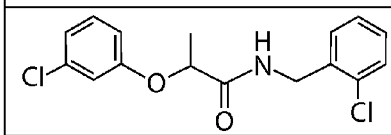 | 7631617 | 324 | -2% (-0.3) | 19% (4.4) | |
| 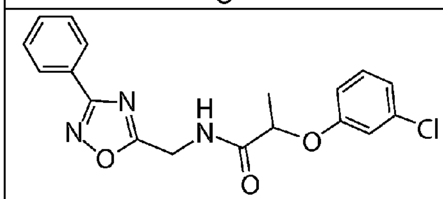 | 9004603 | 358 | -2% (-0.3) | 17% (2.9) | |
| 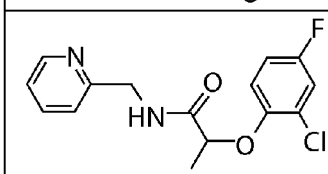 | 9092469 | 309 | -3% (-0.4) | 19% (3.5) | |
| 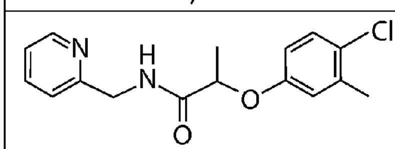 | 9008665 | 305 | -3% (-0.4) | 19% (3.2) | |
| 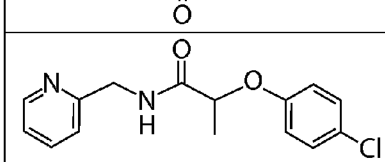 | 9072749 | 291 | -3% (-0.4) | 21% (3.7) | |
| 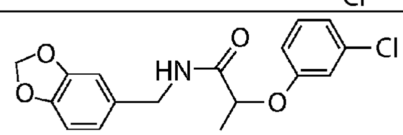 | 7303859 | 334 | -3% (-0.4) | 19% (3.9) | >100 |

Fig. 8J

| Structure | Compound Identifier | MW | AVG % Inhibition of exoT-lux at 50 μM (Z-score) | AVG % Inhibition of lac-lux at 50 μM (Z-score) | IC$_{50}$ (μM) for Inhibition of ExoS'-βLA Secretion |
|---|---|---|---|---|---|
| 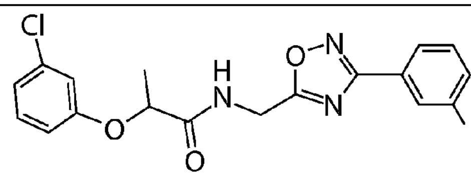 | 7999188 | 372 | -3% (-0.5) | 13% (2.4) | |
| 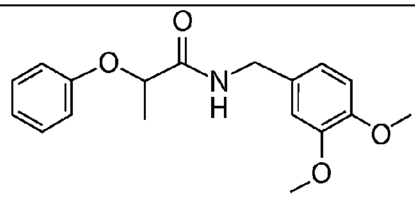 | 9011236 | 315 | -3% (-0.4) | 14% (2.4) | |
| 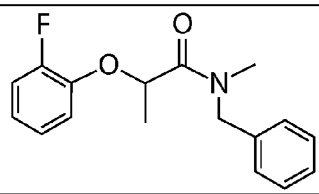 | 7321995 | 287 | -4% (-0.5) | 14% (2.8) | |
| 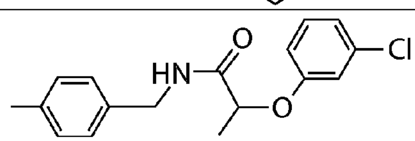 | 7282756 | 304 | -4% (-0.6) | 17% (4) | |
| 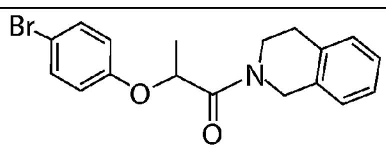 | 7778780 | 360 | -4% (-0.6) | 3% (0.8) | |
| 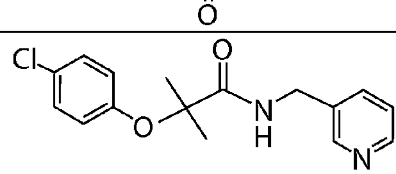 | 6449914 | 305 | -4% (-0.6) | 1% (0.7) | |
| 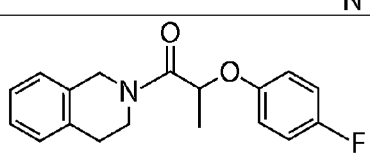 | 9079184 | 299 | -5% (-0.6) | 23% (4.1) | |

Fig. 8K

| Structure | Compound Identifier | MW | AVG % Inhibition of exoT-lux at 50 µM (Z-score) | AVG % Inhibition of lac-lux at 50 µM (Z-score) | IC$_{50}$ (µM) for Inhibition of ExoS'-βLA Secretion |
|---|---|---|---|---|---|
| 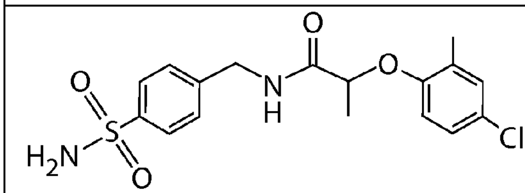 | 7225800 | 383 | -5% (-0.6) | 1% (0.3) | |
| 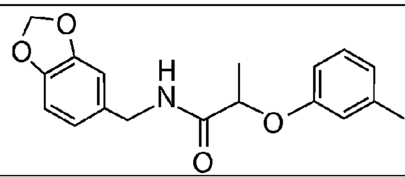 | 9077001 | 313 | -5% (-0.7) | 21% (3.7) | |
| 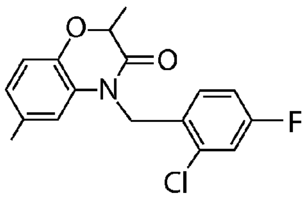 | 9113794 | 320 | -5% (-0.7) | 17% (3.1) | |
| 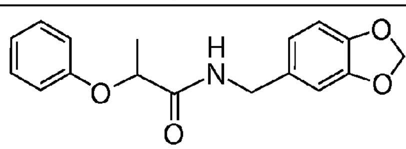 | 6428685 | 299 | -5% (-0.7) | 7% (1.6) | |
| 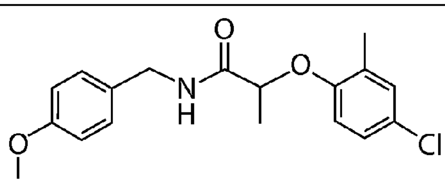 | 7270639 | 334 | -5% (-0.8) | 13% (3.1) | |
| 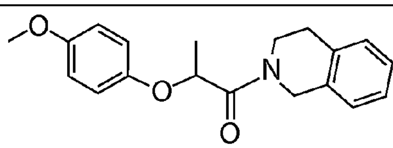 | 7775867 | 311 | -5% (-0.8) | 11% (2.6) | |
| 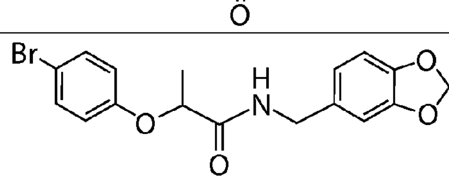 | 7780547 | 378 | -5% (-0.8) | 6% (1.6) | |

| Structure | Compound Identifier | MW | AVG % Inhibition of exoT-lux at 50 µM (Z-score) | AVG % Inhibition of lac-lux at 50 µM (Z-score) | IC$_{50}$ (µM) for Inhibition of ExoS'-βLA Secretion |
|---|---|---|---|---|---|
| 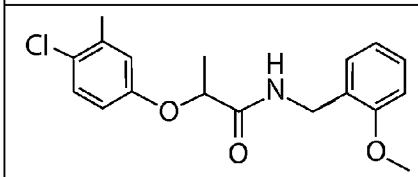 | 9014209 | 334 | -5% (-0.8) | 15% (2.6) | |
| 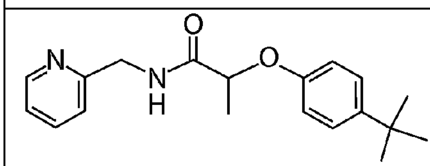 | 7902425 | 312 | -6% (-0.8) | 43% (9) | |
| 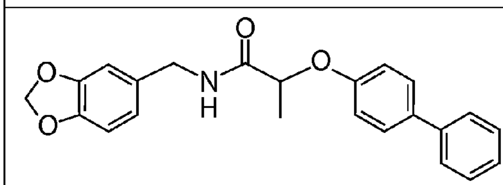 | 7948406 | 375 | -6% (-0.9) | 10% (1.8) | |
| 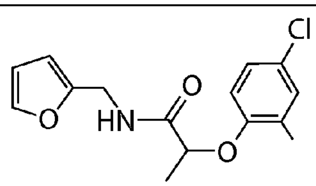 | 6122947 | 294 | -6% (-0.9) | 5% (1.1) | |
| 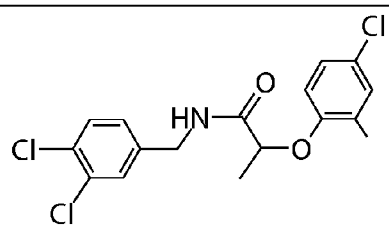 | 7219850 | 373 | -6% (-0.9) | 11% (2.5) | |
| 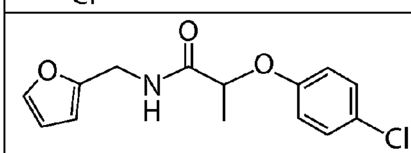 | 9017965 | 280 | -7% (-1) | 19% (3.3) | |
| 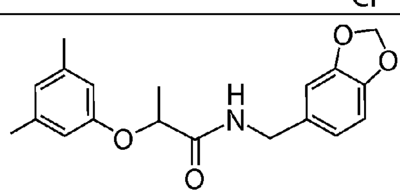 | 7395214 | 327 | -7% (-1) | 5% (1) | |

Fig. 8M

| Structure | Compound Identifier | MW | AVG % Inhibition of exoT-lux at 50 μM (Z-score) | AVG % Inhibition of lac-lux at 50 μM (Z-score) | IC$_{50}$ (μM) for Inhibition of ExoS'-βLA Secretion |
|---|---|---|---|---|---|
| Br-phenyl-O-CH(CH₃)-C(=O)-NH-CH₂-(2-Cl-phenyl) | 7779883 | 369 | -7% (-1.1) | 7% (1.5) | |
| thiophene-CH₂-NH-C(=O)-CH(CH₃)-O-(3-Cl-phenyl) | 7280215 | 296 | -8% (-1.2) | 18% (4) | |
| phenyl-O-CH₂CH₂-NH-C(=O)-CH(CH₃)-O-(2,4-diCl-phenyl) | 7955075 | 354 | -8% (-1.1) | 5% (-0.8) | |
| (2,4-diMe-phenyl)-O-CH(CH₃)-C(=O)-NH-CH₂-(4-pyridyl) | 9069386 | 284 | -8% (-1.3) | 15% (2.7) | |
| (4-MeO-phenyl)-O-CH(CH₃)-C(=O)-NH-CH₂-benzodioxole | 7756759 | 329 | -8% (-1.2) | 5% (1.3) | |
| (3-Cl-phenyl)-O-CH(CH₃)-C(=O)-NH-CH₂-(2-MeO-phenyl) | 7636682 | 320 | -9% (-1.2) | 11% (2.6) | |
| (4-Cl-phenyl)-O-CH(CH₃)-C(=O)-NH-CH₂-(3-pyridyl) | 6436224 | 291 | -9% (-1.2) | 12% (2.6) | |
| (2,4-diMe-phenyl)-O-CH(CH₃)-C(=O)-NH-CH₂-phenyl | 9059903 | 283 | -10% (-1.5) | 16% (2.8) | |

Fig. 8N

| Structure | Compound Identifier | MW | AVG % Inhibition of exoT-lux at 50 μM (Z-score) | AVG % Inhibition of lac-lux at 50 μM (Z-score) | IC$_{50}$ (μM) for Inhibition of ExoS'-βLA Secretion |
|---|---|---|---|---|---|
| 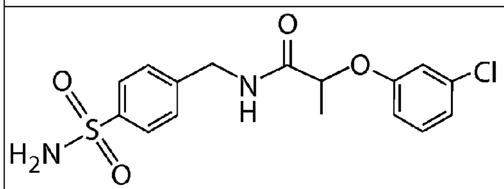 | 7294617 | 369 | -10% (-1.4) | 1% (0.4) | |
| 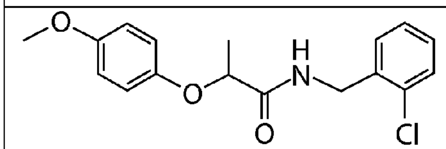 | 7748599 | 320 | -10% (-1.5) | 4% (1.1) | |
| 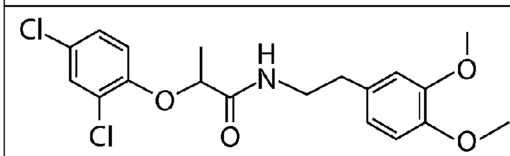 | 6382074 | 398 | -11% (-1.5) | 5% (1.4) | |
| 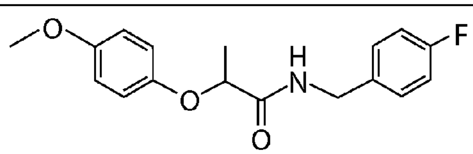 | 7769146 | 303 | -11% (-1.5) | 10% (2.2) | |
| 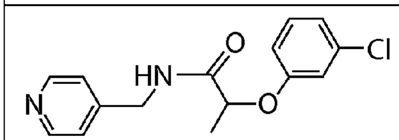 | 6126135 | 291 | -11% (-1.6) | 3% (0.6) | |
| 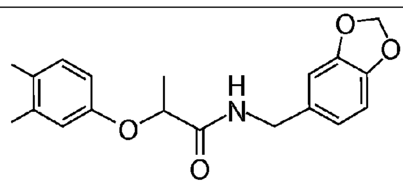 | 7412712 | 327 | -12% (-1.6) | 4% (1.2) | |
| 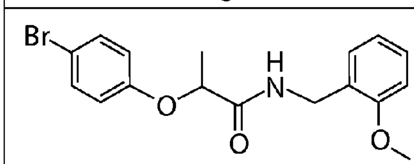 | 7782126 | 364 | -12% (-1.7) | 3% (0.9) | |

Fig. 8O

| Structure | Compound Identifier | MW | AVG % Inhibition of exoT-lux at 50 µM (Z-score) | AVG % Inhibition of lac-lux at 50 µM (Z-score) | IC$_{50}$ (µM) for Inhibition of ExoS'-βLA Secretion |
|---|---|---|---|---|---|
| 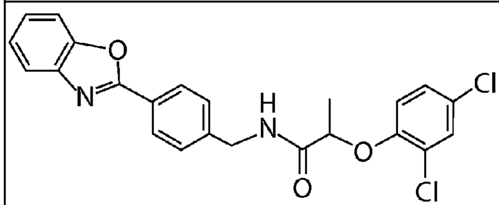 | 7967267 | 441 | -14% (-2) | -2% (-0.2) | |
| 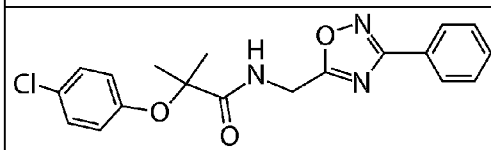 | 7956758 | 372 | -15% (-2) | -4% (-0.6) | |
| 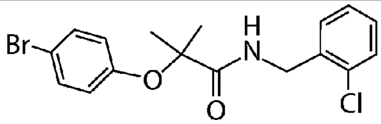 | 7956175 | 383 | -15% (-2.1) | 1% (0.3) | |
| 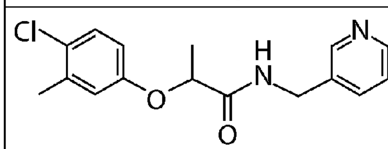 | 7447885 | 305 | -16% (-2.2) | 11% (2.6) | |
| 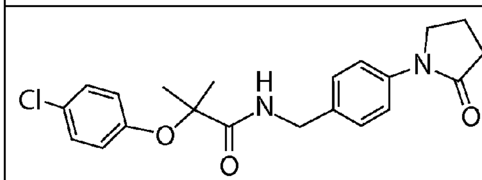 | 7980573 | 387 | -17% (-2.4) | 4% (1) | |
| 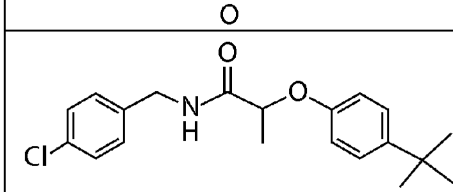 | 7893929 | 346 | -17% (-2.4) | 8% (1.9) | |
| 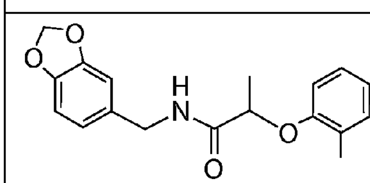 | 7968820 | 313 | -17% (-2.4) | 3% (0.9) | |

Fig. 8P

| Structure | Compound Identifier | MW | AVG % Inhibition of exoT-lux at 50 μM (Z-score) | AVG % Inhibition of lac-lux at 50 μM (Z-score) | IC$_{50}$ (μM) for Inhibition of ExoS'-βLA Secretion |
|---|---|---|---|---|---|
| (3,4-dichlorobenzyl)-NH-C(=O)-CH(CH₃)-O-(3-chlorophenyl) | 7229422 | 359 | -18% (-2.6) | 25% (5.5) | |
| (pyridin-3-yl-methyl)-NH-C(=O)-CH(CH₃)-O-(2-methylphenyl) | 7969489 | 270 | -19% (-2.6) | 3% (0.6) | |
| (4-methoxyphenyl-oxadiazolyl-methyl)-NH-C(=O)-CH(CH₃)-O-(3-chlorophenyl) | 7975109 | 388 | -19% (-2.7) | 0% (0.1) | |
| (3-trifluoromethylphenyl)-O-CH(CH₃)-C(=O)-NH-CH₂-(benzodioxole) | 7949586 | 367 | -21% (-2.9) | 12% (2.6) | |
| (4-chloro-3,5-dimethylphenyl)-O-CH(CH₃)-C(=O)-NH-CH₂-(pyridin-4-yl) | 7437956 | 319 | -24% (-3.4) | -4% (-0.6) | |

Fig. 8Q

INHIBITORS OF BACTERIAL TYPE III SECRETION SYSTEM

CROSS-REFERENCE TO RELATED APPLICATIONS

This application is a United States national stage filing under 35 U.S.C. §371 of international (PCT) application no. PCT/US2010/030120, filed Apr. 6, 2010, and designating the US, which claims priority to U.S. Provisional Appln. No. 61/212,021 filed Apr. 6, 2009, U.S. Provisional Appln. No. 61/304,305 filed Feb. 12, 2010, and U.S. Provisional Appln. No. 61/304,978 filed Feb. 16, 2010.

STATEMENT REGARDING FEDERALLY SPONSORED RESEARCH

This invention was made with government support under grant AI068185 awarded by the National Institutes of Health. The government has certain rights in the invention.

FIELD OF THE INVENTION

This invention is in the field of therapeutic drugs to treat bacterial infection and disease. In particular, the invention provides organic compounds that inhibit the type III secretion system of one or more bacterial species.

BACKGROUND OF THE INVENTION

The bacterial type III secretion system (T3SS) is a complex multi-protein apparatus that facilitates the secretion and translocation of effector proteins from the bacterial cytoplasm directly into the mammalian cytosol. This complex protein delivery device is shared by over 15 species of Gram-negative human pathogens, including *Salmonella* spp., *Shigella flexneri, Pseudomonas aeruginosa, Yersinia* spp., enteropathogenic and enteroinvasive *Escherichia coli*, and *Chlamydia* spp. (23, 25, 43). In the opportunistic pathogen *P. aeruginosa*, the T3SS is the major virulence factor contributing to the establishment and dissemination of acute infections (19). Four T3SS effectors have been identified in *P. aeruginosa* strains—ExoS, ExoT, ExoY, and ExoU. ExoS and ExoT are bifunctional proteins consisting of an N-terminal small G-protein activating protein (GAP) domain and a C-terminal ADP ribosylation domain; ExoY is an adenylate cyclase; and ExoU is a phospholipase [reviewed in (11)]. In studies with strains producing each effector separately, ExoU and ExoS contributed significantly to persistence, dissemination, and mortality while ExoT produced minor effects on virulence in a mouse lung infection model, and ExoY did not appear to play a major role in the pathogenesis of *P. aeruginosa* (51). While not a prototypical effector toxin, flagellin (FliC) may also be injected into the cytoplasm of host cells from *P. aeruginosa* via the T3SS machinery where it triggers activation of the innate immune system through the nod-like receptor NLRC4 inflammasome (13, 33).

The presence of a functional T3SS is significantly associated with poor clinical outcomes and death in patients with lower respiratory and systemic infections caused by *P. aeruginosa* (48). In addition, T3SS reduces survival in *P. aeruginosa* animal infection models (49), and is required for the systemic dissemination of *P. aeruginosa* in a murine acute pneumonia infection model (56). T3SS appears to contribute to the development of severe pneumonia by inhibiting the ability of the host to contain and clear bacterial infection of the lung. Secretion of T3SS toxins, particularly ExoU, blocks phagocyte-mediated clearance at the site of infection and facilitates establishment of an infection (9). The result is a local disruption of an essential component of the innate immune response, which creates an environment of immunosuppression in the lung. This not only allows *P. aeruginosa* to persist in the lung, but it also facilitates superinfection with other species of bacteria.

While several antibacterial agents are effective against *P. aeruginosa*, the high rates of mortality and relapse associated with serious *P. aeruginosa* infections, even in patients with hospital-acquired pneumonia (HAP) receiving antibiotics active against the causative strain, reflect the increasing incidence of drug-resistant strains and highlights the need for new therapeutic agents (10, 46, 52). Conventional bacteriostatic and bactericidal antibiotics appear insufficient to adequately combat these infections, and new treatment approaches such as inhibitors of *P. aeruginosa* virulence determinants may prove useful as adjunctive therapies (58).

The potential for T3SS as a therapeutic target has prompted several groups to screen for inhibitors of T3SS in various bacterial species, including *Salmonella typhimurium, Yersinia pestis, Y. pseudotuberculosis*, and *E. coli* [reviewed in (5, 25)]. However, only a single screen for inhibitors of *P. aeruginosa* T3SS inhibitors has been reported, and it yielded specific inhibitors of one of the T3SS effectors, ExoU (27) rather than inhibitors of the T3SS machinery. High levels of sequence conservation among various proteins comprising the T3SS apparatus suggest that inhibitors of T3SS in one species may also be active in related species. Broad spectrum activity of T3SS inhibitors identified in a screen against *Yersinia* has been demonstrated in *Salmonella, Shigella*, and *Chlamydia* (22, 57, 59).

Clearly, needs remain for new, potent inhibitors of bacterial T3SS of *P. aeruginosa* and other bacterial species.

SUMMARY OF THE INVENTION

The invention addresses the above problems by providing new bacterial type III secretion system (T3SS) inhibitor compounds. To identify T3SS inhibitory compounds described herein, a cell-based bioluminescent reporter assay was developed and employed as a high throughput primary screen to identify putative inhibitors of the *P. aeruginosa* T3SS from libraries of thousands of organic compounds. The putative T3SS inhibitor compounds ("hits") from the high throughput primary screen were then qualified through a series of secondary assays. Accordingly, a T3SS inhibitor described herein inhibits T3SS-mediated secretion of a bacterial exotoxin (effector) from a bacterial cell. More preferably, a T3SS inhibitor compound described herein inhibits T3SS-mediated secretion of an effector from a bacterial cell and also inhibits T3SS-mediated translocation of the effector from the bacterial cell to a host cell (e.g., human or other animal cell).

In a preferred embodiment, a T3SS inhibitor compound described herein inhibits the T3SS in a bacterium of the genus *Pseudomonas, Yersinia*, or *Chlamydia*.

In another embodiment, a T3SS inhibitor compound described herein inhibits the T3SS of *Pseudomonas* and the T3SS of a bacterium of at least one other genus. Preferably, the inhibition target *Pseudomonas* bacterium is *P. aeruginosa*. Preferably, the other bacterial genus susceptible to T3SS inhibition by compound(s) of the invention is *Yersinia* or *Chlamydia*. A preferred inhibition target species of *Yersinia* is *Y. pestis*. A preferred inhibition target species of *Chlamydia* is *C. trachomatis*.

The present invention provides several specific bacterial T3SS inhibitor compounds, listed below by structure, manufacturer's designation, and chemical name:

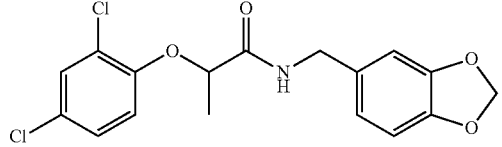 [SMILES: CC(Oc1ccc(Cl)cc1Cl)C(=O)NCc1ccc2c(c1)OCO2]

compound 1 (ChemBridge 5690431; Microbiotix MBX 1641; racemate)
N-(benzo[d][1,3]dioxol-5-ylmethyl)-2-(2,4-dichlorophenoxy)propanamide

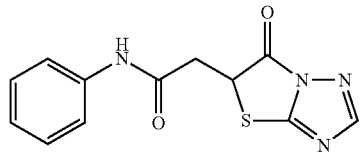 [SMILES: O=C(CC1Sc2ncnn2C1=O)Nc1ccccc1]

compound 2 (TimTec 7803985)
2-(6-oxo-5,6-dihydrothiazolo[3,2-b][1,2,4]triazol-5-yl)-N-phenylacetamide

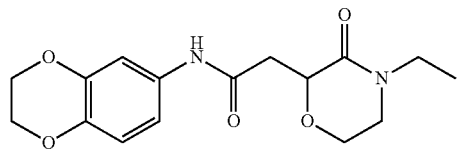 [SMILES: CCN1CCOC(CC(=O)Nc2ccc3c(c2)OCCO3)C1=O]

compound 3 (ChemBridge 7817424)
N-(2,3-dihydrobenzo[b][1,4]dioxin-6-yl)-2-(4-ethyl-3-oxo-morpholin-2-yl)acetamide

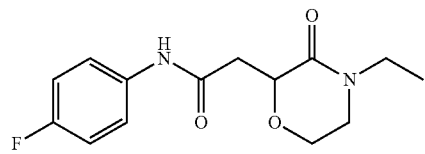 [SMILES: CCN1CCOC(CC(=O)Nc2ccc(F)cc2)C1=O]

compound 4 (ChemBridge 7836532)
2-(4-ethyl-3-oxomorpholin-2-yl)-N-(4-fluorophenyl)acetamide

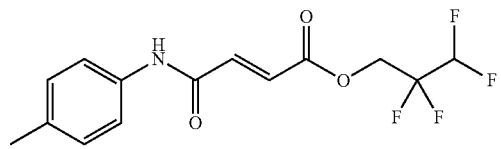 [SMILES: Cc1ccc(NC(=O)/C=C/C(=O)OCC(F)(F)C(F)F)cc1]

compound 5 (ChemBridge 5251671)
(E)-2,2,3,3-tetrafluoropropyl 4-oxo-4-(p-tolylamino)but-2-enoate

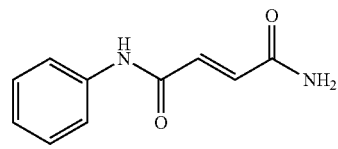 [SMILES: NC(=O)/C=C/C(=O)Nc1ccccc1]

compound 6 (ChemBridge 5268081)
N1-phenylfumaramide

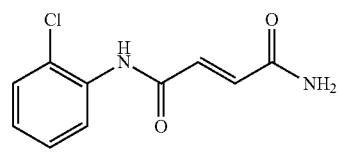 [SMILES: NC(=O)/C=C/C(=O)Nc1ccccc1Cl]

compound 7 (ChemBridge 5278959)
N1-(2-chlorophenyl)fumaramide

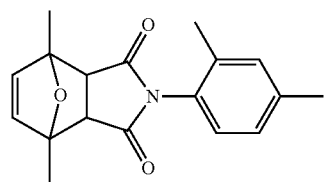 [SMILES: Cc1ccc(N2C(=O)C3C(C2=O)C2(C)C=CC3(C)O2)c(C)c1]

compound 8 (ChemBridge ST026942)
2-(2,4-dimethylphenyl)-4,7-dimethyl-3a,4,7,7a-tetrahydro-1H-4,7-epoxyisoindole-1,3(2H)-dione

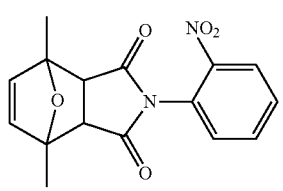 [SMILES: CC12C=CC(C)(O1)C1C(=O)N(c3ccccc3[N+](=O)[O-])C(=O)C12]

compound 9 (TimTec ST002413)
(3aS,4R,7R,7aR)-4-methyl-2-(2-nitrophenyl)-3a,4,7,7a-tetrahydro-1H-4,7-epoxyisoindole-1,3(2H)-dione

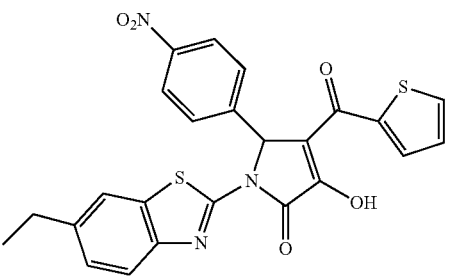 [SMILES: CCc1ccc2nc(N3C(=O)C(O)=C(C(=O)c4cccs4)C3c3ccc([N+](=O)[O-])cc3)sc2c1]

compound 10 (TimTec 7741077)

1-(6-ethylbenzo[d]thiazol-2-yl)-3-hydroxy-5-(4-nitrophenyl)-4-(thiophene-2-carbonyl)-1H-pyrrol-2(5H)-one 2-(2,4-dichlorophenoxy)-N-(4-fluorobenzyl)propanamide

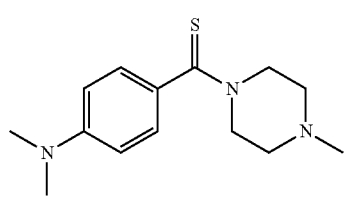

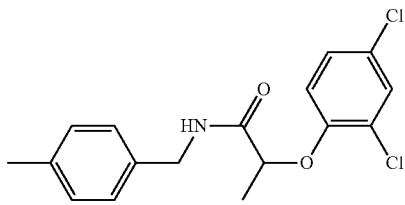

compound 11 (ChemBridge 7828938)
(4-(dimethylamino)phenyl)(4-methylpiperazin-1-yl)methanethione 6109233 (ChemBridge)
2-(2,4-dichlorophenoxy)-N-(4-methylbenzyl)propanamide

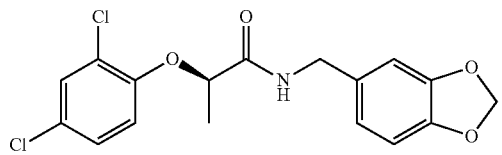 [SMILES: C[C@@H](Oc1ccc(Cl)cc1Cl)C(=O)NCc1ccc2c(c1)OCO2]

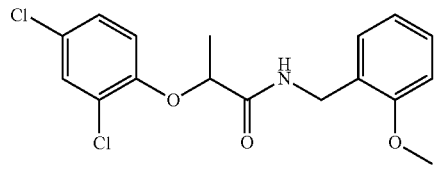

MBX 1684 (Microbiotix; R-stereoisomer of MBX 1641, supra)
(R)-N-(benzo[d][1,3]dioxol-5-ylmethyl)-2-(2,4-dichlorophenoxy)propanamide 6374948 (ChemBridge)
2-(2,4-dichlorophenoxy)-N-(2-methoxybenzyl)propanamide

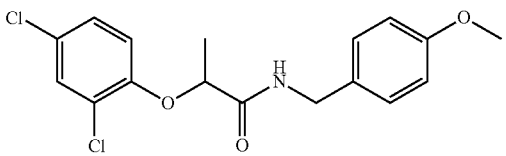 [SMILES: COc1ccc(CNC(=O)C(C)Oc2ccc(Cl)cc2Cl)cc1]

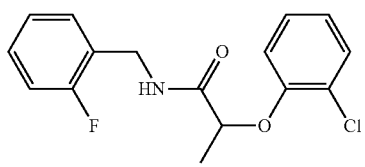

6375680 (ChemBridge)
2-(2,4-dichlorophenoxy)-N-(4-methoxybenzyl)propanamide 9101768 (ChemBridge)
2-(2-chlorophenoxy)-N-(2-fluorobenzyl)propanamide

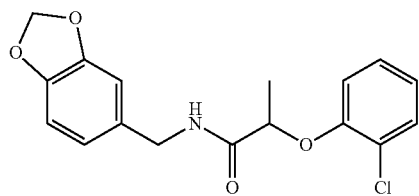 [SMILES: CC(Oc1ccccc1Cl)C(=O)NCc1ccc2c(c1)OCO2]

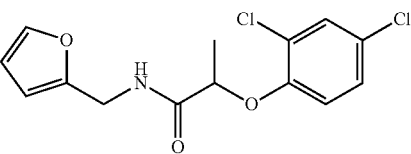

9153915 (ChemBridge)
N-(1,3-benzodioxol-5-ylmethyl)-2-(2-chlorophenoxy)propanamide 5685325 (ChemBridge)
2-(2,4-dichlorophenoxy)-N-(2-furylmethyl)propanamide

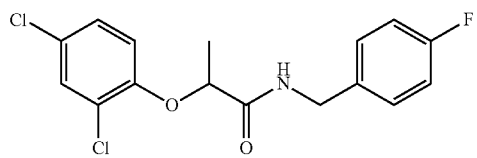 [SMILES: CC(Oc1ccc(Cl)cc1Cl)C(=O)NCc1ccc(F)cc1]

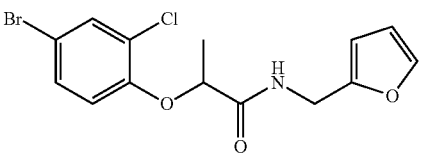 [SMILES: CC(Oc1ccc(Br)cc1Cl)C(=O)NCc1ccco1]

6380194 (ChemBridge)

7945429 (ChemBridge)

2-(4-bromo-2-chlorophenoxy)-N-(2-furylmethyl)propanamide

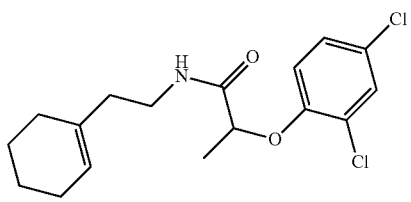 [SMILES: CC(Oc1ccc(Cl)cc1Cl)C(=O)NCCC1=CCCCC1]

6467504 (ChemBridge)
N-[2-(1-cyclohexen-1-yl)ethyl]-2-(2,4-dichlorophenoxy)propanamide

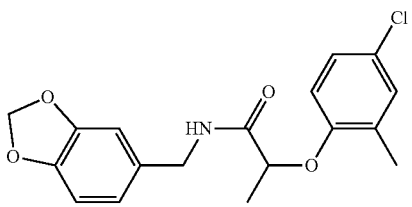 [SMILES: Cc1cc(Cl)ccc1OC(C)C(=O)NCc1ccc2c(c1)OCO2]

6116488 (ChemBridge)
N-(1,3-benzodioxol-5-ylmethyl)-2-(4-chloro-2-methylphenoxy)propanamide

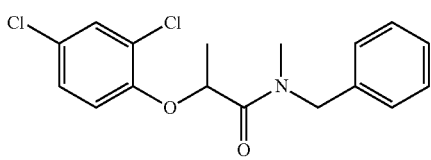 [SMILES: CC(Oc1ccc(Cl)cc1Cl)C(=O)N(C)Cc1ccccc1]

6468028 (ChemBridge)
N-benzyl-2-(2,4-dichlorophenoxy)-N-methylpropanamide

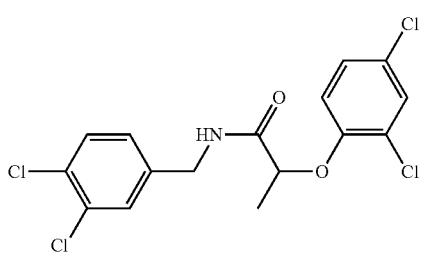 [SMILES: CC(Oc1ccc(Cl)cc1Cl)C(=O)NCc1ccc(Cl)c(Cl)c1]

7271715 (ChemBridge)
N-(3,4-dichlorobenzyl)-2-(2,4-dichlorophenoxy)propanamide

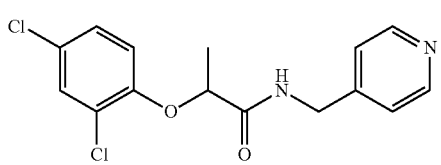 [SMILES: CC(Oc1ccc(Cl)cc1Cl)C(=O)NCc1ccncc1]

6372013 (ChemBridge)

2-(2,4-dichlorophenoxy)-N-(4-pyridinylmethyl)propanamide

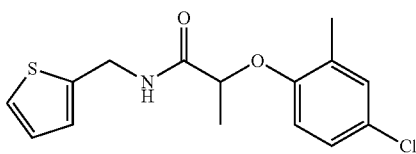 [SMILES: Cc1cc(Cl)ccc1OC(C)C(=O)NCc1cccs1]

7290938 (ChemBridge)
2-(4-chloro-2-methylphenoxy)-N-(2-thienylmethyl)propanamide

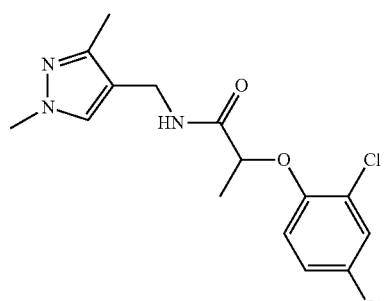

8804126 (ChemBridge)
2-(2,4-dichlorophenoxy)-N-[(1,3-dimethyl-1H-pyrazol-4-yl)methyl]propanamide

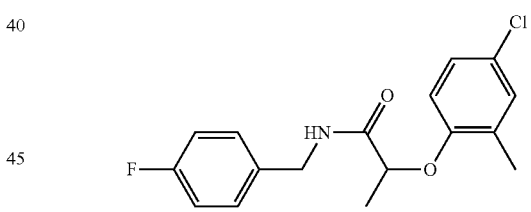

7306705 (ChemBridge)
2-(4-chloro-2-methylphenoxy)-N-(4-fluorobenzyl)propanamide

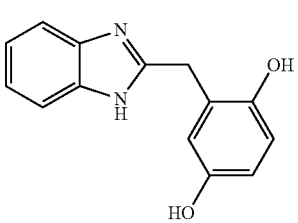 [SMILES: Oc1ccc(O)c(Cc2nc3ccccc3[nH]2)c1]

6430631 (ChemBridge)

2-((1H-benzo[d]imidazol-2-yl)methyl)benzene-1,4-diol

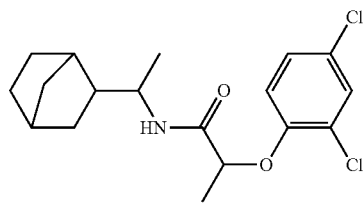 [SMILES: CC(Oc1ccc(Cl)cc1Cl)C(=O)NC(C)C1CC2CCC1C2]

7247834 (ChemBridge)
N-(1-(bicyclo[2.2.1]heptan-2-yl)ethyl)-2-(2,4-dichlorophenoxy)propanamide

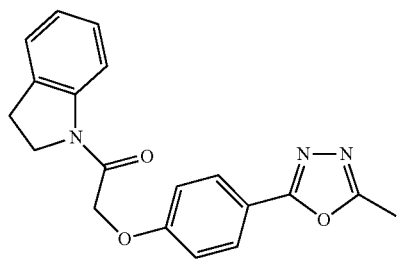 [SMILES: Cc1nnc(-c2ccc(OCC(=O)N3CCc4ccccc43)cc2)o1]

F5054-0019 (Life Chemicals)
1-(indolin-1-yl)-2-(4-(5-methyl-1,3,4-oxadiazol-2-yl)phenoxy)ethanone The foregoing compounds were identified by assays showing specific inhibition of the T3SS of *P. aeruginosa*. Selected compounds were additionally tested for inhibition of *Chlamydia trachomatis* and *Yersinia pestis* and showed effective inhibition, indicating that a T3SS inhibitor compound according to this invention can be an effective inhibitor of many bacterial type III secretion systems, acting across species within a genus and across genera of bacteria having type III secretion systems.

T3SS inhibitory properties discovered for the compounds of the invention are set forth in Table 3, Table 4, Table 5, and FIGS. 8A-8Q, infra. Inhibitor compounds were identified as inhibiting T3SS effector transcription by at least 15% at a concentration of 50 µM using a transcriptional reporter assay or by exhibiting at least 50% inhibition of effector secretion at a concentration of 100 µM or less ($IC_{50} \leq 100$ µM) in an effector secretion assay. The compounds listed above showed T3SS-specific inhibition in *Psuedomonas* of greater than 15% using an exoT-lux transcriptional reporter construct transferred into *Pseudomonas aeruginosa* PAO1 (reporter strain MDM852, described herein) and/or showed an $IC_{50}$ of less than 100 µM for T3SS as measured in an assay of T3SS-mediated secretion of an effector toxin-β-lactamase reporter fusion protein assay described herein using *P. aeruginosa* strain MDM973 (PAK/pUCP24GW-lacI$^Q$-lacPO-exoS::blaM) (Table 1). Compounds inhibiting effector transcription by less than 15% or with an $IC_{50}$ greater than 100 µM are not generally useful as T3SS inhibitors in the compositions and methods described herein.

In a particularly preferred embodiment, a T3SS inhibitor compound useful in the compositions and methods described herein has an $IC_{50}$ of less than 100 µM as measured in a T3SS-mediated effector toxin-β-lactamase reporter fusion protein secretion assay described herein (or comparable assay) and also has a relatively low cytotoxicity toward human cells, such as a $CC_{50}$ value of greater than or equal to 100 µM ($CC_{50} \geq 100$ µM) as measured in a standard cytotoxicity assay as described herein or as employed in the pharmaceutical field for antibiotics. Such standard cytotoxicity assays may employ any human cell typically employed in cytotoxicity assays for antibiotics, including but not limited to, Chinese hamster ovary (CHO) cells, HeLa cells, Hep-2 cells, human embryonic kidney (HEK) 293 cells, 293T cells, and the like.

Even more preferably, a T3SS inhibitor compound described herein has an $IC_{50}$ value $\leq 25$ µM as measured in a T3SS-mediated effector toxin-β-lactamase reporter fusion protein secretion assay as described herein or in a comparable assay.

In yet another embodiment, a T3SS inhibitor compound described herein has a sufficiently high minimal inhibitory concentration (MIC) to indicate that it inhibits T3SS specifically.

In a particularly preferred embodiment of the invention, a T3SS inhibitor compound is a phenoxyacetamide inhibitor that blocks T3SS-mediated secretion and translocation of one or more toxin effectors from cells of *P. aeruginosa*. More preferably, a phenoxyacetamide T3SS inhibitor of the invention is MBX 1641 (racemic mixture), which is the designation of re-synthesized phenoxyacetamide T3SS inhibitor compound 1 obtained from the screening and validation protocol described herein, and that has the structure

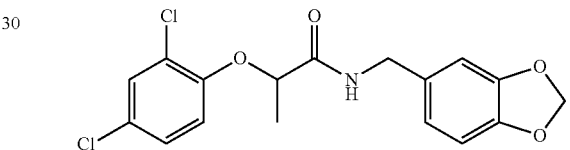

and properties shown in Tables 3 and 4 and FIG. 8A. Even more preferably, the phenoxyacetamide T3SS inhibitor compound is the R-isomer of MBX 1641, designated MBX 1684, which has the structure

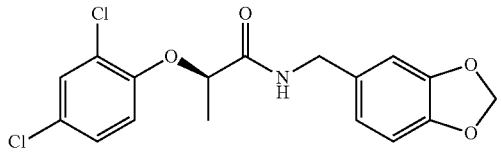 [SMILES: C[C@@H](Oc1ccc(Cl)cc1Cl)C(=O)NCc1ccc2c(c1)OCO2]

and properties shown in Table 4 and FIG. 8A, below.

In another embodiment, a T3SS inhibitor compound useful in the compositions and methods described herein is selected from the group of inhibitor compounds consisting of MBX 1641 (compound 1, FIG. 8A), MBX 1684 (R-isomer of MBX 1641) (see, FIG. 8A), compound 3 (see, Table 3), compound 4 (see, Table 3), compound 5685325 (see, FIG. 8B), compound 6380194 (see, FIG. 8B), compound 6430631 (see, Table 5), compound 7247834 (see, Table 5), compound F5054-0019 (see, Table 5), and combinations thereof.

The T3SS compounds described herein are useful as antibacterial or bacteriostatic agents and may be used to treat bacterial infections. Accordingly, an individual infected with or exposed to bacterial infection, especially *Pseudomonas*, *Yersinia* or *Chlamydia* infection, may be treated by administering to the individual in need an effective amount of a compound according to the invention, e.g., administering one or more of the following compounds:

11
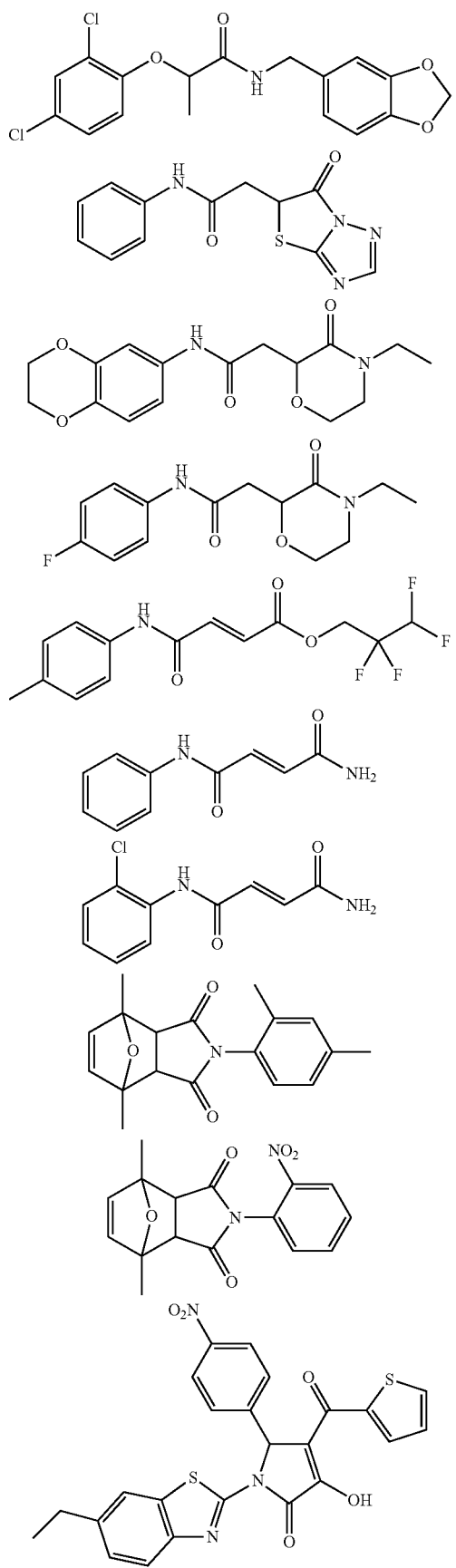
12
-continued
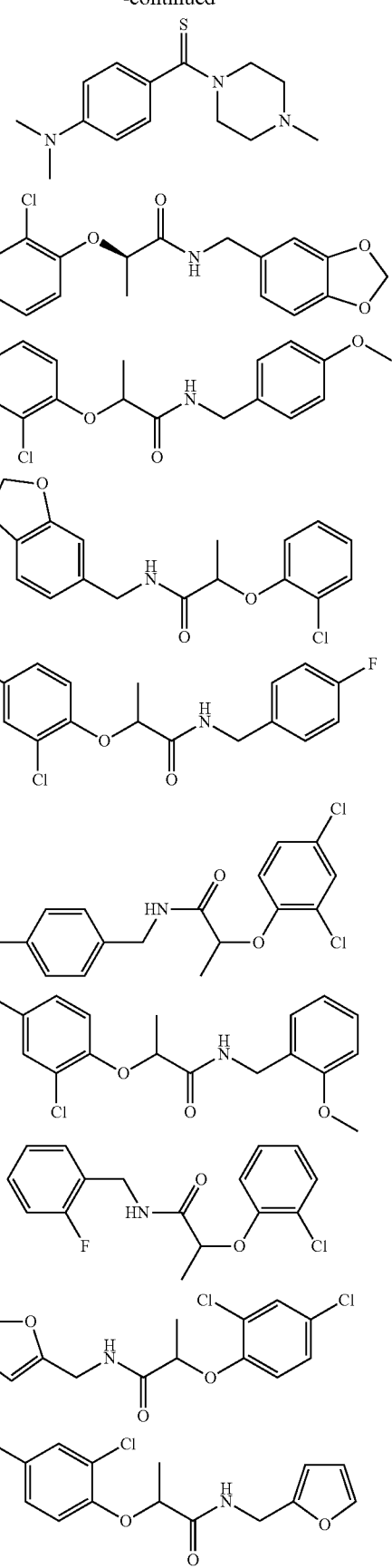

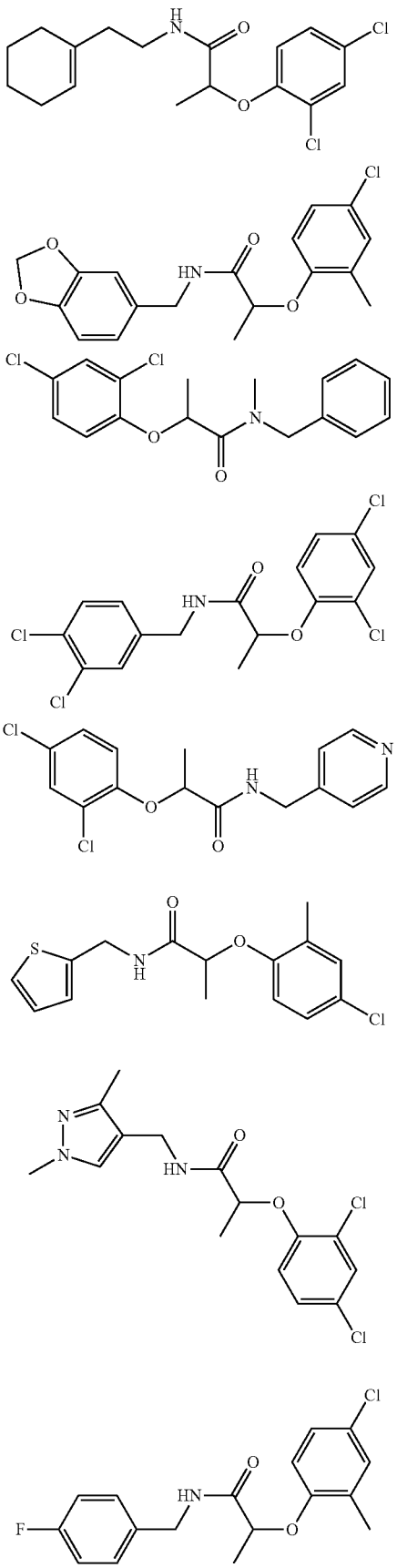
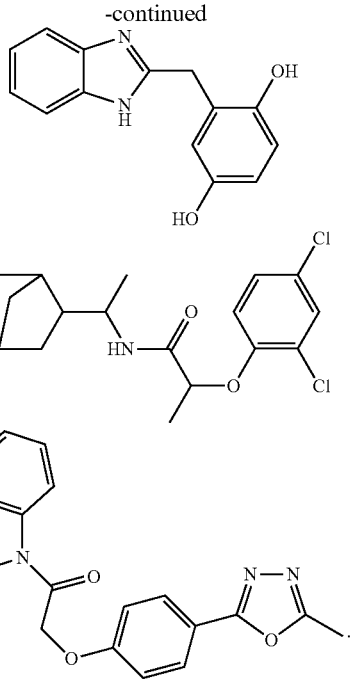

Use of one or more or a combination of the above compounds to treat infection by bacteria having a type III secretion system is contemplated herein. Especially, use of one or more or a combination of the above compounds to treat *Pseudomonas, Yersinia* or *Chlamydia* infection is contemplated herein. In particular, use of one or more or a combination of the above compounds for the treatment of *Pseudomonas aeruginosa, Yersinia pestis*, or *Chlamydia trachomatis* infections is advantageously carried out by following the teachings herein.

The present invention also provides pharmaceutical compositions containing one or more of the T3SS inhibitor compounds disclosed herein and a pharmaceutically acceptable carrier or excipient. The use of one or more of the T3SS inhibitor compounds in the preparation of a medicament for combating bacterial infection is disclosed.

A T3SS inhibitor compound or combination of T3SS inhibitor compounds described herein may be used as a supporting or adjunctive therapy for the treatment of bacterial infection in an individual (human or other animal). In the case of an individual with a healthy immune system, administration of a T3SS inhibitor compound described herein to inhibit the T3SS of bacterial cells in or on an individual may be sufficient to permit the individual's own immune system to effectively clear or kill infecting or contaminating bacteria from the tissue of the individual. Alternatively, a T3SS inhibitor compound described herein may be administered to an individual in conjunction (i.e., in a mixture, sequentially, or simultaneously) with an antibacterial agent, such as an antibiotic, an antibody, or immunostimulatory agent, to provide both inhibition of T3SS and inhibition of growth of invading bacterial cells.

In yet another embodiment, a composition comprising a T3SS inhibitor or a combination of T3SS inhibitors described herein may also comprise a second agent (second active ingredient, second active agent) that possesses a desired therapeutic or prophylactic activity other than that of T3SS inhibition. Such a second active agent includes, but is not limited to, an antibiotic, an antibody, an antiviral agent, an anticancer agent, an analgesic (e.g., a non-steroidal anti-inflammatory drug (NSAID), acetaminophen, an opioid, a COX-2 inhibitor), an immunostimulatory agent (e.g., a cytokine), a hormone (natural or synthetic), a central nervous system (CNS) stimulant, an antiemetic agent, an anti-histamine, an erythropoietin, a complement stimulating agent, a sedative, a muscle relaxant agent, an anesthetic agent, an anticonvulsive agent, an antidepressant, an antipsychotic agent, and combinations thereof.

Compositions comprising a T3SS inhibitor described herein may be formulated for administration to an individual (human or other animal) by any of a variety of routes including, but not limited to, intravenous, intramuscular, subcutaneous, intra-arterial, parenteral, intraperitoneal, sublingual (under the tongue), buccal (cheek), oral (for swallowing), topical (epidermis), transdermal (absorption through skin and lower dermal layers to underlying vasculature), nasal (nasal mucosa), intrapulmonary (lungs), intrauterine, vaginal, intracervical, rectal, intraretinal, intraspinal, intrasynovial, intrathoracic, intrarenal, nasojejunal, and intraduodenal.

BRIEF DESCRIPTION OF THE DRAWINGS

FIG. 1. Characterization of bioluminescent and chromogenic reporter strains for identification of T3SS inhibitors.

FIG. 2 shows an evaluation of inhibition of type III and type II secretion in *P. aeruginosa*. *P. aeruginosa* ExoS-secreting strain PAKΔTY was grown under T3SS inducing conditions (LB+5 mM EGTA) for 3 hours in the presence of the indicated concentrations of compounds. Culture medium (1 ml) was concentrated in SDS-PAGE sample buffer, separated by 12.5% SDS-PAGE, and stained with Coomassie Blue. The positive control, DMSO+EGTA, was treated with 5 mM EGTA but not inhibitors, and the negative control, DMSO-EGTA, was treated with neither EGTA nor inhibitors. Identity and molecular weight of protein markers are as follows: porcine myosin (200K), *E. coli* β-galactosidase (116K), rabbit muscle phosphorylase B (97K), bovine albumin (66K), ovalbumin (45K), and bovine carbonic anhydrase (29K).

FIG. 3 shows results of an analysis of inhibition of T3SS-mediated effects on mammalian cells incubated with *P. aeruginosa* cells in culture.

FIG. 4 shows inhibition of T3SS-mediated secretion of effector-β-lactamase fusion proteins by two bacterial species.

FIG. 5 shows an evaluation of the effects of MBX 1641 on bacterial and mammalian cell growth.

FIG. 7 shows plots of percent (%) cytotoxicity versus log of concentration of T3SS inhibitor compounds in studies of the ability of each of two T3SS inhibitor compounds (analogs of compound 1) to rescue CHO cells from ExoU cytotoxicity. The log of concentration of each inhibitor (μM) is plotted on the x-axis versus percent (%) cytotoxicity on the y-axis. % cytotoxicity is calculated as the % of LDH (lactate dehydrogenase) released from cells intoxicated with *P. aeruginosa*+/− inhibitor as compared to LDH released from cells lysed with Triton X-100 non-ionic detergent. Plots include % cytotoxicity in the presence of *P. aeruginosa* (black diamonds, ♦) as well as in the absence of *P. aeruginosa* (black squares, ■).

DETAILED DESCRIPTION OF THE INVENTION

Figure 1A:
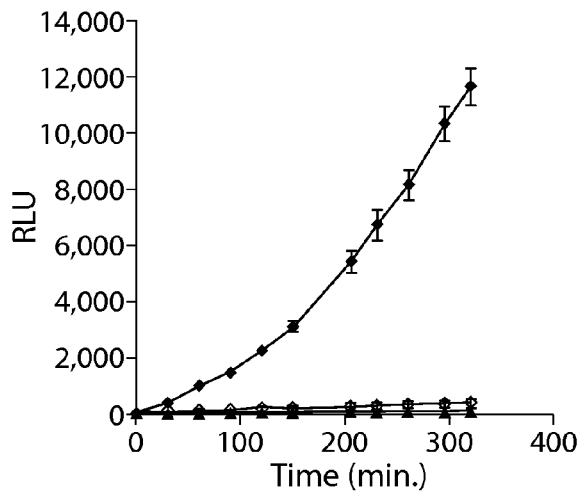
FIG. 1A shows luminescence (relative light units, RLU) from a chromosomal transcriptional fusion of exoT to the *P. luminescens* luxCDABE operon in wild-type (strain MDM852) or ΔpscC (strain MDM1355) *P. aeruginosa* PAO1 cells. Overnight cultures were diluted at time zero to $A_{600}$~0.025 and induced (+5 mM EGTA) or not induced (no added EGTA). RLU values were measured in 96-well opaque microplates throughout a 320 minute time course. Black diamonds, ♦, MDM852+5 mM EGTA; white diamonds, ◇, MDM852 with no added EGTA); black triangles ▲, MDM1355+5 mM EGTA; white triangles, △, MDM1355 with no added EGTA. See, Example 2, for details.

The invention provides organic compounds that inhibit a bacterial type III secretion system ("T3SS") that secretes and translocates bacterially produced effectors (also referred to as effector toxins, exotoxins, cytotoxins, bacterial toxins) from the bacterial cell into animal host cells. Effectors translocated into a host's cells can effectively inactivate the host immune response, such as by killing phagocytes and thereby disabling the host's innate immune response. The T3SS is thus a critical virulence factor in establishing bacterial infections in an individual (human or other animal) and is particularly critical to *P. aeruginosa* opportunistic infections of human patients with compromised immune systems or that otherwise have been made susceptible to infection by bacteria such as *P. aeruginosa*.

In order that the invention may be more clearly understood, the following abbreviations and terms are used as defined below.

Abbreviations for various substituents (side groups, radicals) of organic molecules are those commonly used in organic chemistry. Such abbreviations may include "shorthand" forms of such substituents. For example, "Ac" is an abbreviation for an acetyl group, "Ar" is an abbreviation for an "aryl" group, and "halo" or "halogen" indicates a halogen radical (e.g., F, Cl, Br, I). "Me" and "Et" are abbreviations used to indicate methyl ($CH_3$—) and ethyl ($CH_3CH_2$—) groups, respectively; and "OMe" (or "MeO") and "OEt" (or "EtO") indicate methoxy ($CH_3O$—) and ethoxy ($CH_3CH_2O$—), respectively. Hydrogen atoms are not always shown in organic molecular structures or may be only selectively shown in some structures, as the presence and location of hydrogen atoms in organic molecular structures are understood and known by persons skilled in the art. Likewise, carbon atoms are not always specifically abbreviated with "C", as the presence and location of carbon atoms, e.g., between or at the end of bonds, in structural diagrams are known and understood by persons skilled in the art. Minutes are commonly abbreviated as "min"; hours are commonly abbreviated as "hr" or "h".

A composition or method described herein as "comprising" one or more named elements or steps is open-ended, meaning that the named elements or steps are essential, but other elements or steps may be added within the scope of the composition or method. To avoid prolixity, it is also understood that any composition or method described as "comprising" (or which "comprises") one or more named elements or steps also describes the corresponding, more limited composition or method "consisting essentially of" (or which "consists essentially of") the same named elements or steps, meaning that the composition or method includes the named essential elements or steps and may also include additional elements or steps that do not materially affect the basic and novel characteristic(s) of the composition or method. It is also understood that any composition or method described herein as "comprising" or "consisting essentially of" one or more named elements or steps also describes the corresponding, more limited, and closed-ended composition or method "consisting of" (or "consists of") the named elements or steps to the exclusion of any other unnamed element or step. In any composition or method disclosed herein, known or disclosed equivalents of any named essential element or step may be substituted for that element or step. It is also understood that an element or step "selected from the group consisting of" refers to one or more of the elements or steps in the list that follows, including combinations of any two or more of the listed elements or steps.

The terms "bacterial type III secretion system inhibitor", "bacterial T3SS inhibitor", "bacterial T3SS inhibitor compound", and "T3SS inhibitor compound" as used herein are interchangeable and denote compounds exhibiting the ability to specifically inhibit a bacterial type III secretion system by at least 15% at a concentration of 50 µM, for example as measured in a T3SS effector transcriptional reporter assay or the ability to inhibit a bacterial T3SS, for example as measured in a T3SS-mediated effector toxin secretion assay.

In the context of therapeutic use of the T3SS inhibitor compounds described herein, the terms "treatment", "to treat", or "treating" will refer to any use of the T3SS inhibitor compounds calculated or intended to arrest or inhibit the virulence or the T3SS-mediated effector secretion or translocation of bacteria having type III secretion systems. Thus, treating an individual may be carried out after any diagnosis indicating possible bacterial infection, i.e., whether an infection by a particular bacterium has been confirmed or whether the possibility of infection is only suspected, for example, after an individual's exposure to the bacterium or to another individual infected by the bacterium. It is also recognized that while the inhibitors of the present invention affect the introduction of effector toxins into host cells, and thus block or decrease the virulence or toxicity resulting from infection, the inhibitor compounds are not necessarily bacteriocidal or effective to inhibit growth or propagation of bacterial cells. For this reason, it will be understood that elimination of the bacterial infection will be accomplished by the host's own immune system or immune effector cells, or by introduction of antibiotic agents. Thus, it is contemplated that the compounds of the present invention will be routinely combined with other active ingredients such as antibiotics, antibodies, antiviral agents, anticancer agents, analgesics (e.g., a non-steroidal anti-inflammatory drug (NSAID), acetaminophen, opioids, COX-2 inhibitors), immunostimulatory agents (e.g., cytokines or a synthetic immunostimulatory organic molecules), hormones (natural, synthetic, or semi-synthetic), central nervous system (CNS) stimulants, antiemetic agents, anti-histamines, erythropoietin, agents that activate complement, sedatives, muscle relaxants, anesthetic agents, anticonvulsive agents, antidepressants, antipsychotic agents, and combinations thereof.

The meaning of other terms will be understood by the context as understood by the skilled practitioner in the art, including the fields of organic chemistry, pharmacology, and microbiology.

The invention provides specific organic compounds that inhibit the T3SS of *Pseudomonas aeruginosa*. Putative T3SS inhibitors ("hits") were initially identified in screening libraries of organic molecules with a *P. aeruginosa* cell-based luminescent reporter assay (*P. aeruginosa* MDM852 (PA01::pGSV3-exoT-luxCDABE, Table 1). Most (e.g., greater than 80%) of the initial hits were subsequently eliminated by requiring inhibition of exoT-regulated bioluminescence at a level that was at least two-fold greater than inhibition of bioluminescence from the non-T3SS regulated lux *P. aeruginosa* strain MDM1156 (PAO-Lac/pUCP24GW-lacPO-lux-CDABE, see Table 1). The remaining compounds were evaluated for inhibition of T3SS-mediated secretion of an effector toxin-β-lactamase fusion protein (ExoS'-βLA) using *P. aeruginosa* strain MDM973 (PAK/pUCP24GW-lacI$^Q$-lacPO-exoS::blaM, Table 1). See, Examples 1 and 2, below for details of screening and validation of T3SS inhibitors.

Figure 8A:
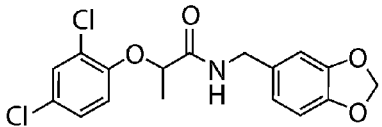
FIGS. 8A-8Q provide a summary catalog of structures and selected properties of MBX 1641 (re-synthesized compound 1) and 117 analogs that were characterized for T3SS inhibitory activity. The first five compounds listed in FIG. 8A were resynthesized and tested at Microbiotix, Inc. (Worcester, Mass.); these compounds are identified by MBX-numbers. The rest of the compounds appearing in FIGS. 8A-8Q were ordered from ChemBridge Corporation (San Diego, Calif.); each of these compounds is identified by the ChemBridge catalog designation. The ChemBridge compounds are listed in descending order of determined percentage T3SS inhibition in the exoT-lux primary reporter screen described herein; $IC_{50}$ (μM) values for inhibition of T3SS-mediated secretion of ExoS effector were also determined for some compounds using the ExoS'-βLA fusion protein secretion assay described herein. Compounds discovered to have an average percentage T3SS inhibition of 15% or greater (for example, ≥15% inhibition of exoT-lux at 50 μM as shown in this figure) and/or an $IC_{50}$ value of 100 μM or less (for example, $IC_{50}$≤100 μM in the ExoS'-βLA secretion assay as shown in this figure) are considered specific T3SS inhibitors of this invention.
Figure 8A:
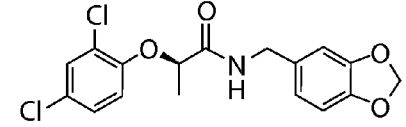
Figure 8A:
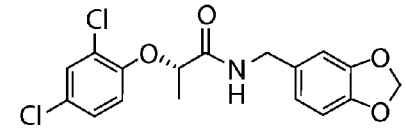
Figure 8A:
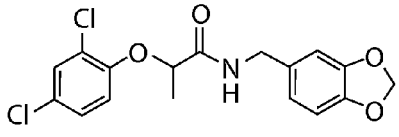
Figure 8A:
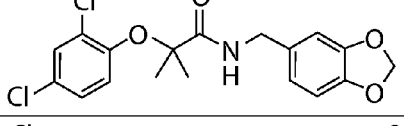
Figure 8A:
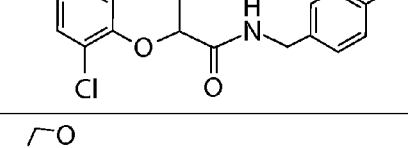
Figure 8A:
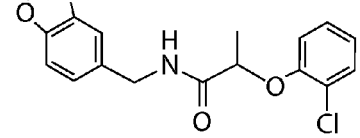
Figure 8H:
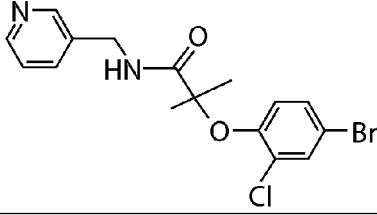
Figure 8H:
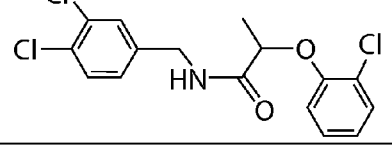
Figure 8H:
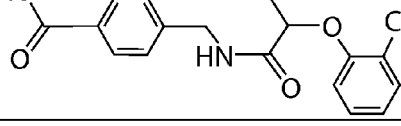
Figure 8H:
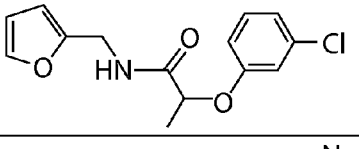
Figure 8H:
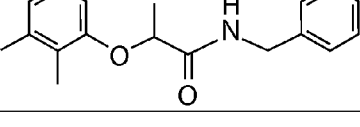
Figure 8H:
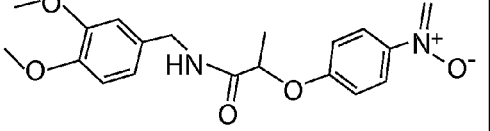
Figure 8H:
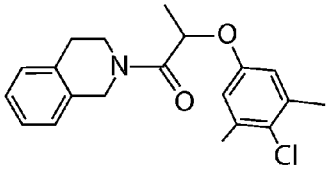
Figure 8I:
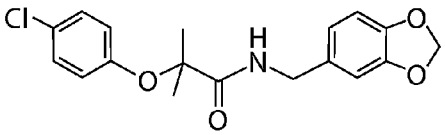
Figure 8I:
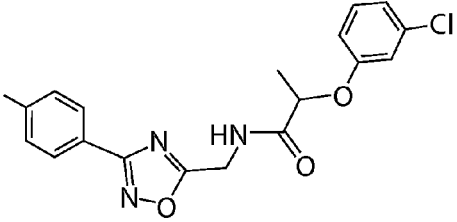
Figure 8I:
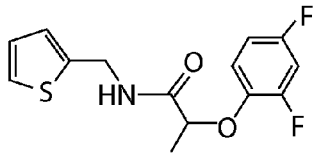
Figure 8I:
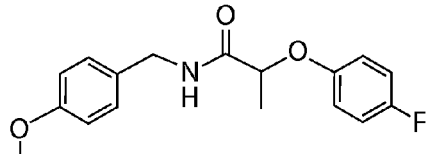
Figure 8I:
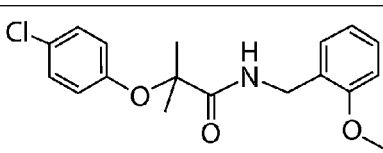
Figure 8I:
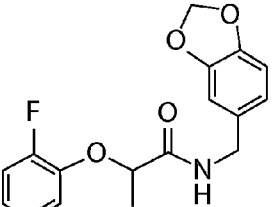
Figure 8L:
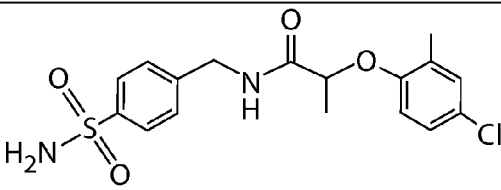
Figure 8L:
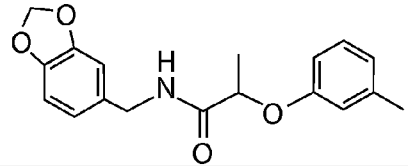
Figure 8L:
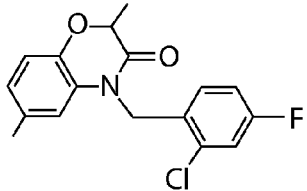
Figure 8L:
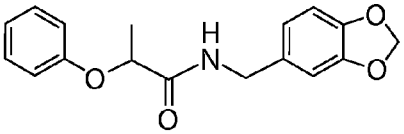
Figure 8L:
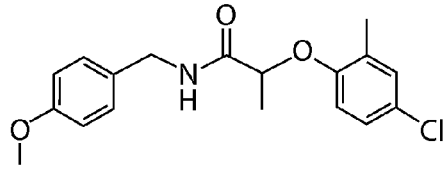
Figure 8L:
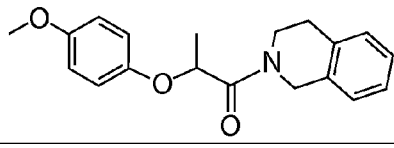
Figure 8L:
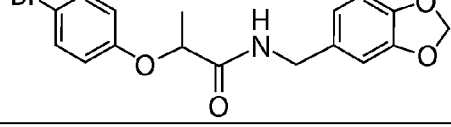

A bacterial T3SS inhibitor compound useful in the compositions and methods of the invention has a structure of a compound in any of Table 3, Table 5, and FIG. 8A, 8B, or 8C. The compounds preferably have an $IC_{50}$ less than 100 µM, preferably less than 25 µM, as measured in an assay for T3SS-mediated secretion of an effector toxin, e.g., such as by performing the ExoS'-β-lactamase fusion protein (ExoS'-βLA) assay described in the examples, infra, using *P. aeruginosa* strain MDM973 (PAK/pUCP24GW-lacI$^Q$-lacPO-exoS::blaM) as shown in Table 1 or comparable assay. Compounds with $IC_{50}$ greater than 100 µM are not generally useful as T3SS inhibitors in the compositions and methods described herein for administration to humans and other animals.

A T3SS inhibitor compound that is particularly useful in the compositions and methods described herein has an $IC_{50}$ of less than 100 µM as measured in an assay for T3SS-mediated secretion of an effector toxin-β-lactamase fusion protein (ExoS'-βLA) using *P. aeruginosa* strain MDM973 (PAK/pUCP24GW-lacI$^Q$-lacPO-exoS::blaM) described herein or a comparable assay and also has a relatively low cytotoxicity toward human cells, such as a $CC_{50}$ value of greater than or equal to 100 µM as measured in a standard cytotoxicity assay as described herein or as employed in the pharmaceutical field for antibiotics. Such standard cytotoxocity assays may employ Chinese hamster ovary (CHO) cells, HeLa cells, Hep-2 cells, human embryonic kidney (HEK) 293 cells, 293T cells, or other standard mammalian cell lines (61, 62).

The T3SS is the major virulence factor contributing to the establishment and dissemination of many acute bacterial infections but, with the possible exception of *Chlamydia* spp., does not appear to be essential for development or growth of the bacterial cells. Preferably, a T3SS inhibitor compound for use in compositions and methods of the invention also has a minimal inhibitory concentration (MIC) that is sufficiently high as to indicate that the inhibitor is not promiscuous but acts specifically on T3SS. Accordingly, a preferred T3SS inhibitor compound or combination of T3SS inhibitor compounds described herein is particularly useful as a supporting or adjunctive therapy for the treatment of bacterial infections in an individual (e.g., human or other animal). For example, a T3SS inhibitor compound may be administered to inhibit the T3SS of infecting bacterial cells, and another active agent, such as an antibiotic, may also be administered to inhibit growth of the infecting or potentially infecting bacterial cells in the individual. In an alternative treatment, a T3SS inhibitor compound may be administered to an individual to inhibit the T3SS of infecting or potentially infecting bacterial cells and thereby support or enable the individual's own immune system to more effectively kill and/or clear infecting bacteria from the tissues of the individual.

A particularly preferred T3SS inhibitor compound described herein is a phenoxyacetamide inhibitor that blocks T3SS-mediated secretion and translocation of one or more toxin effectors from cells of *P. aeruginosa*. Such a phenoxyacetamide T3SS inhibitor was identified as compound 1 in Table 3 and as MBX 1641 in FIG. 8A. MBX 1641 is a racemic mixture. The R-isomer of MBX 1641, designated "MBX 1684" (FIG. 8A) is an even more potent inhibitor of T3SS than the racemate. In contrast, the S-isomer, designated "MBX 1686" (FIG. 8A) is considerably less active, having an $IC_{50}$ greater than 100 µM, and thus is not preferred for use in compositions and methods of the invention. See, Table 4 and FIG. 8A.

A T3SS inhibitor compound useful in the compositions and methods includes a compound selected from MBX 1641 (compound 1) (see, e.g., Table 3, Table 4, FIG. 8), MBX 1684 (R-isomer of MBX 1641) (see, e.g., Table 3, Table 4, FIG. 8), compound 3 (see, e.g., Table 3), compound 4 (see, e.g., Table 3), compound 5685325 (see, e.g., Table 4, FIG. 8), compound 6380194 (see, e.g., Table 4, FIG. 8), compound 6430631 (see, Table 5), compound 7247834 (see, Table 5), compound F5054-0019 (see, Table 5) and combinations thereof.

Compositions and Methods

The T3SS inhibitor compounds described herein are organic compounds that can be ordered from suppliers such as ChemBridge Corporation (San Diego, Calif., USA), Life Chemicals Inc. (Burlington, ON, Canada) and Timtec LLC (Newark, Del., USA). T3SS inhibitor compounds as described herein may also be synthesized using established chemistries, and suitable synthesis schemes for the compounds disclosed herein are discussed in Examples 12-14. Most of the compounds described herein are produced or obtained as racemic mixtures of stereoisomers. As is demonstrated herein for compound 1 (MBX 1641, FIG. 8A), racemates may be resolved to separate optical isomers, and one of the isomers may prove to be inactive as a T3SS inhibitor. See, Example 12. We demonstrated that the R-stereoisomer of the MBX 1641 racemate (i.e., compound MBX 1648, FIG. 8A) was active as a T3SS inhibitor whereas the S-isomer was not. While we have determined that MBX 1648 is an active isomer, the resolution of any racemic T3SS inhibitor compounds disclosed herein into its component isomers, and determination of whether one or both of the optical isomers is an active inhibitor, will be a matter of routine for those skilled in the art. Therefore, reference to inhibitory racemates herein is also a disclosure of the active isomers having the same chemical structure, which may be confirmed by routine experimentation.

Unless otherwise indicated, it is understood that description of the use of a T3SS inhibitor compound in a composition or method also encompasses the embodiment wherein a combination of two or more T3SS inhibitor compounds are employed as the source of T3SS inhibitory activity in a composition or method of the invention.

Pharmaceutical compositions according to the invention comprise a T3SS inhibitor compound as described herein, or a pharmaceutically acceptable salt thereof, as the "active ingredient" and a pharmaceutically acceptable carrier (or "vehicle"), which may be a liquid, solid, or semi-solid compound. By "pharmaceutically acceptable" is meant that a compound or composition is not biologically, chemically, or in any other way, incompatible with body chemistry and metabolism and also does not adversely affect the T3SS inhibitor or any other component that may be present in a composition in such a way that would compromise the desired therapeutic and/or preventative benefit to a patient. Pharmaceutically acceptable carriers useful in the invention include those that are known in the art of preparation of pharmaceutical compositions and include, without limitation, water, physiological pH buffers, physiologically compatible salt solutions (e.g., phosphate buffered saline), and isotonic solutions. Pharmaceutical compositions of the invention may also comprise one or more excipients, i.e., compounds or compositions that contribute or enhance a desirable property in a composition other than the active ingredient.

Various aspects of formulating pharmaceutical compositions, including examples of various excipients, dosages, dosage forms, modes of administration, and the like are known to those skilled in the art of pharmaceutical compositions and also available in standard pharmaceutical texts, such as *Remington's Pharmaceutical Sciences,* 18th edition, Alfonso R. Gennaro, ed. (Mack Publishing Co., Easton, Pa. 1990), *Remington: The Science and Practice of Pharmacy, Volumes* 1 & 2, 19th edition, Alfonso R. Gennaro, ed., (Mack Publishing Co., Easton, Pa. 1995), or other standard texts on preparation of pharmaceutical compositions.

Pharmaceutical compositions may be in any of a variety of dosage forms particularly suited for an intended mode of administration. Such dosage forms, include, but are not limited to, aqueous solutions, suspensions, syrups, elixirs, tablets, lozenges, pills, capsules, powders, films, suppositories, and powders, including inhalable formulations. Preferably, the pharmaceutical composition is in a unit dosage form suitable for single administration of a precise dosage, which may be a fraction or a multiple of a dose that is calculated to produce effective inhibition of T3SS.

A composition comprising a T3SS inhibitor compound (or combination of T3SS inhibitors) described herein may optionally possess a second active ingredient (also referred to as "second agent", "second active agent") that provides one or more other desirable therapeutic or prophylactic activities other than T3SS inhibitory activity. Such a second agent useful in compositions of the invention includes, but is not limited to, an antibiotic, an antibody, an antiviral agent, an anticancer agent, an analgesic (e.g., a non-steroidal anti-inflammatory drug (NSAID), acetaminophen, an opioid, a COX-2 inhibitor), an immunostimulatory agent (e.g., a cytokine or a synthetic immunostimulatory organic molecule), a hormone (natural, synthetic, or semi-synthetic), a central nervous system (CNS) stimulant, an antiemetic agent, an antihistamine, an erythropoietin, a complement stimulating agent, a sedative, a muscle relaxant agent, an anesthetic agent, an anticonvulsive agent, an antidepressant, an antipsychotic agent, and combinations thereof.

Pharmaceutical compositions as described herein may be administered to humans and other animals in a manner similar to that used for other known therapeutic or prophylactic agents, and particularly as used for therapeutic aromatic or multi-ring antibiotics. The dosage to be administered to an individual and the mode of administration will depend on a variety of factors including age, weight, sex, condition of the patient, and genetic factors, and will ultimately be decided by an attending qualified healthcare provider.

Pharmaceutically acceptable salts of T3SS inhibitor compounds described herein include those derived from pharmaceutically acceptable inorganic and organic acids and bases. Examples of suitable acids include hydrochloric, hydrobromic, sulfuric, nitric, perchloric, fumaric, maleic, malic, pamoic, phosphoric, glycolic, lactic, salicylic, succinic, toluene-p-sulfonic, tartaric, acetic, citric, methanesulfonic, formic, benzoic, malonic, naphthalene-2-sulfonic, tannic, carboxymethyl cellulose, polylactic, polyglycolic, and benzenesulfonic acids.

The invention may also envision the "quaternization" of any basic nitrogen-containing groups of a compound described herein, provided such quaternization does not destroy the ability of the compound to inhibit T3SS. Such quaternization may be especially desirable to enhance solubility. Any basic nitrogen can be quaternized with any of a variety of compounds, including but not limited to, lower (e.g., $C_1$-$C_4$) alkyl halides (e.g., methyl, ethyl, propyl and butyl chloride, bromides, and iodides); dialkyl sulfates (e.g., dimethyl, diethyl, dibutyl and diamyl sulfates); long chain halides (e.g., decyl, lauryl, myristyl and stearyl chlorides, bromides and iodides); and aralkyl halides (e.g., benzyl and phenethyl bromides).

For solid compositions, conventional nontoxic solid carriers may be used including, but not limited to, mannitol, lactose, starch, magnesium stearate, sodium saccharin, talc, cellulose, glucose, sucrose, and magnesium carbonate.

Pharmaceutical compositions may be formulated for administration to a patient by any of a variety of parenteral and non-parenteral routes or modes. Such routes include, without limitation, intravenous, intramuscular, intra-articular, intraperitoneal, intracranial, paravertebral, periarticular, periostal, subcutaneous, intracutaneous, intrasynovial, intrasternal, intrathecal, intralesional, intratracheal, sublingual, pulmonary, topical, rectal, nasal, buccal, vaginal, or via an implanted reservoir. Implanted reservoirs may function by mechanical, osmotic, or other means. Generally and particularly when administration is via an intravenous, intra-arterial, or intramuscular route, a pharmaceutical composition may be given as a bolus, as two or more doses separated in time, or as a constant or non-linear flow infusion.

A pharmaceutical composition may be in the form of a sterile injectable preparation, e.g., as a sterile injectable aqueous solution or an oleaginous suspension. Such preparations may be formulated according to techniques known in the art using suitable dispersing or wetting agents (e.g., polyoxyethylene 20 sorbitan monooleate (also referred to as "polysorbate 80"); TWEEN® 80, ICI Americas, Inc., Bridgewater, N.J.) and suspending agents. Among the acceptable vehicles and solvents that may be employed for injectable formulations are mannitol, water, Ringer's solution, isotonic sodium chloride solution, and a 1,3-butanediol solution. In addition, sterile, fixed oils may be conventionally employed as a solvent or suspending medium. For this purpose, a bland fixed oil may be employed including synthetic mono- or diglycerides. Fatty acids, such as oleic acid and its glyceride derivatives are useful in the preparation of injectables, as are natural pharmaceutically-acceptable oils, including olive oil or castor oil, especially in their polyoxyethylated versions.

A T3SS inhibitor described herein may be formulated in any of a variety of orally administrable dosage forms including, but not limited to, capsules, tablets, caplets, pills, films, aqueous solutions, oleaginous suspensions, syrups, or elixirs. In the case of tablets for oral use, carriers, which are commonly used include lactose and corn starch. Lubricating agents, such as magnesium stearate, are also typically added. For oral administration in a capsule form, useful diluents include lactose and dried cornstarch. Capsules, tablets, pills, films, lozenges, and caplets may be formulated for delayed or sustained release.

Tablets and other solid or semi-solid formulations may be prepared that rapidly disintegrate or dissolve in an individual's mouth. Such rapid disintegration or rapid dissolving formulations may eliminate or greatly reduce the use of exogenous water as a swallowing aid. Furthermore, rapid disintegration or rapid dissolve formulations are also particularly useful in treating individuals with swallowing difficulties. For such formulations, a small volume of saliva is usually sufficient to result in tablet disintegration in the oral cavity. The active ingredient (a T3SS inhibitor described herein) can then be absorbed partially or entirely into the circulation from blood vessels underlying the oral mucosa (e.g., sublingual and/or buccal mucosa), or it can be swallowed as a solution to be absorbed from the gastrointestinal tract.

When aqueous suspensions are to be administered orally, whether for absorption by the oral mucosa or absorption via the gut (stomach and intestines), a composition comprising a T3SS inhibitor may be advantageously combined with emulsifying and/or suspending agents. Such compositions may be in the form of a liquid, dissolvable film, dissolvable solid (e.g., lozenge), or semi-solid (chewable and digestible). If desired, such orally administrable compositions may also contain one or more other excipients, such as a sweetener, a flavoring agent, a taste-masking agent, a coloring agent, and combinations thereof.

The pharmaceutical compositions comprising a T3SS inhibitor as described herein may also be formulated as suppositories for vaginal or rectal administration. Such compositions can be prepared by mixing a T3SS inhibitor compound as described herein with a suitable, non-irritating excipient that is solid at room temperature but liquid at body temperature and, therefore, will melt in the appropriate body space to release the T3SS inhibitor and any other desired component of the composition. Excipients that are particularly useful in such compositions include, but are not limited to, cocoa butter, beeswax, and polyethylene glycols.

Topical administration of a T3SS inhibitor may be useful when the desired treatment involves areas or organs accessible by topical application, such as the epidermis, surface wounds, or areas made accessible during surgery. Carriers for topical administration of a T3SS inhibitor described herein include, but are not limited to, mineral oil, liquid petroleum, white petroleum, propylene glycol, polyoxyethylene polyoxypropylene compounds, emulsifying wax, and water. Alternatively, a topical composition comprising a T3SS inhibitor as described herein may be formulated with a suitable lotion or cream that contains the inhibitor suspended or dissolved in a suitable carrier to promote absorption of the inhibitor by the upper dermal layers without significant penetration to the lower dermal layers and underlying vasculature. Carriers that are particularly suited for topical administration include, but are not limited to, mineral oil, sorbitan monostearate, polysorbate 60, cetyl esters wax, cetearyl alcohol, 2-octyl-dodecanol, benzyl alcohol, and water. A T3SS inhibitor may also be formulated for topical application as a jelly, gel, or emollient. Topical administration may also be accomplished via a dermal patch.

Persons skilled in the field of topical and transdermal formulations are aware that selection and formulation of various ingredients, such as absorption enhancers, emollients, and other agents, can provide a composition that is particularly suited for topical administration (i.e., staying predominantly on the surface or upper dermal layers with minimal or no absorption by lower dermal layers and underlying vasculature) or transdermal administration (absorption across the upper dermal layers and penetrating to the lower dermal layers and underlying vasculature).

Pharmaceutical compositions comprising a T3SS inhibitor as described herein may be formulated for nasal administrations, in which case absorption may occur via the mucous membranes of the nasal passages or the lungs. Such modes of administration typically require that the composition be provided in the form of a powder, solution, or liquid suspension, which is then mixed with a gas (e.g., air, oxygen, nitrogen, or a combination thereof) so as to generate an aerosol or suspension of droplets or particles. Inhalable powder compositions preferably employ a low or non-irritating powder carrier, such as melezitose (melicitose). Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. A pharmaceutical composition comprising a T3SS inhibitor described herein for administration via the nasal passages or lungs may be particularly effective in treating lung infections, such as hospital-acquired pneumonia (HAP).

Pharmaceutical compositions described herein may be packaged in a variety of ways appropriate to the dosage form and mode of administration. These include but are not limited to vials, bottles, cans, packets, ampoules, cartons, flexible containers, inhalers, and nebulizers. Such compositions may be packaged for single or multiple administrations from the same container. Kits may be provided comprising a composition, preferably as a dry powder or lyophilized form, comprising a T3SS inhibitor and preferably an appropriate diluent, which is combined with the dry or lyophilized composition shortly before administration as explained in the accompanying instructions of use. Pharmaceutical composition may also be packaged in single use pre-filled syringes or in cartridges for auto-injectors and needleless jet injectors. Multi-use packaging may require the addition of antimicrobial agents such as phenol, benzyl alcohol, meta-cresol, methyl paraben, propyl paraben, benzalconium chloride, and benzethonium chloride, at concentrations that will prevent the growth of bacteria, fungi, and the like, but that are non-toxic when administered to a patient.

Consistent with good manufacturing practices, which are in current use in the pharmaceutical industry and which are well known to the skilled practitioner, all components contacting or comprising a pharmaceutical composition must be sterile and periodically tested for sterility in accordance with industry norms. Methods for sterilization include ultrafiltration, autoclaving, dry and wet heating, exposure to gases such as ethylene oxide, exposure to liquids, such as oxidizing agents, including sodium hypochlorite (bleach), exposure to high energy electromagnetic radiation (e.g., ultraviolet light, x-rays, gamma rays, ionizing radiation). Choice of method of sterilization will be made by the skilled practitioner with the goal of effecting the most efficient sterilization that does not significantly alter a desired biological function of the T3SS inhibitor or other component of the composition.

Additional embodiments and features of the invention will be apparent from the following non-limiting examples.

EXAMPLES

Example 1

Materials and Methods for Identification and Characterization of T3SS Inhibitors Strains, Plasmids, and Growth Media Bacterial strains and plasmids used for assays are described in Table 1, below. All *P. aeruginosa* strains were derivatives of PAO1 (21), PAK (1), or PA14 (45). *E. coli* TOP10 (Invitrogen), *E. coli* DB3.1 (GATEWAY® host, Invitrogen), *E. coli* SM10 (7), and *E. coli* S17-1 (ATCC 47055) were used as hosts for molecular cloning. Luria-Bertani (LB) medium (liquid and agar) was purchased from Difco. LB was supplemented with 30 µg/ml gentamicin (LBG) with or without 1 mM isopropyl-β-D-thiogalactopyranoside (IPTG) and 5 mM EGTA (LBGI and LBGIE, respectively).

TABLE 1

Strains and Plasmids

| Strain | Genotype/Features | Reference or Source |
|---|---|---|
| *P. aeruginosa*: | | |
| MDM852 | PAO1::pGSV3-'exoT'-luxCDABE | This study |
| MDM1355 | PAO1 ΔpscC::pGSV3-'exoT'-luxCDABE | This study |
| MDM973 | PAK/pUCP24GW-lacI$^Q$-lacPO-exoS::blaM | This study |
| MDM974 | PAK ΔpscC/pUCP24GW-lacI$^Q$-lacPO-exoS::blaM | This study |
| MDM1156 | PAO-LAC/pUCP24GW-lacPO-luxCDABE | This study |
| PAKΔC | PAK ΔpscC; T3SS defective | (28) |
| PAKΔS | PAK ΔexoS; secretes ExoT as its only cytotoxic T3SS effector | (28) |

TABLE 1-continued

Strains and Plasmids

| Strain | Genotype/Features | Reference or Source |
|---|---|---|
| PAKΔSTYexoU | PAK ΔexoS::miniCTX-exoU-spcU; secretes ExoU as its only cytotoxic T3SS effector | (28) |
| PAKΔTY | PAK ΔexoT ΔexoY; secretes ExoS as its only T3SS effector | (28) |
| MDM1387 | PA14 xcpQ::MrT7; (aka, PAMr_nr_mas_02_2:H7) defective in type II secretion | (29) |
| *Y. pestis*: | | |
| JG153/pMM85 | KIM Δpgm pPCP1⁻ pCD1⁺/pHSG576 yopE::blaM | (31, 44) |

The *Y. pestis* reporter strain was kindly provided by Dr. Jon Goguen (U. Massachusetts Medical School). Plasmid pGSV3-Lux was kindly provided by Dr. Donald Woods (U. Calgary).

PCR and Primers.

Synthetic oligonucleotide primers (from Operon, Inc.) were designed using the published genome sequence for *P. aeruginosa* (53) and web-based PRIMER3 (Whitehead Institute) (Table 2). Primers were used at 10 µM in PCR amplifications with FAILSAFE® polymerase (Epicentre), Buffer G (Epicentre), and 4% DMSO for *P. aeruginosa* chromosomal DNA templates.

TABLE 2

Primers Used

| # | Primer Name | Primer Sequence |
|---|---|---|
| 1 | exoT-F + EcoRI | TACTACGAATTCCCAGGAAGCACCGAAGG (SEQ ID NO: 1) |
| 2 | exoT-R + EcoRI | CATTACGAATTCCTGGTACTCGCCGTTGGTAT (SEQ ID NO: 2) |
| 3 | exoT-out-F | TAGGGAAAGTCCGCTGTTTT (SEQ ID NO: 3) |
| 4 | luxC-R | CCTGAGGTAGCCATTCATCC (SEQ ID NO: 4) |
| 5 | exoS-F + GWL | TACAAAAAAGCAGGCTAGGAAACAGACATGCATATTCAATCG CTTCAG (SEQ ID NO: 5) |
| 6 | exoS(234)-R | ATCTTTTACTTTCACCAGCGTTTCTGGGTGACCGTCGGCCGATA CTCTGCT (SEQ ID NO: 6) |
| 7 | BLA-F | CACCCAGAAACGCTGGTGAA (SEQ ID NO: 7) |
| 8 | BLA-R + GWR | TACAAGAAAGCTGGGTTTGGTCTGACAGTTACCAATGC (SEQ ID NO: 8) |
| 9 | GW-attB1 | GGGGACAAGTTTGTACAAAAAAGCAGGCT (SEQ ID NO: 9) |
| 10 | GW-attB2 | GGGGACCACTTTGTACAAGAAAGCTGGGT (SEQ ID NO: 10) |
| 11 | lux-F + GWL | TACAAAAAAGCAGGCTAGGAAACAGCTATGACGAAGAAGATC AGTTTTATAATTAACGGCCAGGTTGAAATC (SEQ ID NO: 11) |
| 12 | lux-R + GWR | TACAAGAAAGCTGGGTGTTTTCCCAGTCACGACGTT (SEQ ID NO: 12) |

Screening Compounds.

Compounds screened in this study were purchased from ChemBridge (San Diego, Calif.) and Timtec (Newark, Del.), diluted in 96-well master plates at 2.5 mM in DMSO, and stored at −20° C.

Luciferase Transcriptional Reporter Screen.

A transcriptional fusion of the *Photorhabdus luminescens* lux operon (luxCDABE) to effector gene exoT (PA0044) was constructed by inserting an internal fragment of the exoT gene (712 bp generated by PCR with primers exoT-F+EcoRI/exoT-R+EcoRI, Table 2, above) into EcoRI-cut reporter plasmid pGSV3-lux-Gm (37) as described previously (35). The resulting plasmid was introduced into *E. coli* SM10 cells and transferred into *P. aeruginosa* PAO1 and PAO1 ΔpscC cells by conjugation (35) to generate recombinant reporter strains MDM852 and MDM1355, respectively. Insertion at the exoT chromosomal locus was confirmed by PCR with a primer outside of the cloned locus (exoT-out-F) and a primer within the luxC gene (luxC-R) (Table 2, above).

Figure 1B:
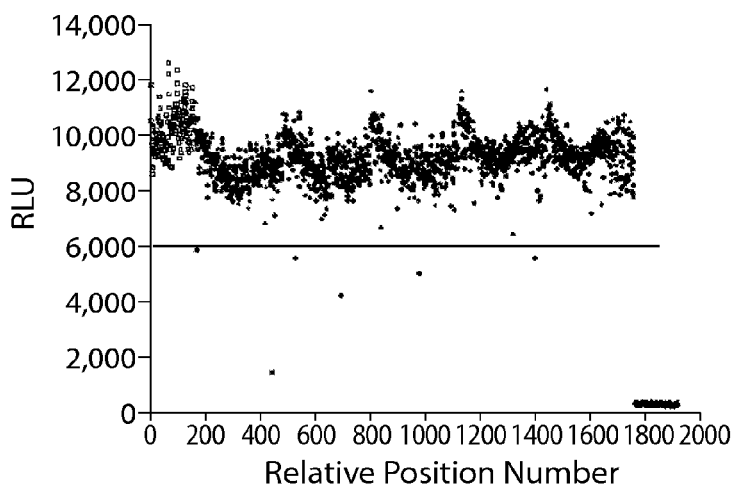
FIG. 1B shows luminescence (RLU) from five 384-well microplates containing reporter strain MDM852 in a high throughput screen for T3SS inhibitors. RLU values are shown at 200 minutes for 160 negative controls (white squares, □, fully induced by EGTA) in positions 1-160, for 160 positive controls (black triangles, ▲, no induction by EGTA) in positions 1,761-1,920, and for 1,600 samples (black circles, ●) in positions 161-1,760. Six samples were designated as hits because their RLU values displayed z-scores >4 (i.e., >4 standard deviations below the average sample value, denoted as a horizontal line at 6,084 RLU). Compound 1 at position 443 was the most potent hit (z–score=10). See, Example 2 for details.

For inhibitor screening, compound master plates were thawed at room temperature on the day of the screen, and 1 µl of compound (final 45 µM compound and 1.8% DMSO) was added to the 384-well opaque black screening plates using a Sciclone ALH 3000 liquid handling robot (Caliper, Inc.) and a Twister II Microplate Handler (Caliper, Inc.). Reporter strain MDM852 was grown at 37° C. in LBGI to $OD_{600}$~0.025-0.05, transferred into microplates (50 µl/well) containing test compounds and EGTA (5 µl of 0.1M stock solution), which were covered with a translucent gas-permeable seal (Abgene, Inc., Cat. No. AB-0718). Control wells contained cells with fully induced T3SS (EGTA and DMSO, columns 1 and 2) and uninduced T3SS (DMSO only, columns 23 and 24). Plates were incubated at room temperature for 300 min. Then, luminescence was measured in an Envision Multilabel microplate reader (PerkinElmer) (FIGS. 1A and 1B). The screening window coefficient, Z'-factor (60), defined as the ratio of the positive and negative control separation band to the signal dynamic range of the assay, averaged 0.7 for the screen. All screening data, including the z-score, and confirmation and validation data were stored in one central database (CambridgeSoft's ChemOffice 11.0). Validated hits were re-ordered from the vendor and confirmed to be >95% pure and to be of the expected mass by LC-MS analysis. Compounds for SAR analysis were ordered from ChemBridge Corporation (San Diego, Calif.).

Effector-β-Lactamase (βLA) Secretion Assays.

Figure 1C:
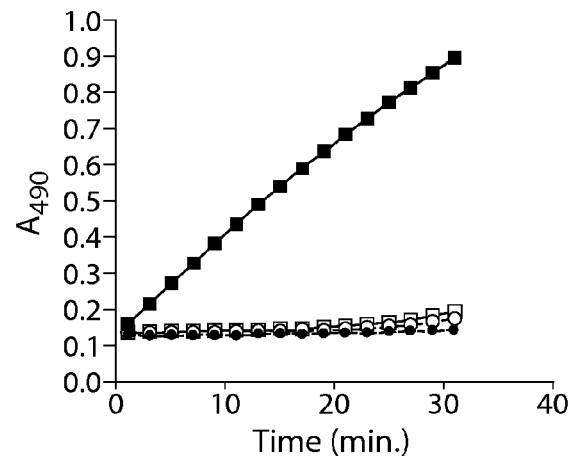
FIG. 1C shows detection of secretion of the effector toxin-β-lactamase fusion protein ExoS'-βLA from *P. aeruginosa* strains MDM973 (PAK) and MDM974 (PAK ΔpscC) carrying pUCP24GW-lacI$^Q$-lacP$^Q$-exoS'-blaM, as measured by hydrolysis of nitrocefin. $A_{490}$ values are plotted vs. time for MDM973 in the presence (black squares, ■) and absence (white squares, □) of 5 mM EGTA and for strain MDM974 in the presence (black circles, ●) and absence (white circles, ○) of 5 mM EGTA. See, Example 2 for details.

(a) *P. aeruginosa*. A gene encoding an ExoS'-β-lactamase (βLA) fusion protein (comprised of 234 codons of *P. aeruginosa* effector ExoS fused to the TEM-1 β-lactamase gene lacking secretion signal codons) was constructed by splicing by overlap extension PCR(SOE-PCR) (4) using primers 5-10 (Table 2, above), sequence confirmed, cloned into lacI$^Q$-containing GATEWAY® vector pUCP24GW (36) behind the lac promoter, and introduced into *P. aeruginosa* by electroporation (3). Secretion of fusion proteins was detected by measuring the hydrolysis of the chromogenic β-lactamase substrate nitrocefin in clear 96-well microplates in a modification of a previously described assay (27). Cells of strain MDM973 (PAK/pUCP24GW-exoS::blaM) were sub-cultured in the morning from overnight growths in LBG into 0.1 ml of LBGIE with or without test compounds and grown for 150 min. Nitrocefin (100 µg/ml final) was added, and $A_{490}$ measurements taken every minute for 15 min in a Victor$^3$V 1420 Multilabel HTS Counter (PerkinElmer). Slopes were calculated as a relative measure of the quantity of the effector-βLA fusion protein secreted and were absolutely dependent on induction with IPTG, EGTA, and the presence of a functional pscC gene in the *P. aeruginosa* cells (FIG. 1C). Typical signal:background ratios were 6-10.

(b) *Yersinia pestis*. Attenuated *Y. pestis* strain JG 153 (gift of Jon Goguen, U. of Massachusetts Medical School, Worcester, Mass.) carrying plasmid pMM85 (yopE::blaM) was grown in LB+20 µg/ml chloramphenicol at 30° C. to prevent T3SS induction and loss of the pCD1 plasmid encoding T3SS. To induce T3SS, cells were shifted from 30° C. to 37° C. and EGTA was added to 1 mM final concentration. Cell culture (0.1 ml) was added to clear 96-well microplates containing test compound and incubated for 3 hours at 37° C. Nitrocefin was added (100 µg/ml final), and $A_{490}$ measurements were taken every minute for 10 minutes in an Envision Multilabel microplate reader (PerkinElmer). Slopes were plotted vs. the inhibitor concentration to determine $IC_{50}$ values.

Counter Screen for Inhibition of Bioluminescence of Lac-Promoted luxCDABE.

The complete *Photorhabdus luminescens* luxCDABE locus was amplified from pGSV3-lux (37) by PCR with Phusion polymerase (NEB, Beverly, Mass.) and primers lux-F+GWL and lux-R+GWR, followed by a second PCR with primers GW-attB1 and GW-attB2 to provide the full Gateway recognition sequence (Table 2). The ~5.8 kb product was gel-purified and inserted into pDONR221 with BPClonase® enzyme (Invitrogen), and then into pUCP24GW (36) with LRClonase® enzyme (Invitrogen). The resulting pUCP24GW-lacPO-luxCDABE plasmid was introduced into the *P. aeruginosa* PAO-LAC strain carrying one chromosomal copy of the lac repressor, lacI$^Q$, at the phiCTX locus (20) by electroporation, selecting for gentamicin-resistance (3). To measure the effects of T3SS inhibitors on lac-promoted luciferase production, the resulting strain MDM1156 was subcultured from overnight LBG growths into LBGI at an $A_{600}$-0.05 and grown for 3 h in the presence or absence of inhibitors at 50 µM. The percent inhibition by compounds of RLU produced by lac-promoted vs. exoT-promoted luciferase was calculated and used as an indication of the T3SS-selectivity of the screening hits.

Detection of Inhibition of T3SS-Mediated ExoS Secretion into Culture Broths

*P. aeruginosa* strain PAKΔTY, which produces the ExoS, but not the ExoT or ExoY T3SS effectors, was grown overnight in LB and treated essentially as described previously (28). Bacteria were subcultured 1:1,000 in LB supplemented with 5 mM EGTA and grown for 3 h at 37° C. with aeration in the presence or absence of inhibitors at the indicated concentrations. Bacteria were sedimented by centrifugation at 3,220×g for 15 min at 4° C. Culture supernatant was collected, and proteins were concentrated by precipitation with 12.5% trichloroacetic acid followed by washing with acetone or by ultrafiltration. Proteins were resuspended according to original culture density ($A_{600}$), separated by sodium dodecyl sulfate-polyacrylamide gel electrophoresis (12.5% SDS-PAGE), and stained with Coomassie blue. Stained gel image files were processed with ImageJ software (ver. 1.42q, NIH) by subtracting the background, inverting the image, and integrating the density of each band.

Inhibition of *P. Aeruginosa* ExoU-Dependent CHO Cell Killing.

Rescue of CHO cells from T3SS mediated cytotoxicity of translocated effector protein ExoU was measured using a lactate dehydrogenase (LDH) release assay as previously reported (28) except that infection with *P. aeruginosa* was carried out for 2 h in the absence of gentamicin. Percent cytotoxicity (% LDH release) was calculated relative to that of the uninfected control, which was set at 0% LDH release, and that of cells infected with *P. aeruginosa* unprotected by test compound (100% LDH release). LDH released from unprotected, infected cells reached at least 80% of the value obtained from complete lysis with 1% Triton X-100 in the 2 h timeframe of this experiment. Pseudolipasin, which acts by direct inhibition of the ExoU phospholipase, was used as control inhibitor (27).

Gentamicin Protection Assays of Bacterial Internalization.

Experiments were carried out using a modification of a previously published method (18). A total of 2×10$^5$ HeLa cells were seeded into each well of a 12-well plate containing 2 ml per well of MEM supplemented with 10% FCS and incubated at 37° C. in 5% of $CO_2$ for 24 h. After two washes with PBS, 1 ml of MEM containing 1% FCS was added to the HeLa cells. MBX 1641 was added to half the wells at 50 µM final concentration (DMSO at 0.2% final). *P. aeruginosa* strains PAKΔC (negative control) and PAKΔS (positive control) were grown overnight in LB medium at 37° C. with shaking, diluted 1:1,000 in the morning and grown to an $OD_{600}$ of 0.3 (~10$^8$ cells/ml). Bacteria were washed in PBS, resuspended in 1 ml of MEM, and added to the HeLa cells at an MOI of 10 in the presence or absence of MBX 1641. Infected HeLa cells were incubated at 37° C. in 5% $CO_2$ for 2 h. After two washes with PBS, 1 ml of MEM containing 50 µg/ml gentamicin was added, and cells were incubated for an additional 2 h. After three washes with PBS, the cells were lysed in PBS containing 0.25% Triton X-100, and dilutions were plated on LB-agar plates to count the number of bacteria internalized within HeLa cells.

Elastase Secretion Assay.

The effect of test compounds on type II-mediated secretion of elastase from *P. aeruginosa* was determined by a modification of a previously described method (42). *P. aeruginosa* PA14 cells were cultured from a starting density of $A_{600}$~0.05 for 16 h to saturation in LB in the presence or absence of test compound at 50 µM. Cells were removed by centrifugation in a microfuge, and 0.2 ml of cleared supernatant was added to 0.4 ml of a suspension of elastin-Congo Red (5 mg/ml, Sigma) in buffer consisting of 0.1M Tris-HCl, pH 7.4 and 1 mM $CaCl_2$ in capped microfuge tubes. Tubes were incubated at 37° C. with shaking for 6 h. Then, 0.4 ml of buffer consisting of 0.7 M sodium phosphate (pH 6.0) was added, tubes were centrifuged in a microfuge to remove undigested elastin-Congo Red, and $A_{495}$ of the cleared supernatants was measured. Readings were normalized to the original cell density ($OD_{600}$), and % inhibition of elastase secretion was determined relative to untreated PA14 (no inhibition control) and to untreated type II secretion defective PA14 xcpQ::MrT7 (29) (strain MDM1387, Table 1) (complete inhibition control).

*Chlamydia Trachomatis* Growth Inhibition Assay.

Inhibition of the growth of *Chlamydia trachomatis* L2 strain by compounds was measured in 24-well plates essentially according to the method of Wolf et al. (59). Confluent monolayer Hep-2 cells were infected with L2 at an MOI of 0.5 and treated with compounds at indicated concentrations for 48 h. Then cultures were collected and sonicated. Entire lysates were used for counting inclusion forming units (IFUs) as a measurement of production of *Chlamydia* progeny elementary bodies (EBs) by re-plating onto fresh HeLa monolayers. An uninhibited control (DMSO only) and a complete inhibition control (chloramphenicol, 200 µg/ml) were included. Experiments were done in triplicate.

Minimum Inhibitory Concentration (MIC).

MIC determination was done by the broth microdilution method described in the CLSI (formerly NCCLS) guidelines (39) and expressed in µM to facilitate comparisons with $IC_{50}$ and $CC_{50}$ values.

Determination of Mammalian Cytotoxicity.

The cytotoxic concentration ($CC_{50}$) of compound versus cultured mammalian cells (HeLa, ATCC CCL-2; American Type Culture Collection, Manassas, Va.) was determined as the concentration of compound that inhibits 50% of the conversion of MTS to formazan (32). Briefly, 96-well plates were seeded with HeLa cells at a density of $4 \times 10^3$ per well in VP-SFM medium without serum (14), in the presence or absence of serial dilutions of a compound dissolved in DMSO. Following incubation for 3 days at 37° C. in VP-SFM, cell viability was measured with the vital tetrazolium salt stain 3-(4,5-dimethylthiazol-2-yl)-2,5 diphenyltetrazolium bromide according to the manufacturer's instructions (Promega, Madison, Wis.). Values were determined in duplicate using dilutions of inhibitory compound from 100 µM to 0.2 µM.

Chemistry.

The organic compounds identified as T3SS inhibitors herein were obtained mainly from commercial sources. A series of phenoxyacetamide compounds was synthesized for closer study of compound 1 (Table 3), which was designated MBX 1641 when resynthesized by us. Additional phenoxyacetamides designated MBX1685, MBX1684, and MBX1686 (FIG. 8A), which are related to screening hit MBX 1641, were all prepared from 2,4-dichlorophenol. Alkylation of 2,4-dichlorophenol with ethyl 2-bromo-2-methylpropanoate ($K_2CO_3$, $CH_3CN$) provided ethyl 2-(2,4-dichlorophenoxy)-2-methylpropanoate, which was hydrolyzed (KOH, EtOH) and coupled (HOAT, EDCI, DMF, DIPEA) (2) with 3,4-methylenedioxybenzylamine to provide MBX1685. Mitsunobu coupling (34) of 2,4-dichlorophenol with (5)-ethyl 2-hydroxypropanoate ($PPh_3$, DIAD, THF) provided ethyl (R)-2-(2,4-dichlorophenoxy)propanoate, which was hydrolyzed ($LiOH$—$H_2O$, $CH_3CN$—$H_2O$) and then coupled as above with 3,4-methylenedioxybenzylamine to give MBX 1684. The corresponding S-enantiomer (MBX1686) was prepared in precisely the same fashion, but using methyl (R)-2-hydroxypropanoate with 2,4-dichlorophenol in the Mitsunobu coupling protocol. Hit compound MBX 1641 and the desmethyl analog compound MBX 1668 (FIG. 8A) were prepared directly from commercially available 2-(2,4-dichlorophenoxy)propanoic acid and 2,4-dichlorophenoxyacetic acid, respectively, by coupling with 3,4-methylenedioxybenzylamine as described above.

Additional details of synthesis and synthesis schemes for other classes of compounds disclosed herein are presented in Examples 12-14.

Example 2

Identification and Validation of Inhibitors of *P. aeruginosa* T3SS

A *P. aeruginosa* cell-based bioluminescent reporter screen (luciferase transcriptional reporter screen, described above) for the identification of T3SS inhibitors was constructed in an analogous fashion to that described previously in *Yersinia* (24). Due to tight coupling of T3SS gene regulation in *P. aeruginosa* with type III secretion of the negative regulator ExsE, reduced type III secretion capability results in decreased expression of all T3SS operons (47, 54). *P. aeruginosa* strains were constructed carrying a transcriptional fusion of the T3SS effector gene exoT to the luxCDABE operon of *Photorhabdus luminescens* and their luminescence production under T3SS-inducing and repressing conditions evaluated. When $Ca^{++}$ levels remain high, e.g., no EGTA addition (55), or a key component of the T3SS assembly is deleted, e.g., the pscC gene encoding the secreton component of T3SS (27), T3SS is not functional and luminescence is significantly reduced as compared to wild-type cells grown in low levels of free $Ca^{++}$ (addition of 5 mM EGTA) (see, FIG. 1A). The application of the wild-type transcriptional fusion strain was optimized for screening in 384-well microplates, and about 80,000 discrete chemical compounds were screened at 50 µM to identify inhibitors of T3SS. Screening results are shown graphically for five representative 384-well assay plates in FIG. 1B. The substantial signal-to-background ratio (>20) and the very modest coefficients of variation (standard deviation/average signal) for samples, positive, and negative controls (all <10%) are representative of those observed in the entire screen. A total of 331 compounds (0.4% of the library) were detected as primary hits due to inhibition of RLU values at least 4 standard deviations below the sample average (z-score ≥4; solid line in FIG. 1B), and over 60% of them (208 compounds) were confirmed as inhibitors when re-tested in the same assay in triplicate. However, over 80% of these putative inhibitors were eliminated by requiring that they inhibit luminescence from the exoT-lux screening strain >2-fold more potently than from a non-T3SS regulated lux strain (lac-regulated luxCDABE in strain MDM1156). The absence of T3SS-specificity observed for most screening hits is likely the result of the many non-T3SS related mechanisms capable of reducing luminescence (e.g., inhibition of growth, energy metabolism, transcription, or translation).

Validation of Inhibitors of *P. Aeruginosa* T3SS-Mediated Secretion.

The remaining T3SS-selective hits were evaluated directly for inhibition of T3SS-mediated secretion. Measurements were carried out using a cellular assay consisting of an effector-reporter fusion protein. Codons for the type III secretion signals (8) and the GAP domain of *P. aeruginosa* ExoS (17) were fused to the TEM1 β-lactamase gene lacking its secretion signal. The construct was cloned into the exogenously replicating plasmid pUCP24GW, resulting in the production of ExoS'-βLA fusion protein under lac regulation in *P. aeruginosa* cells. In this assay, secreted β-lactamase activity is detected by hydrolysis of the β-lactamase chromogenic substrate nitrocefin, resulting in increased $A_{490}$. Signal generation is dependent on the presence of EGTA and IPTG, and is eliminated in T3SS-defective ΔpscC mutant cells (FIG. 1C). Almost all (41 of 43) of the T3SS-selective inhibitors identified in the transcriptional fusion reporter assays also inhibited secretion of the effector-reporter fusion protein by at least 50% when added at a concentration of 50 μM during induction of T3SS and the effector fusion. No inhibition was observed when compounds were added after induction at the time of chromogenic substrate addition, indicating that the compounds inhibit the appearance of extracellular β-lactamase rather than β-lactamase catalysis itself.

Finally, the inhibitors were evaluated for potency of ExoS'-βLA fusion protein secretion inhibition ($IC_{50}$) and counter-screened for cytotoxicity ($CC_{50}$), yielding 5 additionally validated T3SS inhibitors with $IC_{50}$ values ≤25 μM and $CC_{50}$ values ≥100 μM (Table 3). These five inhibitors (compounds 1, 3, 4, 8, and 9) exhibited no detectable MIC (MIC>100 μM) vs. *P. aeruginosa*, and did not inhibit the growth rate of *P. aeruginosa* cells (data not shown), confirming that they are not reducing luminescence or β-lactamase secretion by inhibiting bacterial cell growth or viability. These five hypervalidated T3SS inhibitors can be categorized into three structural classes, indicated in Table 3 as series A (phenoxyacetamides, compound 1), B (malic diamides, compounds 3 and 4), and D (N-phenyl maleimide adducts, compounds 8 and 9).

TABLE 3

Validated T3SS Inhibitors.[†]

| Cpd. # | Series | Structure | RLU Selectivity[a] | Serum Effect[b] | ExoS'-βLA $IC_{50}$[c] | HeLa $CC_{50}$[d] | $CC_{50}$/ $IC_{50}$[e] | yopE-βLA $IC_{50}$[f] |
|---|---|---|---|---|---|---|---|---|
| 1 | A | 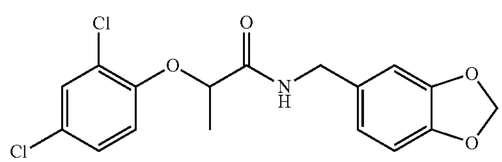 [SMILES: CC(Oc1ccc(Cl)cc1Cl)C(=O)NCc1ccc2c(c1)OCO2] | 7 | 3.7 | 12.5 | 102 | 8.1 | 22 |
| 2 | B | 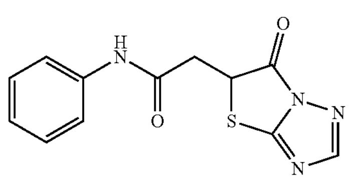 [SMILES: O=C(CC1Sc2ncnn2C1=O)Nc1ccccc1] | 2.6 | 2 | 12 | 37 | 3.1 | 6.1 |
| 3 | B | 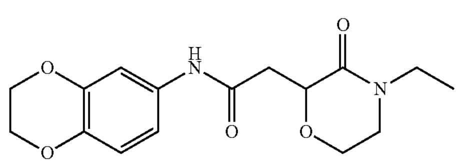 [SMILES: CCN1CCOC(CC(=O)Nc2ccc3c(c2)OCCO3)C1=O] | 4.1 | 4.8 | 20 | >100 | >5.0 | 16 |
| 4 | B | 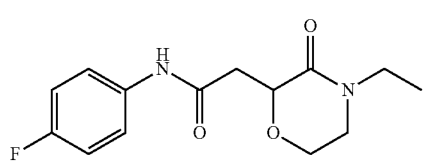 [SMILES: CCN1CCOC(CC(=O)Nc2ccc(F)cc2)C1=O] | 3.9 | 4.2 | 13 | 100 | 6.2 | 6 |
| 5 | C | 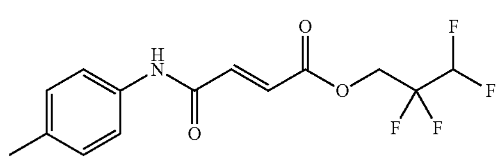 [SMILES: Cc1ccc(NC(=O)/C=C/C(=O)OCC(F)(F)C(F)F)cc1] | 4.5 | 2.6 | 22 | 28 | 1.3 | |
| 6 | C | 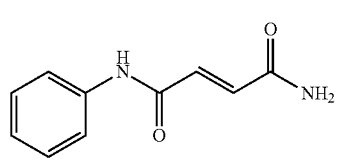 [SMILES: NC(=O)/C=C/C(=O)Nc1ccccc1] | 3.6 | 1.5 | 19 | 35 | 1.8 | |

TABLE 3-continued

Validated T3SS Inhibitors.[†]

| Cpd. # | Series | Structure | RLU Selectivity[a] | Serum Effect[b] | ExoS'-βLA IC$_{50}$[c] | HeLa CC$_{50}$[d] | CC$_{50}$/ IC$_{50}$[e] | yopE-βLA IC$_{50}$[f] |
|---|---|---|---|---|---|---|---|---|
| 7 | C | (2-chlorophenyl fumaramide structure) | 4.7 | 1.5 | 17 | 40 | 2.4 | |
| 8 | D | (oxanorbornene dicarboximide with 2,4-dimethylphenyl) | 9.2 | 3.1 | 15 | >100 | >6.7 | 103 |
| 9 | D | (oxanorbornene dicarboximide with 2-nitrophenyl) | 2.4 | 4.7 | 21 | >100 | >4.8 | 51 |
| 10 | n.a. | (pyrrolone with 4-nitrophenyl, thiophenyl, ethylbenzothiazole) | 3.8 | 1.8 | 3 | 16 | 5.3 | 4.1 |
| 11 | n.a. | (4-dimethylamino-phenyl thiocarbonyl N-methylpiperazine) | 22 | 1 | 19 | 18 | 0.9 | 19 |

[†]All IC$_{50}$ and CC$_{50}$ values are presented in μM units.
[a]% inhibition of exoT-lux RLU/% inhibition of lac-lux RLU, both at 50 μM compound.
[b]% inhibition of exoT-lux RLU in the absence of serum/% inhibition of exoT-lux RLU in the presence of 10% fetal calf serum, both at 50 μM compound.
[c]Compound concentration at which secretion of ExoS'-βLA fusion protein from P. aeruginosa strain MDM973 is reduced by 50%.
[d]Compound concentration at which the viability of HeLa cells cultured in serum-free medium is reduced by 50%.
[e]Selectivity of T3SS inhibition as measured by the ratio of potency of the compound in the HeLa cell viability assay vs the T3SS inhibition assay.
[f]Compound concentration at which secretion of YopE-βLA fusion protein from Y. pestis strain JG153/pMM85 is reduced by 50%.

Example 3

Inhibition of T3SS-Mediated Secretion of Native Effectors

Figure 2A:
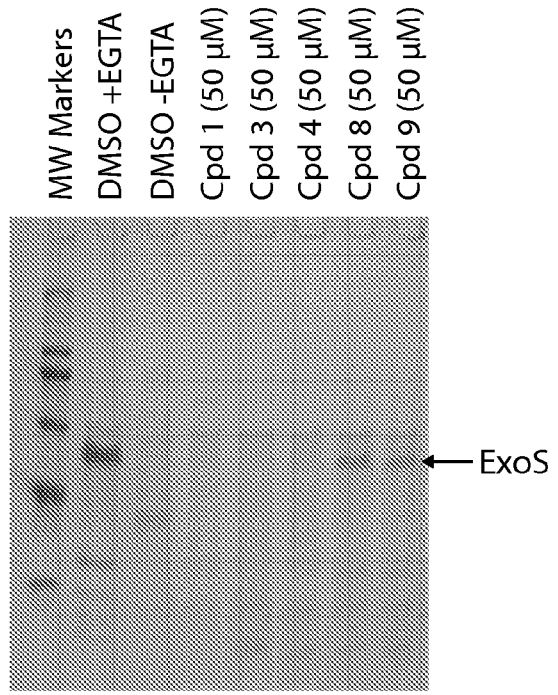
FIG. 2A shows analysis of secreted proteins from cells treated with EGTA and five validated T3SS inhibitors (compounds 1, 3, 4, 8, and 9 in Table 3). The band corresponding to 49K ExoS is marked by the arrow. See, Example 3 for details.

To confirm that inhibitors identified by the cell-based reporter assays inhibit T3SS-mediated secretion of natural effectors, conditioned culture media, obtained from *P. aeruginosa* PAKΔTY, an ExoS-secreting strain, exposed to each of the five T3SS inhibitors at 50 μM during growth for 3 hours under T3SS inducing conditions, were concentrated and the secreted effectors were visualized on SDS-PAGE (FIG. 2A). All five compounds inhibited the secretion of ExoS from *P. aeruginosa* cells by at least 75%. Compounds 1, 3, and 4 completely inhibited the secretion of ExoS (marked by an arrow in FIG. 2A) from *P. aeruginosa* PAKΔTY cells when present at 50 μM during T3SS induction. Compounds 8 and 9 reduced the amount of secreted effector significantly, but not completely at the 50 μM concentration.

Figure 2B:
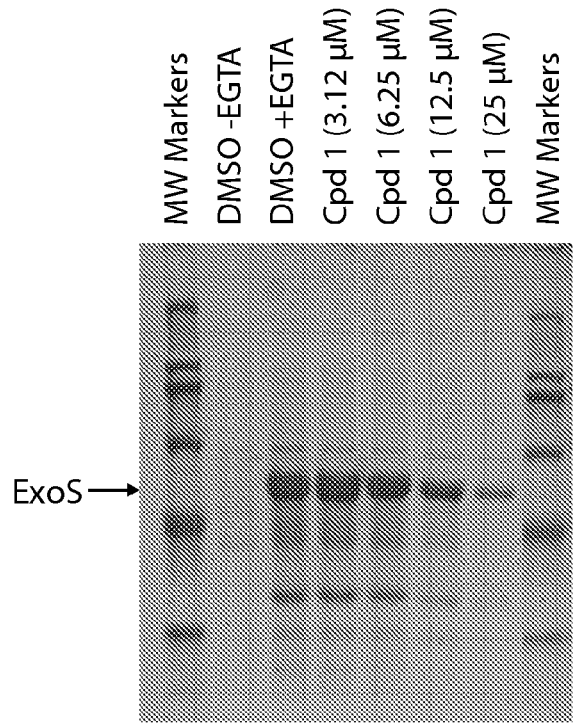
FIG. 2B shows an analysis of secreted proteins from cells treated with EGTA and serial dilutions of T3SS inhibitor compound 1. The band corresponding to 49K ExoS is marked by the arrow. See, Example 3 for details
Figure 2C:
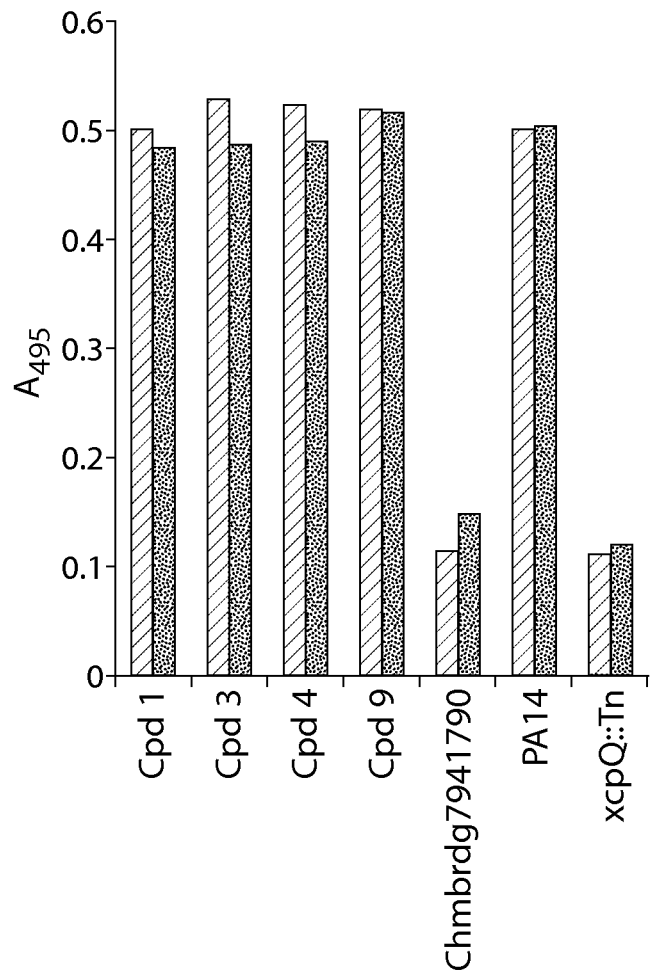
FIG. 2C shows the effects of T3SS inhibitors (compounds 1, 3, 4, and 9) on type II secretion of elastase. *P. aeruginosa* PA14 cells were grown in LB medium for 16 h in the presence of 50 μM of the indicated compounds. As controls, PA14 and PA14 xcpQ::Tn cells were grown in LB in the presence of the equivalent concentration of DMSO, and PA14 was grown in the presence of 50 μM of a type II secretion inhibitor (compound 7941790, ChemBridge Corporation). Culture medium corresponding to equivalent numbers of cells was harvested by centrifugation and incubated with shaking for 6 hours with Congo Red-elastin. Digested soluble Congo Red was measured by $A_{495}$ in two independent assays and plotted (grey and black bars). See, Example 3 for details.

The concentration-dependence of inhibition of native ExoS secretion was examined in detail for compound 1 and was found to be very similar to that observed in the ExoS'-βLA inhibition assay (IC$_{50}$ of ~12.5 μM) (FIG. 2B). The inhibitory effect appeared specific for type III secretion, since members of all three structural classes failed to inhibit type II-mediated elastase secretion when added to type II secretion-competent *P. aeruginosa* PA14 cells at 50 µM (FIG. 2C). Control inhibitor 7941790 (ChemBridge Corporation) reduced elastase secretion to the level observed in a type II deficient PA14 strain carrying a transposon insertion in the secreton gene xcpQ while the three series of T3SS inhibitors had no detectable effect.

Example 4

Inhibition of T3SS-Mediated Effects on Mammalian Cells

Figure 3A:
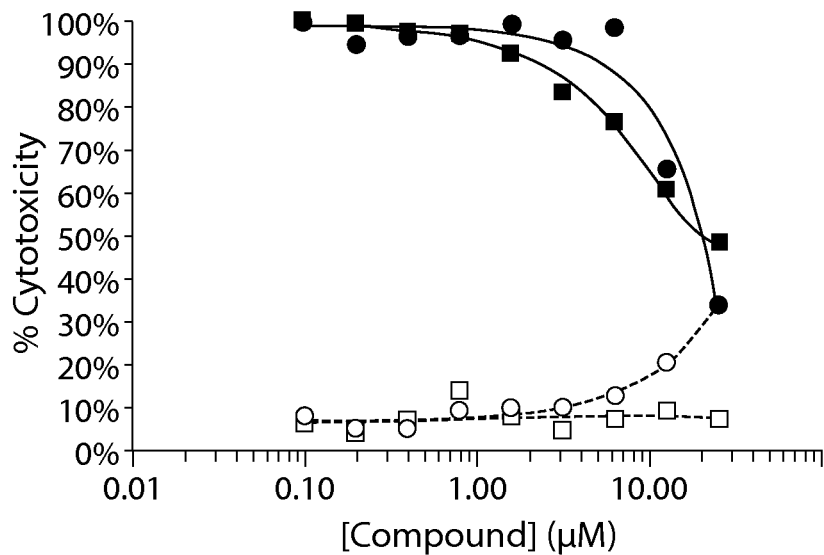
FIG. 3A shows concentration-dependent rescue of CHO cells from ExoU cytotoxicity by T3SS inhibitor MBX 1641 (re-synthesized compound 1). ExoU-secreting *P. aeruginosa* strain PAKΔSTYexoU was mixed with CHO cells at an MOI of 5 in the presence of MBX 1641 (black circles, ●) or the known ExoU inhibitor pseudolipasin (black squares, ■) (27) at various concentrations as indicated. Percent (%) cytotoxicity is calculated as the % of LDH released from cells intoxicated with *P. aeruginosa*+/–inhibitor as compared to LDH released from intoxicated cells that were not treated with inhibitor. The effects of pseudolipasin (white squares, □) and MBX 1641 (white circles, ○) are also shown in the absence of *P. aeruginosa* cells in order to evaluate the inherent cytotoxicity of the compounds themselves. See, Example 4, for details.

To assess their effects on T3SS-mediated translocation of effectors, five specific inhibitors of type III secretion, i.e., compounds 1, 3, 4, 8, and 9 (see Table 3), were tested in a cellular activity assay for T3SS effector translocation into mammalian cells (27). The compounds were added to CHO cells simultaneously with addition of *P. aeruginosa* ExoU-producing cells to determine whether the inhibitors were capable of blocking CHO cell death due to the cytotoxic activity of translocated ExoU. Only compound 1 was capable of reproducibly rescuing CHO cells from the ExoU-secreting *P. aeruginosa* cells (FIG. 3A), and its potency in this assay ($IC_{50}$~15 µM) was similar to its potencies in the ExoS'-βLA assay (Table 3) and in the inhibition of secretion of native ExoS (FIG. 2B). These results demonstrate that the phenoxyacetamide compound 1 not only blocks T3SS-mediated secretion of effectors from *P. aeruginosa* into culture medium, but also blocks translocation of effectors into mammalian cells.

Figure 5A:
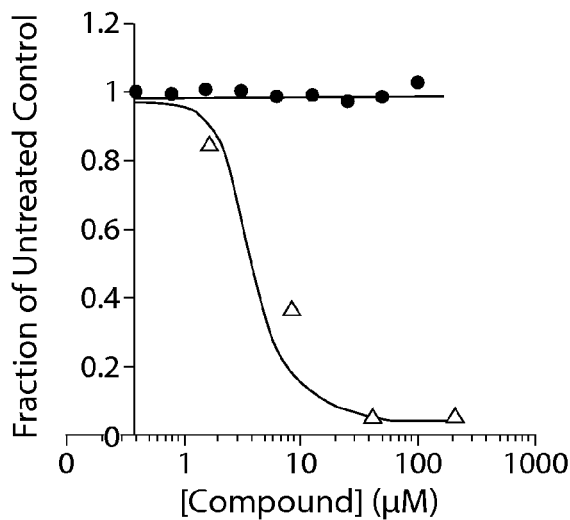
FIG. 5A shows a determination of the minimal inhibitory concentration of MBX 1641 for *P. aeruginosa*. *P. aeruginosa* PAO1 cells were grown in the presence of the indicated concentrations of MBX 1641 (black circles, ●) or tetracycline (white triangles, △) for 16 hours in clear 96-well microplates, and the $A_{600}$ was determined. The $A_{600}$ as a fraction of that of DMSO-treated control cells is plotted. See, Example 6.
Figure 5B:
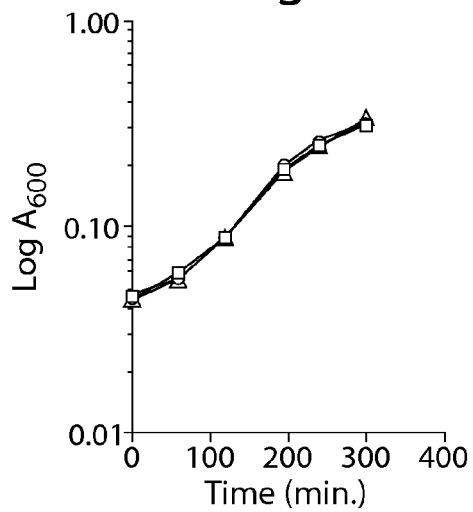
FIG. 5B shows the growth rate of *P. aeruginosa* cells treated with MBX 1641. *P. aeruginosa* PAO1 cells were grown in the presence of three different concentrations of MBX 1641 for 5 hr in clear 96-well microplates, and the $A_{600}$ was measured periodically as indicated as a measure of cell density. MBX 1641 was present at 100 μM (small white squares, □), 50 μM (large white squares), or 25 μM (white circles, ○), or cells were treated with an equivalent concentration (2%) of DMSO only (white triangles, △). See, Example 6.
Figure 5C:
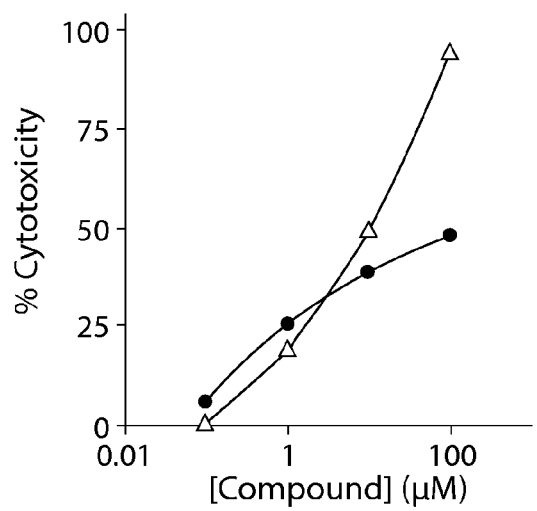
FIG. 5C shows HeLa cell cytotoxicity of MBX 1641 compared to the antibiotic novobiocin. HeLa cells were cultured in VP-SFM medium without serum in the presence of the indicated concentrations of MBX 1641 (black circles, ●) or novobiocin (white triangles, △) for 3 days, and cytotoxicity was determined by the ability of remaining live cells to reduce a vital tetrazolium salt stain. Results are plotted as the percentage of cytotoxicity relative to DMSO-treated and Triton X-100 non-ionic detergent lysed control cells. See, Example 6.

Rescue from ExoU cytotoxicity by compound 1 was limited somewhat due to cytotoxicity of the compound itself in the absence of *P. aeruginosa* cells which reaches about 30% at 25 µM (FIG. 3A, open circles) and 50% at 75 µM (not shown). This $CC_{50}$ value is somewhat lower than the values obtained with HeLa cells (102 µM in Table 3, and see FIG. 5C, below) and 293T cells (110 µM, data not shown) in the absence of serum. The difference probably reflects the facts that three different cell types were employed, and that the CHO cells were under stress due to the sudden reduction in serum levels from 10% to 1% just prior to infection with *P. aeruginosa* cells. In any case, there is a clear margin of efficacy for compound 1 in this CHO rescue experiment. A known ExoU inhibitor, pseudolipasin (27), also rescued CHO cells from ExoU toxicity with a similar potency. Compound 1 was re-synthesized and the resulting compound, designated MBX 1641, exhibited the same T3SS inhibition potency and selectivity as the original compound 1.

Figure 3B:
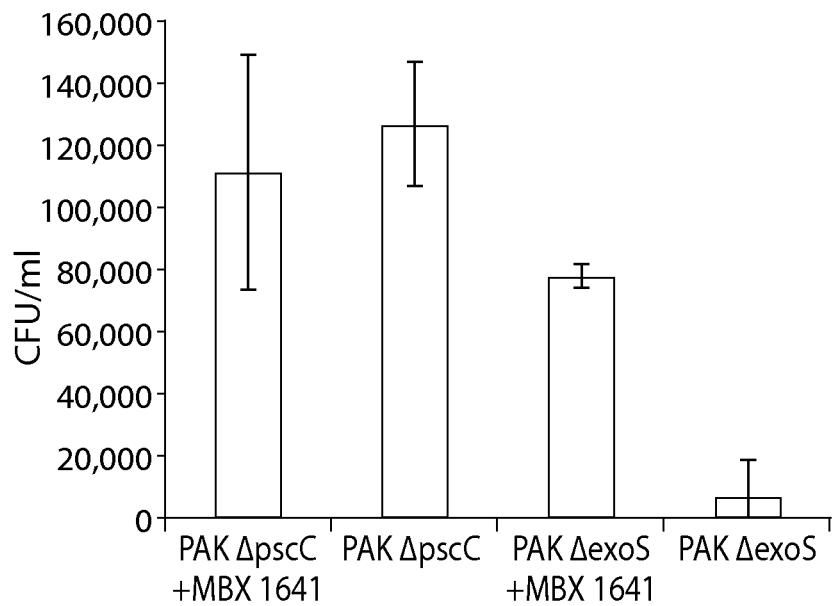
FIG. 3B shows that the T3SS inhibitor MBX 1641 relieves the ExoT block of HeLa cell internalization of *P. aeruginosa*. HeLa cells were infected with *P. aeruginosa* PAK strains secreting ExoT (PAKΔexoS) (bars 3 and 4) or deficient in T3SS (PAKΔpscC) (bars 1 and 2) at an MOI of 10. MBX 1641 was added at 50 μM to half the wells containing each strain (bars 1 and 3). After 2 hours, cultures were treated with gentamicin (50 μg/ml) for an additional 2 hours. HeLa cells were lysed with Triton non-ionic detergent, and serial dilutions were plated to determine the number of *P. aeruginosa* cells (colony-forming units, CFU) that had been protected from gentamicin by internalization. The CFU/ml of *P. aeruginosa* cells from lysed HeLa cells were determined in triplicate and plotted as the average+/– the standard deviation. See, Example 4, for details.

ExoS and ExoT appear to block uptake of *P. aeruginosa* cells by both epithelial and phagocytic cells in culture, suggesting that the T3SS may function as a virulence factor by preventing phagocytic cell clearance of *P. aeruginosa* cells during infection (6, 15). Inhibition of T3SS-mediated secretion and translocation of ExoS or ExoT by mutation results in increased internalization of bacteria (6, 15, 18, 50). MBX 1641 was tested to determine if its T3SS inhibition would facilitate the internalization of *P. aeruginosa* cells by HeLa cells in culture. Addition of the compound at 50 µM to HeLa cells simultaneously with the addition of ExoT-producing *P. aeruginosa* cells at a multiplicity of infection of 10 resulted in a stimulation of internalization of bacterial cells by over 11-fold as measured by protection of bacteria from gentamicin (compare bar 3 (+MBX 1641) with bar 4 (untreated) in FIG. 3B). In the presence of MBX 1641, the number of internalized *P. aeruginosa* ExoT-secreting cells (bar 3 of FIG. 3B) increased to nearly the number of T3SS-deficient ΔpscC cells taken up by HeLa (bar 2 of FIG. 3B). As expected, MBX 1641 had no significant effect on the already high levels of uptake of a T3SS-deficient ΔpscC mutant strain (compare bars 1 (+MBX 1641) and 2 (untreated), FIG. 3B).

Example 5

Bacterial Spectrum of Activity

Figure 3C:
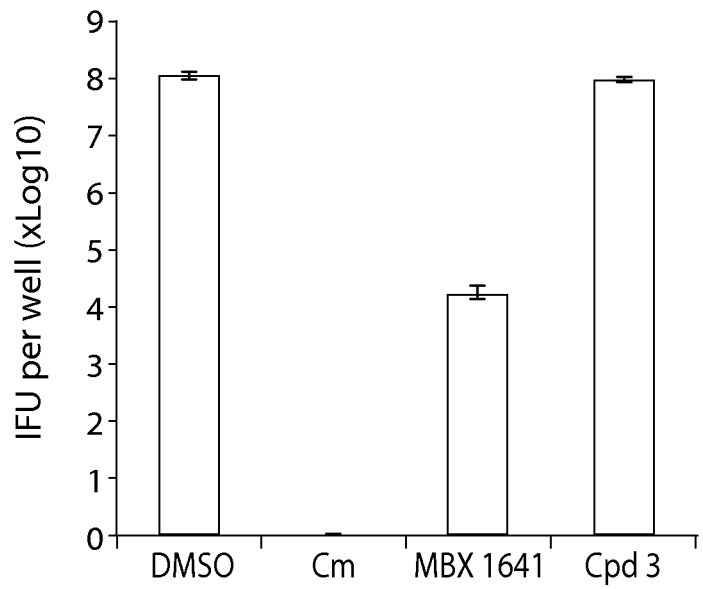
FIG. 3C shows that MBX 1641, but not compound 3, inhibits the growth of *C. trachomatis* L2 cells in Hep-2 cells in culture. Confluent monolayer Hep-2 cells were infected with L2 at an MOI of 0.5 and treated with compounds (50 μM) (bar 3, + MBX 1641) (bar 4, +compound 3), followed by sonication and measurement of IFUs on HeLa monolayers. Experiments were done in triplicate, and averages+/–standard deviation are shown. Chloramphenicol (Cm, bar 2) was used at 200 μg/ml as a positive control. Compound diluent (DMSO, bar 3) was used as a negative control. Bar 3, cultures treated with MBX 1641. Bar 4, cultures treated with compound 3. See, Example 5, for details.
Figure 3D:
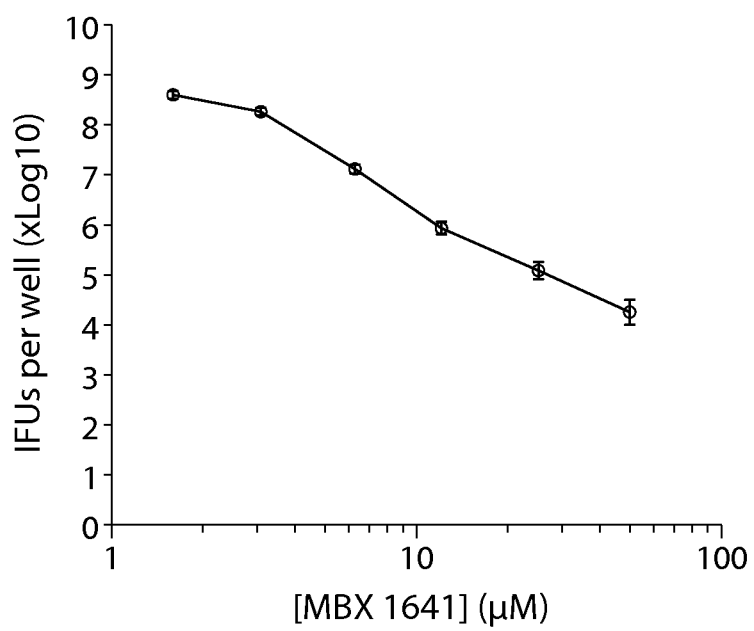
FIG. 3D shows concentration-dependence of the inhibition of *C. trachomatis* L2 growth in Hep-2 cells by MBX 1641. See, Example 5, for details.

The intracellular pathogen *Chlamydia trachomatis* expresses a T3SS thought to be responsible for injecting effectors into the host cytosol (23). Recently, *Yersinia* T3SS inhibitors INP0007 and INP0400, both members of an acylated hydrazone series (40), were demonstrated to arrest growth of *C. trachomatis* in mammalian cell hosts (38, 59), suggesting that T3SS plays an essential role in the *Chlamydia* development cycle. MBX 1641 (re-synthesized compound 1) and compound 3 (Table 3) were tested for the ability to block the growth of *C. trachomatis* L2 in Hep-2 cells. The results reveal that MBX 1641, but not compound 3, significantly reduced the growth of *C. trachomatis* when added at 50 µM (compare bar 3 (+MBX 1641) with bar 4 (compound 3) of FIG. 3C). In addition, MBX 1641 exhibited a concentration-dependent effect on *C. trachomatis* growth in Hep-2 cells (FIG. 3D). These results suggest that MBX 1641 is capable of inhibiting T3SS in *Chlamydia*.

Figure 4A:
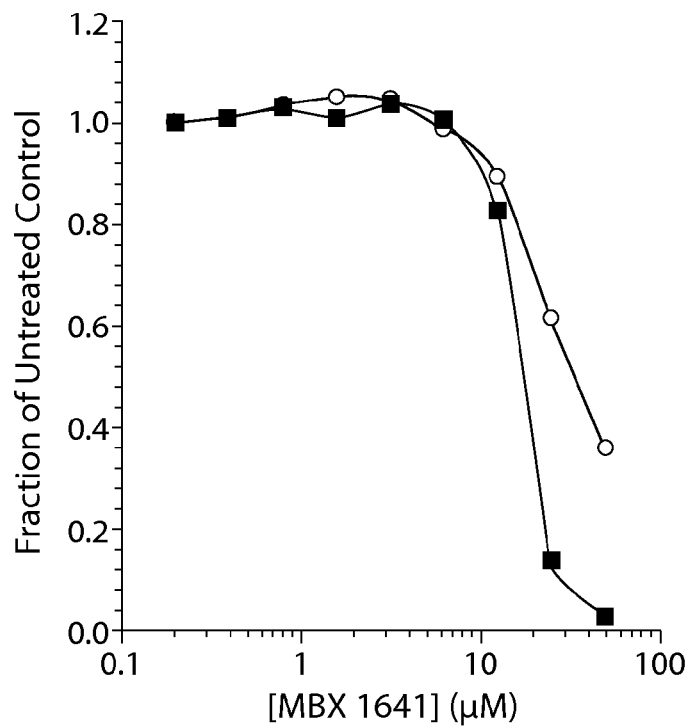
In FIG. 4A, cells growing under T3SS-inducing conditions were treated for 3 hours with MBX 1641, and β-lactamase activity was measured by cleavage of nitrocefin as $\Delta A_{490}$/min. The rate of nitrocefin cleavage as a fraction of that of the untreated control is plotted versus the compound concentration. Bacterial species and effector 13LA fusions were as follows: *P. aeruginosa* ExoS'-βLA (black squares, ■), *Y. pestis* YopE-βLA (white circles, ○). See, Example 5, for details.

The ability of MBX 1641 to inhibit the T3SS of *Yersinia pestis* was also examined. As shown in FIG. 4A, MBX 1641 inhibits T3SS-dependent secretion of a YopE-βLA effector fusion protein from attenuated *Y. pestis* strain JG153 (white circles in FIG. 4A) with a potency about 3-fold poorer ($IC_{50}$~38 µM) than that observed for its inhibition of ExoS'-βLA secretion from *P. aeruginosa* (black squares in FIG. 4A). It is interesting to note that the other four validated T3SS inhibitors of *P. aeruginosa* type III secretion also inhibit *Y. pestis* T3SS-mediated secretion (Table 3), consistent with the fact that the structural components of these two TTS systems share considerable sequence homology (23).

Example 6

Preliminary Structure-Activity Relationship (SAR) for Phenoxyacetamide T3SS Inhibitors Results described above demonstrate that MBX 1641 inhibits both T3SS-mediated secretion and translocation. In addition, it does so with minimal effects on the extent (see, FIG. 5A) and rate (see, FIG. 5B) of growth of *P. aeruginosa* cells and on the viability of HeLa cells (see, FIG. 5C), yielding a favorable selectivity index ($CC_{50}/IC_{50}$) of approximately 10. To explore the structure-activity relationships of the phenoxyacetamide series represented by MBX 1641, a total of 114 analogs were purchased (ChemBridge Corporation) and assayed for T3SS inhibition at a single concentration (50 µM) (structures included in catalog in FIG. 8). $IC_{50}$ values were determined for several key analogs by using the ExoS'-βLA assay (Table 4). The results indicate that very few alterations are acceptable on ring A, but there is considerable flexibility in the substituents tolerated on ring B. Results also suggest that the linker region cannot be lengthened by one methylene unit, but a tertiary amine is tolerated with some loss of activity. The discovery of inhibitory analogs in series A supports the validity of this chemotype as a T3SS inhibitor and provides a basis for further optimization of the potency of this class of inhibitors.

Figure 4B:
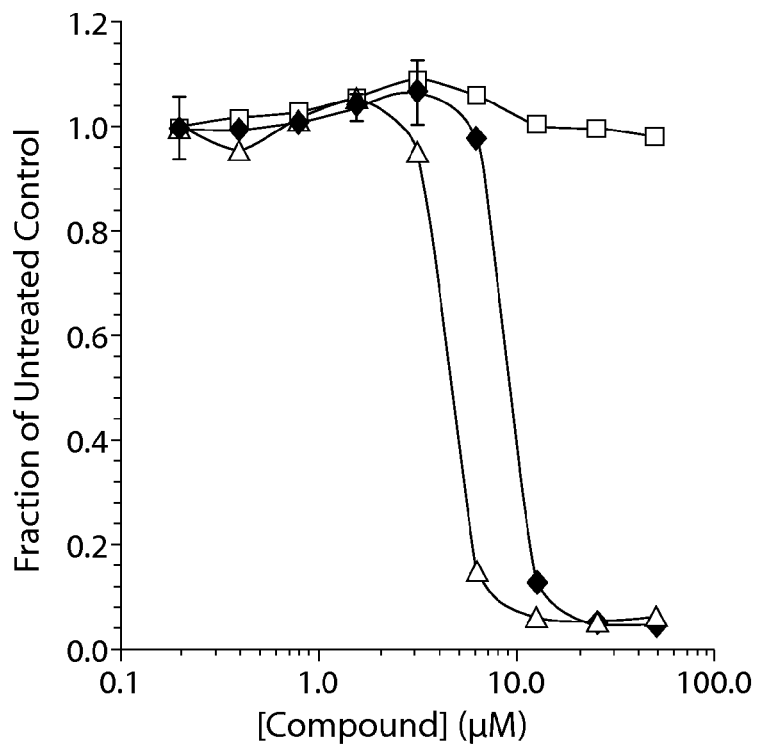
FIG. 4B shows the effects of MBX 1641 and its R- and S-enantiomers on ExoS'-βLA secretion from *P. aeruginosa*. Concentration-dependence for MBX 1641 and its two stereo isomers, MBX 1684 (R-enantiomer) and MBX 1686 (S-enantiomer) were determined by the rate of nitrocefin cleavage by secreted ExoS'-βLA and calculated as the fraction of cleavage in the absence of inhibitor. Racemic mixture MBX 1641 (black diamonds, ♦), R-enantiomer MBX 1684 (white triangles, △), and S-enantiomer MBX 1686 (white squares, □).
Figure 6:
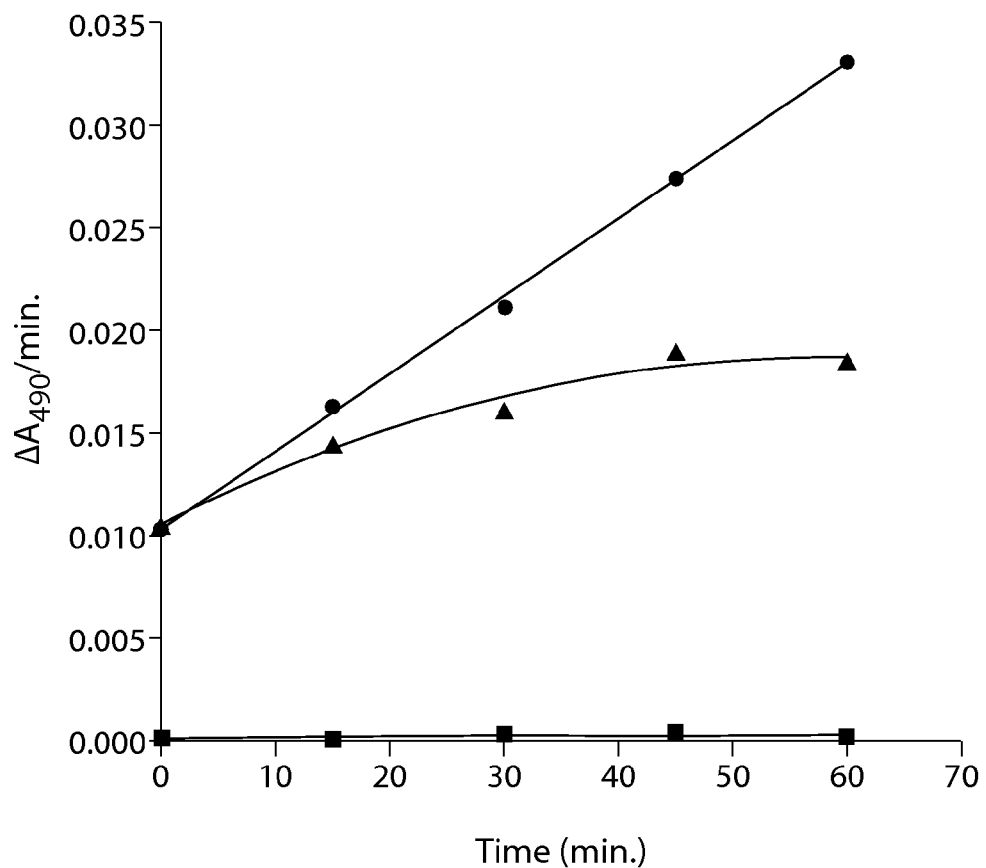
FIG. 6 shows plots of $\Delta A_{490}$/min. (slope) versus time (min.) for secretion of ExoS'-βLA fusion protein over time in cultures of *P. aeruginosa* strain MDM973 grown under T3SS inducing conditions. As a control, a separate culture of the same cells was grown without induction of T3SS (black squares, ■). After 2.5 hours, compound 1 was added at 50 μM to one portion of the T3SS-induced cells. Simultaneously, the βLA chromogenic substrate nitrocefin was added to portions of all three cultures, and the $A_{490}$ was recorded over time (minutes). Every 15 minutes, another portion of all three cultures was withdrawn, nitrocefin was added, and slopes were determined. The slope of $A_{490}$ versus time ($\Delta A_{490}$/min.) is proportional to the amount of ExoS'-βLA secreted into and accumulating in the culture medium. Secretion of ExoS'-βLA fusion protein in culture of cells grown under T3SS induction without addition of inhibitor (black circles, ●). Secretion of ExoS'-βLA fusion protein in culture of cells grown under T3SS induction with addition of inhibitor (black triangles, ▲). See, Example 7 for details.

Further SAR studies focused on the single stereocenter of MBX 1641 (* in Table 4), which is a racemic mixture. Since pure enantiomers were not available for purchase, the two stereoisomers, MBX 1684 (R-isomer) and MBX 1686 (S-isomer) were synthesized. Also, to evaluate the effect of eliminating the stereocenter, analogs of MBX 1641 lacking the methyl group at the stereocenter in the linker region (MBX 1668) and containing two methyl groups at the stereocenter (MBX 1685) were synthesized. The concentration-dependent inhibition of T3SS by these compounds was measured in the ExoS'-βLA reporter assay, and the results unambiguously establish the importance of the stereocenter for T3SS inhibitory activity. Only the R-isomer was active, and it was almost twice as potent as the racemic mixture (see, FIG. 4B and Table 4, $IC_{50}$~6 μM for MBX 1684 vs. ~10 μM for MBX 1641). Both analogs lacking the stereocenter, the desmethyl, and dimethyl compounds, were inactive ($IC_{50}$ values >100 μM, Table 4), as was the S-isomer MBX 1686 (FIG. 4B).

nitrocefin was added, and slopes were determined. The slope of a plot of $A_{490}$ versus time in minutes ($\Delta A_{490}$/min.) is proportional to the amount of ExoS'-βLA secreted into and accumulating in the culture medium. A plot of the slope ($\Delta A_{490}$/min.) versus time of assay (FIG. 6) indicates that compound 1 inhibited T3SS-mediated secretion of ExoS'-βLA by 50% within 15 minutes and 100% within 45 minutes of addition to the culture. Such rapid kinetics rule out effects on gene expression as the primary mechanism and indicate that these compounds inhibit T3SS directly. As expected, induced cells in the absence of compound 1 continued to secrete ExoS'-βLA, while uninduced cells secreted no detectable ExoS'-βLA. See, FIG. 6.

TABLE 4

Preliminary Structure-Activity Relationships

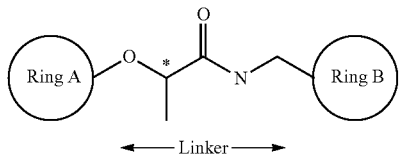

| Vendor ID | $IC_{50}$ (μM) (ExoS'-βLA assay) | Stereo-center | Ring A | Linker Modification | Ring B |
|---|---|---|---|---|---|
| MBX 1641 | 10 | racemic | 2,4-dichlorophenyl | none | 3,4-methylenedioxyphenyl |
| MBX 1684 | 6 | R-isomer | 2,4-dichlorophenyl | none | 3,4-methylenedioxyphenyl |
| MBX 1686 | >100 | S-isomer | 2,4-dichlorophenyl | none | 3,4-methylenedioxyphenyl |
| MBX 1668 | >100 | none | 2,4-dichlorophenyl | desmethyl | 3,4-methylenedioxyphenyl |
| MBX 1685 | >100 | none | 2,4-dichlorophenyl | dimethyl | 3,4-methylenedioxyphenyl |
| 6109233 | 5 | racemic | 2,4-dichlorophenyl | none | 4-methylphenyl |
| 6380194 | 9 | racemic | 2,4-dichlorophenyl | none | 4-fluorophenyl |
| 6375680 | 10 | racemic | 2,4-dichlorophenyl | none | 4-methoxyphenyl |
| 6374948 | 12 | racemic | 2,4-dichlorophenyl | none | 2-methoxyphenyl |
| 6468028 | 21 | racemic | 2,4-dichlorophenyl | N-methyl | phenyl |
| 5685325 | 25 | racemic | 2,4-dichlorophenyl | none | furan-2-yl |
| 6374984 | 45 | racemic | 2,4-dichlorophenyl | none | pyridine-2-yl |
| 6372013 | 59 | racemic | 2,4-dichlorophenyl | none | pyridine-4-yl |
| 8804126 | 61 | racemic | 2,4-dichlorophenyl | none | 1,3-dimethylpyrazol-4-yl |
| 7229146 | 100 | racemic | 2,4-dichlorophenyl | constrained tert-amine | 1,2,3,4-tetrahydroisoquinoline |
| 6467504 | >100 | racemic | 2,4-dichlorophenyl | +CH$_2$ | 2-cyclohexen-1-ylmethyl |
| 7271715 | >100 | racemic | 2,4-dichlorophenyl | none | 3,4-dichlorophenyl |
| 7314595 | >100 | racemic | 2,4-dichlorophenyl | +CH$_2$ | 2-chlorophenyl |
| 9153915 | 23 | racemic | 2-chlorophenyl | none | 3,4-methylenedioxyphenyl |
| 6116488 | 98 | racemic | 2-methyl-4-chlorophenyl | none | 3,4-methylenedioxyphenyl |
| 7339628 | >100 | racemic | 2-fluorophenyl | none | 3,4-methylenedioxyphenyl |
| 7303859 | >100 | racemic | 3-chlorophenyl | none | 3,4-methylenedioxyphenyl |

Example 7

Kinetics of Inhibition of T3SS by Compound 1

In order to determine how rapidly compound 1 is capable of inhibiting T3SS, the following experiment was conducted. *P. aeruginosa* cells carrying the ExoS'-βLA fusion protein (strain MDM973) were grown under T3SS inducing conditions. As a control, a separate culture of the same cells was grown without induction for T3SS. After 2.5 hours, compound 1 was added at 50 μM to one portion of the T3SS induced cells. Simultaneously, nitrocefin was added to portions of all three cultures, and the $A_{490}$ resulting from cleavage of nitrocefin by ExoS'-βLA was recorded. Every 15 minutes, another portion of all three cultures was withdrawn, Example 8

Inhibition of T3SS-Mediated Effector Translocation by Analogs of Compound 1

Figure 7A:
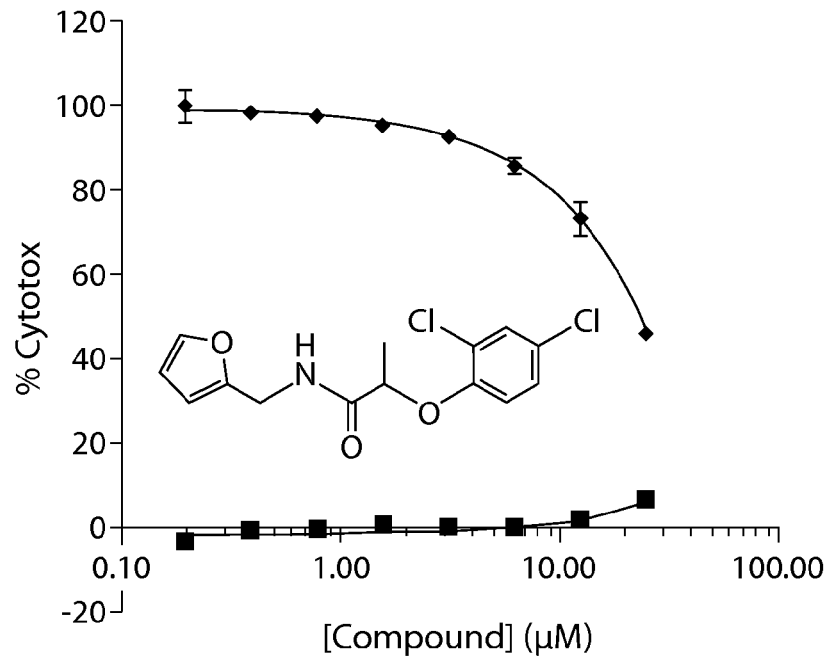
FIG. 7A shows plots T3SS inhibitor compound 5685325 (ChemBridge Corporation).
Figure 7B:
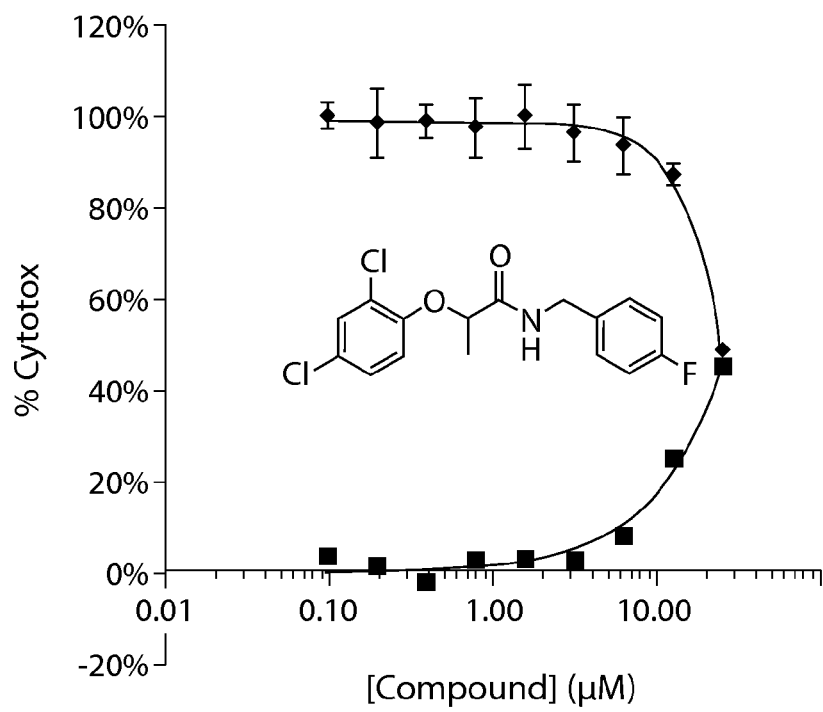
FIG. 7B shows plots for T3SS inhibitor compound 638014 (ChemBridge Corporation). See, Example 8 for details.

Two analogs of compound 1, compound 5685325 (ChemBridge Corporation, FIG. 8B) and compound 6380194 (ChemBridge Corporation, FIG. 8B), also rescued CHO cells from intoxication by ExoU translocated by *P. aeruginosa* cells through the T3SS (FIG. 7). These results demonstrate that other members of the phenoxyacetamide chemotype not only block T3SS-mediated secretion of effectors from *P. aeruginosa* into culture medium, but also block translocation of effectors into mammalian cells. Rescue from ExoU cytotoxicity by the analogs was limited somewhat due to cytotoxicity of the compounds in the absence of *P. aeruginosa* cells, which reached about 8% and 42% at 25 µM for the two analogs, respectively. These results for compound 5685325 also indicate that modifications to the compound 1 scaffold are capable of reducing the inherent cytotoxicity while still providing potent inhibition of T3SS-mediated translocation of effector toxin ExoU.

Example 9

Results and Conclusions from Examples 1-8

In the above studies (Examples 1-8), a bioluminescent cellular reporter screen and multiple secondary assays were employed to identify and validate new selective inhibitors of *P. aeruginosa* T3SS-mediated secretion. One of the compounds (compound 1, from screen; re-synthesized designation MBX 1641) is also an inhibitor of T3SS-mediated translocation. Selected compounds 1, 3, 4, 8, and 9 display minimal cytotoxicity ($CC_{50} \geq 100$ µM) and moderate potency ($IC_{50}$ values ≤15 µM) and exhibit no significant effects on the extent or rate of growth of *P. aeruginosa* cells, nor do they inhibit the type II secretion system as determined by measurements of secreted elastase. The compounds represent 3 different chemotypes (series A, B, and D, Table 3), but series A and B appear to be structurally related and contain a stereocenter, which was demonstrated to be critical for activity for series A. Compound 1 (MBX 1641) in series A reproducibly inhibits both T3SS-mediated secretion and translocation and was an effective antagonist in three mammalian cell assays which depend on T3SS intoxication of CHO cells by ExoU-producing *P. aeruginosa*, blockage by *P. aeruginosa* of HeLa cell internalization, and growth of *C. trachomatis* in Hep-2 cells. The potency and selectivity of inhibitors in series A suggest that this class of T3SS inhibitors is suitable for further chemical optimization to produce a clinically useful inhibitor. Table 3 also provides data on compounds 8 and 9 of chemotype series D as well as singleton compounds 10 and 11.

It is unclear why compounds 3, 4, 8, and 9, which are validated inhibitors of T3SS-mediated secretion, failed to inhibit T3SS-mediated translocation as measured by rescue of CHO cells from ExoU intoxication (Example 4). Most secretion inhibitors would be expected to inhibit translocation since many aspects of T3SS-mediated secretion are also required for translocation. At least four possible explanations could account for this discrepancy. First, the inhibitors may interact with the T3SS apparatus at a site that is inaccessible when the *P. aeruginosa* needle is docked to the mammalian cell membrane. Second, inherent cytotoxicity of the inhibitors may preclude our ability to detect rescue of CHO cells from ExoU-mediated cytotoxicity. Some cytotoxicity was evident even in the successful inhibition by MBX 1641, and it limited our ability to achieve complete rescue of CHO cells. While the four secretion inhibitors do not appear to be more cytotoxic than MBX 1641, even subtle increases in cytotoxicity may be sufficient to mask CHO cell rescue in this assay. Third, the secretion inhibitors may bind extensively to serum proteins and be unavailable for activity in the mammalian cell-based translocation assay. In fact, compounds 3, 4, and 9 do display greater loss of activity in the presence of serum than does compound 1 (MBX 1641) ("serum effect", Table 3). A fourth formal possibility is that the inhibitors may block T3SS induced by low $Ca^{++}$ but not by mammalian cell contact. However, the speed with which the inhibitors function seems to preclude action at the level of transcription regulation (see below).

The phenoxyacetamide MBX 1641 does not appear to be related structurally to any of the T3SS inhibitors reported previously. Results have been described for T3SS inhibitor screens in *Yersinia pseudotuberculosis* (24, 41), *Y. pestis* (44), enteropathogenic *Escherichia coli* (EPEC) (16), *Salmonella typhimurium* (12), and *P. aeruginosa* (27). All have utilized cell-based assays, both for direct identification of compounds active against whole cells and because the complexity of the molecular machine renders biochemical screens of component parts of T3SS particularly challenging. The only previously described screen for *P. aeruginosa* T3SS inhibitors was based on the reducing potential of remaining live CHO cells and consequently could detect inhibitors of any step in the secretion, translocation, and toxin activity leading to mammalian cell death (27). The validated inhibitors identified in the screen were shown to inhibit the ExoU toxin directly rather than the T3SS process itself. However, one series of hits described in that study displays structural similarity to MBX 1641. Two compounds in that series, 5929052 and 5925831 (see Supplemental Table 2 in (27)), failed to exhibit detectable inhibition in the ExoS'-βLA assay described here ($IC_{50}$ values >100 µM; unpublished results). The absence of detectable inhibition is not surprising since those compounds were identified as ExoU inhibitors and since they lack the stereocenter demonstrated to be crucial for T3SS-inhibitory activity of MBX 1641 (e.g., see desmethyl analog in Table 4). It is particularly interesting to compare the previously reported inhibitors of *Y. pseudotuberculosis* and *Y. pestis* T3SS to the inhibitors identified in this study because the *Pseudomonas* T3SS proteins exhibit more sequence similarity to those of *Yersinia* than to those of any other genus (23). Two *Y. pseudotuberculosis* T3SS inhibitors, compounds 8 and 11 described in Nordfeth et al., *Infect. Immun.*, 73: 3104-3114 (2005) (41), were present in our screening collection. While they do inhibit *P. aeruginosa* T3SS moderately, they failed to inhibit the exoT-lux primary reporter screen with sufficient potency to be selected as primary hits (unpublished observations). One *Y. pestis* T3SS inhibitor (compound 2 described in Pan et al., *Antimicrob. Agents Chemother.*, 53: 385-392 (2009) (44)), was also present in our screening collection, and it proved to be a potent inhibitor of *P. aeruginosa* T3SS in the primary and secondary screens applied here ($IC_{50} \leq 10$ µM in the ExoS'-βLA assay), but was not pursued due to high serum protein binding. The ability of 3 different *Yersinia* T3SS inhibitors to block *P. aeruginosa* T3SS is consistent with the high sequence homology observed for T3SS components in the two genera and with the ability of the five *P. aeruginosa* T3SS inhibitors described in this study to inhibit *Y. pestis* T3SS-mediated secretion.

The molecular target(s) of these *P. aeruginosa* T3SS inhibitors is not known; however, the results described here provide some evidence that these compounds specifically inhibit the activity of the T3SS apparatus. First, the data show that the compounds are not simply inhibiting one of the effector toxins because they specifically affected the secretion or the translocation of three different effectors—ExoS (SDS-PAGE), ExoT (HeLa cell internalization), and ExoU (rescue of CHO cells). Second, the inhibitors do not affect the extent (MIC) or rate of growth of *P. aeruginosa* cells. Third, the compounds do not appear to be general inhibitors of gene expression or virulence gene expression because they demonstrate differential effects on the generation of luminescence by strains carrying exoT-lux and lac-lux transcriptional fusions, and they do not inhibit production or secretion of another virulence factor, elastase, which utilizes the type II secretion mechanism. Fourth, inhibition of ExoS'-βLA secretion by MBX 1641 is equally potent when measured in a multiple efflux-pump knock-out strain—*P. aeruginosa* strain PA0397 (26) (provided by Dr. Herbert Schweizer, Colorado State Univ.) (unpublished observations). This suggests that T3SS inhibitors are not effluxed and/or do not need to enter *P. aeruginosa* cells to act, and the latter possibility is more likely since few small molecules enter and are retained in *P. aeruginosa* cells (30). Fifth, MBX 1641 acts equally potently to block ExoS'-βLA secretion whether administered during or after the 2.5 hour EGTA induction of T3SS, suggesting that the compound is not blocking T3SS gene expression or assembly of the type III apparatus (unpublished observations). Finally, the strict requirement for the R-isomer configuration at the stereocenter of the phenoxyacetamide series indicates that the inhibitor is interacting with a specific target or targets and is not acting by a promiscuous non-specific mechanism. The observed spectrum of activity against T3SS in three bacterial species points to a conserved target, but the sequence conservation is high across species among many of the T3SS gene products.

In addition to establishing the importance of the stereocenter in the linker region of the phenoxyacetamide series (Series A), the initial SAR described here provides some clear directions for improving the potency of the inhibitor. The low tolerance for alterations to ring A (Table 4) suggests that this region of the molecule together with the stereocenter is involved in important contacts with the target. Further chemical optimization of these regions may provide improved potency. By contrast, the considerable tolerance demonstrated for various substituents on ring B (Table 4) suggests that few target contacts are made on that side of the compounds, perhaps providing a location for a tethered photoreactive group for target identification or for other modifications to provide ADME benefits.

The results of the foregoing examples show that MBX 1641 is capable of inhibiting the T3SS of three different bacterial species: *P. aeruginosa*, *Y. pestis*, and *C. trachomatis*. Multiple different assays demonstrate the inhibition of *P. aeruginosa* T3SS while inhibition of T3SS in the other two species is based on a single assay in each case. Nevertheless, effector-β-lactamase fusion proteins appear to be reliable reporters of T3SS function. In the absence of a manipulable genetic system in *Chlamydia*, it has not been possible to firmly establish the essentiality of the T3SS for intracellular growth. The possibility that MBX 1641 is arresting *C. trachomatis* growth by mechanisms other than T3SS inhibition cannot be ruled out, but the compound has not demonstrated promiscuous behavior in a variety of assays and does not appear to be overtly cytotoxic or to block gene expression.

From the foregoing, compound 1641 and its R-stereoisomer are seen to be potent and selective inhibitors which block both T3SS-mediated secretion and translocation of *P. aeruginosa* effectors. The absolute requirement for the R-stereoisomer indicates that the phenoxyacetamides (structure series A, Table 3; see FIG. 8) target a specific component required for type III secretion. The structure-activity relationships demonstrated here suggest approaches to optimize this compound series to achieve higher potency and reduced cytotoxicity. Such optimized compounds could be evaluated in animal models either alone or in combination with antibiotics to determine their benefit in potential therapeutic applications.

Example 10

Summary of Compound 1 (MBX 1641) Analogs

FIGS. 8A-8Q provide a summary catalog of MBX 1641 (re-synthesized compound 1) and 117 analogs that were characterized for T3SS inhibitory activity. Sixteen additional analogs of MBX 1641 (in addition to its R-stereoisomer, MBX 1684) were discovered to be specific T3SS inhibitors. See FIGS. 8A-8C.

Example 11

Additional Validated T3SS Inhibitor Compounds

Screening of an additional library using the methods and assays described above identified additional validated T3SS inhibitors. See Table 5.

TABLE 5

Additional Validated T3SS Inhibitors.[†]

| Series | Structure | RLU-S[a] | SE[b] | ExoS'-βLA IC$_{50}$[c] | Vendor[d] |
|---|---|---|---|---|---|
| n.a. | $C_{14}H_{12}N_2O_2$ | 4.2 | 1.6 | 22.3 | 6430631 |
| A | $C_{18}H_{23}Cl_2NO_2$ | 5.6 | 3.4 | 16.7 | 7247834 |

TABLE 5-continued

Additional Validated T3SS Inhibitors.[†]

| Series | Structure | RLU-S[a] | SE[b] | ExoS'-βLA IC$_{50}$[c] | Vendor[d] |
|---|---|---|---|---|---|
| A | $C_{19}H_{17}N_3O_3$ | 10.8 | 2.1 | 22.3 | F5054-0019 |

[†]All IC$_{50}$ and CC$_{50}$ values are presented in μM units.
[a]RLU Selectivity = % inhibition of exoT-lux RLU/% inhibition of lac-lux RLU, both at 50 μM compound
[b]Serum Effect = % inhibition of exoT-lux RLU in the absence of serum/% inhibition of exoT-lux RLU in the presence of 10% fetal calf serum, both at 50 μM compound
[c]Compound concentration at which secretion of ExoS'-βLA fusion protein from *P. aeruginosa* strain MDM973 is reduced by 50%
[d]ChemBridge, except F5054-0019 from Life Chemicals

Example 12

Synthesis of Phenoxyacetamide T3SS Inhibitor Compound 1 and Analogs (Chemotype A)

This example provides a synthetic scheme for the phenoxyacetamide compounds such as the T3SS inhibitor compound 1 identified in the screening and validation protocol described above and for selected analogs of chemotype A. See, Table 3, above. As noted above, the re-synthesized version of compound 1 was designated MBX 1641. "MBX" designations of compounds are the same as those described in the above description and examples. The other compound numbers are only relevant to the description of the specific synthetic schemes and protocols provided below.

Synthetic Schemes

Phenoxyacetamides can be synthesized using well-established chemistry from commercially available starting materials. The compounds 2a (MBX 1668, "des-methyl" analog of MBX 1641; see Table 4, above) and the validated T3SS inhibitor 2b (MBX 1641, racemic mixture, re-synthesized version of compound 1 in Table 3, above) are made (Scheme 1, below) in one step from the corresponding commercial phenoxyacetic acids (1a, 1b) and piperonylamine using common peptide coupling reagents.

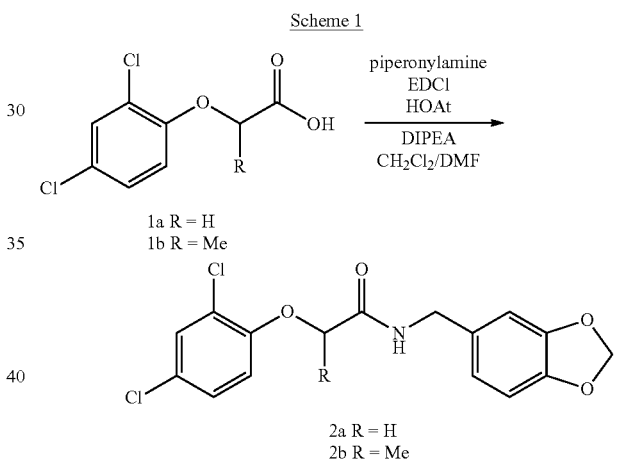

Scheme 1

The gem-dimethyl analog 7 (MBX 1685, Table 4) is synthesized similarly, starting from the commercially available α-bromoester 4 and 2,4-dichlorophenol 3. Thus, base-promoted displacement of the bromo group provides the intermediate ester 5, which is then saponified to the acid 6. Peptide coupling of this acid with piperonylamine produces the desired compound 7 (designated MBX 1685, "dimethyl" analog of MBX 1641).

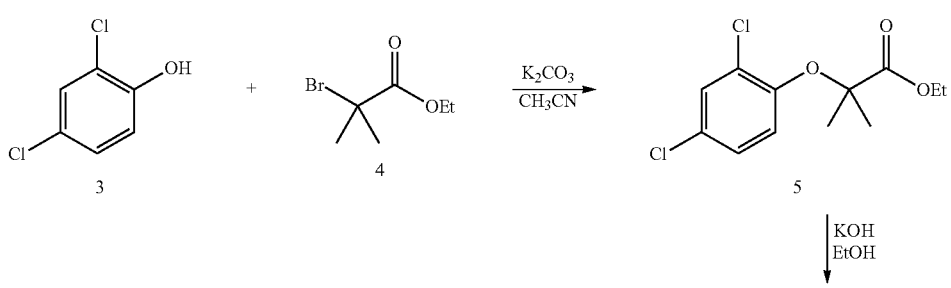

Scheme 2

-continued

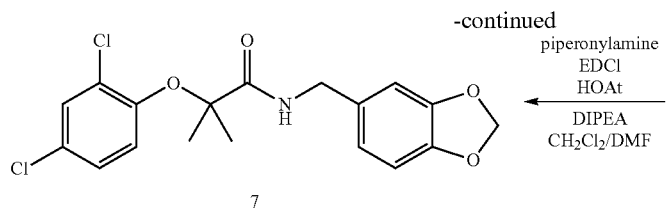

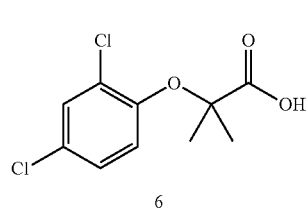

Synthesis of optically pure analogs of compounds 2b (i.e., 11a and 11b, below) begins from the commercially available (5)-ethyl lactate (Scheme 3). Displacement of the hydroxy group of the lactate with dichlorophenol under Mitsunobu conditions proceeds with inversion of configuration at the chiral center to provide the (R)-ester 9a. Saponification of the ester, followed by peptide coupling as before, provides the validated T3SS inhibitor compound 11a as a single enantiomer, designated MBX 1684, which is the R-isomer of MBX 1641.

Scheme 3

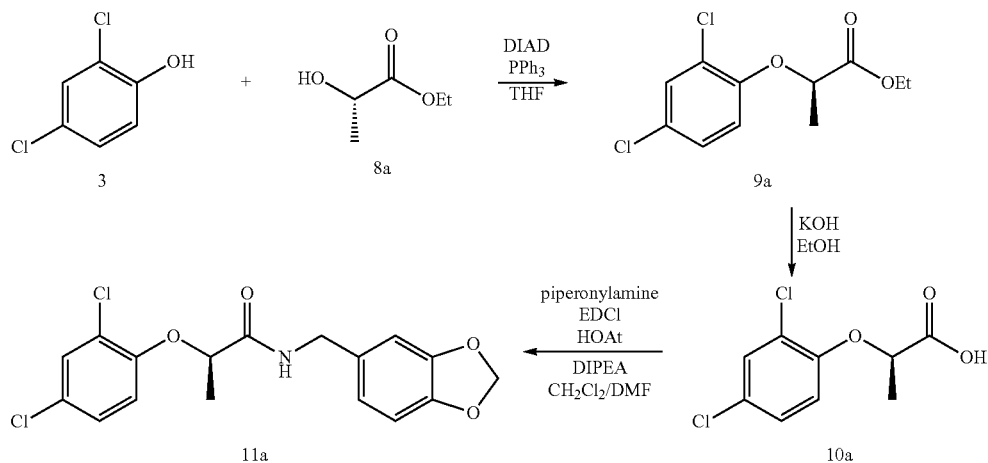

The other enantiomer (compound 11b, designated MBX 1686, which is the S-isomer of MBX 1686) is produced in the same way beginning from (R)-ethyl lactate (Scheme 4).

Scheme 4

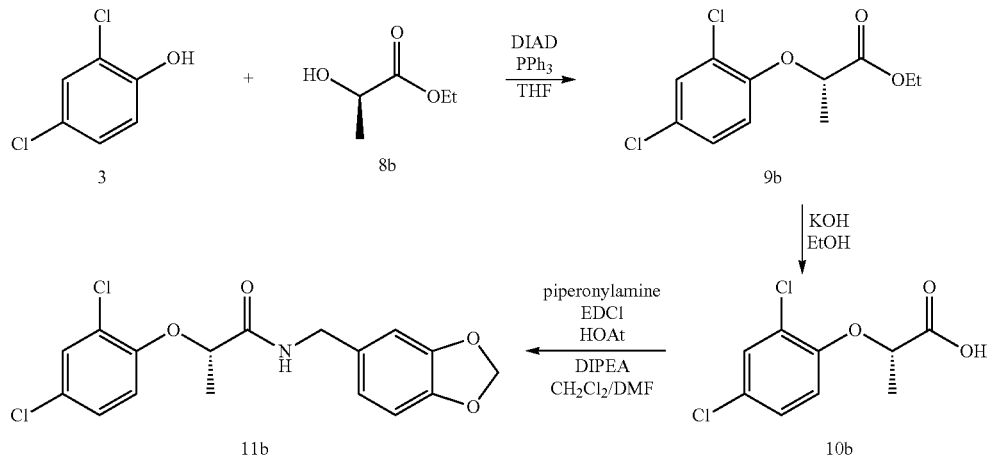

Synthetic Protocols According to the Above Synthetic Schemes

1. Synthesis of N-[3,4-(methylenedioxy)benzyl]-2-(2,4-dichlorophenoxy)acetamide (compound 2a in Scheme 1, designated MBX 1668, "des-methyl" analog of MBX 1641)

To a solution of 2-(2,4-dichlorophenoxy)acetic acid (1a; 1.0 g, 4.52 mmol), 1-hydroxy-7-azabenzotriazole (0.62 g, 5.0 mmol, 1.1 eq), and N-(3-dimethylaminopropyl)-N'-ethylcarbodiimide hydrochloride (0.87 g, 5.0 mmol, 1.1 eq) in dry DMF (25 mL) was added piperonylamine (0.81 mL, 6.5 mmol, 1.2 eq). The solution was stirred at room temperature for 30 minutes. Diisopropylethylamine (2.35 mL, 13.5 mmol, 3.0 eq.) was then added, and the solution was stirred at room temperature for 16 hour. The reaction was poured into water (250 mL) and refrigerated. The resulting precipitated solids were filtered, rinsed with water, and dried. The solid was then subjected to chromatography on silica gel with 15%-40% EtOAc/hexane. Product-containing fractions were pooled and evaporated to yield 0.84 g (53%) of compound 2a (MBX 1668) as a white powder: $R_f$ 0.38 (50% EtOA/hexanes); mp 117-119° C.; MS (ESI) m/z 353.9 [M+H]$^+$; $^1$H NMR (CDCl$_3$) δ 7.39-7.38 (d, 1H), 7.23-7.23 (dd, 1H), 7.00 (s, 1H), 6.85-6.82 (d, 1H), 6.78-6.76 (m, 3H), 5.95 (s, 2H), 4.55 (s, 2H), 4.65-4.45 (d, 2H).

2. Synthesis of N-[3,4-(methylenedioxy)benzyl]-2-(2,4-dichlorophenoxy)propanamide (compound 2b in Scheme 1, designated MBX 1641), a validated T3SS inhibitor To a solution of 2-(2,4-dichlorophenoxy)propionic acid (compound 1b; 1.275 g, 5.45 mmol), 1-hydroxy-7-azabenzotriazole (0.82 g, 6.0 mmol, 1.1 eq), and N-(3-dimethylaminopropyl)-N'-ethylcarbodiimide hydrochloride (1.15 g, 6.0 mmol, 1.1 eq) in dry DMF (25 mL) was added piperonylamine (0.81 mL, 6.5 mmol, 1.2 eq). The solution was stirred at room temperature for 30 minutes. Diisopropylethylamine (2.84 mL, 16.4 mmol, 3.0 eq.) was then added, and the solution was stirred at room temperature for 16 h. The reaction was poured into a mixture of 10% aq. citric acid (200 mL) and EtOAc (300 mL). The organic layer was washed with 10% aqueous citric acid, water, saturated aqueous NaHCO$_3$, water, then brine. The organic solution was then dried over Na$_2$SO$_4$, and concentrated on a rotary evaporator. The concentrated solution was triturated with hexanes (×3) to give a precipitate. The solid was collected by filtration to yield 1.84 g (92%) of compound 2b as a white powder: $R_f$ 0.52 (50% EtOAc/hexanes); mp 120-121° C.; MS (ESI) m/z 367.9 [M+H]$^+$; $^1$H NMR (CDCl$_3$) δ 7.38-7.37 (d, 1H), 7.20-7.17 (dd, 1H), 6.91 (s, 1H), 6.86-6.83 (d, 1H), 6.76-6.68 (m, 3H), 5.95 (s, 2H), 4.76-4.69 (q, 1H), 4.40-4.37 (m, 2H), 1.65-1.63 (d, 3H).

3. Synthesis of ethyl 2-(2,4-dichlorophenoxy)-2-methylpropionate (intermediate ester compound 5 in Scheme 2)

A suspension of ethyl 2-bromo-2-methylpropanoate (compound 4; 2.19 mL, 15.4 mmol), 2,4-dichlorophenol (compound 3, 3.0 g, 18.4 mmol, 1.2 eq), and K$_2$CO$_3$ (3.05 g, 22.1 mmol, 1.2 eq) in acetonitrile (25 mL) was refluxed for 16 hours. The suspension was filtered through Celite, and the solids rinsed with acetonitrile. The filtrate was evaporated to yield a thick, pale yellow oil which was used without further purification: $^1$H NMR (CDCl$_3$) δ 7.37 (d, 1H), 7.10 (dd, 1H), 6.86 (d, 1H), 4.25 (q, 2H), 1.60 (s, 6H), 1.27 (t, 3H).

3. Synthesis of 2-(2,4-dichlorophenoxy)-2-methylpropionic acid (compound 6 in Scheme 2)

To a solution of KOH (2.48 g, 44.2 mmol, 15 eq) in H$_2$O (12 mL) was added a solution of ethyl 2-(2,4-dichlorophenoxy)-2-methylpropionate (compound 5; 0.80 g, 2.89 mmol) in EtOH (12 mL). The solution was stirred at room temperature for 4 hours, then excess EtOH was removed under vacuum. The remaining aqueous solution was washed with EtOAc (10 mL), then acidified with concentrated aqueous HCl. The aqueous mixture was then extracted with EtOAc (10 mL), and the organic extract dried over Na$_2$SO$_4$, filtered, and evaporated to yield a thick, colorless oil which was used without further purification: $^1$H NMR (CDCl$_3$) δ 7.42-7.41 (d, 1H), 7.19-7.15 (dd, 1H), 7.04-7.01 (d, 1H), 1.64 (s, 6H).

4. Synthesis of N-[3,4-(methylenedioxy)benzyl]-2-(2,4-dichlorophenoxy)-2-methylpropanamide (compound 7 in Scheme 2, designated MBX 1685, "dimethyl" analog of MBX 1641)

To a solution of 2-(2,4-dichlorophenoxy)-2-methylpropionic acid (compound 6; 136 mg, 0.55 mmol), 1-hydroxy-7-azabenzotriazole (82 mg 0.60 mmol, 1.1 eq), and N-(3-dimethylaminopropyl)-N'-ethylcarbodiimide hydrochloride (115 mg, 0.60 mmol, 1.1 eq) in dry DMF (3 mL) was added piperonylamine (0.81 mL, 0.65 mmol, 1.2 eq). The solution was stirred at room temperature for 30 minutes. Diisopropylethylamine (0.28 mL, 16.4 mmol, 3.0 eq.) was then added, and the solution was stirred at room temperature for 16 hours. The reaction was poured into 10% aq. citric acid (20 mL) and extracted with EtOAc (30 mL×3). The combined organic extracts were dried over Na$_2$SO$_4$, and evaporated to provide a residue which was subjected to chromatography on silica gel with 20% EtOAc/hexane. The fractions were pooled and evaporated to yield 101 mg (48%) of compound 7 as an ivory-colored solid: $R_f$ 0.60 (50% EtOAc-Hexanes); mp 92-94° C.; MS (ESI) m/z 382.0 [M+H]$^+$; $^1$H NMR (CDCl$_3$) δ 7.38 (d, 1H), 7.26 (s, 1H), 7.13 (d, 1H), 6.94 (d, 1H), 6.76 (m, 3H), 5.95 (s, 2H), 4.41 (s, 2H), 1.57 (s, 6H).

5. Synthesis of ethyl (R)-2-(2,4-dichlorophenoxy)propionate (compound 9a in Scheme 3)

To a solution of 2,4-dichlorophenol (compound 3; 3.0 g, 18.4 mmol), ethyl (S)-lactate (compound 8a; 2.39 g, 20.2 mmol, 1.1 eq), and triphenylphosphine (7.23 g, 27.6 mmol, 1.5 eq) in anhydrous THF (50 mL), diisopropylazodicarboxylate (5.46 g, 27.6 mmol, 1.5 eq) was added dropwise. The reaction mixture was stirred 16 hours at room temperature. The solvent was evaporated and the resulting residue was subjected to chromatography on silica gel with 2-5% EtOAc/hexanes. Product-containing fractions were pooled and evaporated to yield a pale yellow oil which was used without further purification: $^1$H NMR (CDCl$_3$) δ 7.31 (d, 1H), 7.06 (dd, 1H), 6.75 (d, 1H), 4.70 (q, 1H), 4.21 (dq, 2H), 1.62 (d, 3H), 1.20 (t, 3H).

6. Synthesis of (R)-2-(2,4-dichlorophenoxy)propionic acid (compound 10a in Scheme 3)

To a solution of KOH (2.48 g, 44.2 mmol, 15 eq) in H$_2$O (12 mL) was added ethyl (R)-2-(2,4-dichlorophenoxy)propionate (compound 9a; 0.80 g, 3.05 mmol) in EtOH (12 mL) at room temperature. The solution was stirred for 4 hours, and then acidified with concentrated aqueous HCl (pH 3). The resulting solid was filtered, rinsed with water, and dried to yield a white powder which was used without further purification.

7. Synthesis of N-[3,4-(methylenedioxy)benzyl]-(R)-2-(2,4-dichlorophenoxy)propanamide (compound 11a in Scheme 3, a validated T3SS inhibitor, designated MBX 1684, which is the R-isomer of MBX 1641)

To a solution of (R)-2-(2,4-dichlorophenoxy)propionic acid (compound 10a; 128 mg, 0.55 mmol), 1-hydroxy-7-azabenzotriazole (82 mg, 0.60 mmol, 1.1 eq), and N-(3-dimethylaminopropyl)-N'-ethylcarbodiimide hydrochloride (115 mg, 0.60 mmol, 1.1 eq) in dry DMF (3 mL) was added piperonylamine (0.81 mL, 0.65 mmol, 1.2 eq). The solution was stirred at room temperature for 30 minutes. Diisopropylethylamine (0.28 mL, 1.7 mmol, 3.0 eq) was then added, and the solution was stirred at room temperature for 16 hours. The reaction was poured into 10% aqueous citric acid (20 mL) and extracted with EtOAc (30 mL×3). The combined organic extracts were dried over $Na_2SO_4$, and evaporated to provide a residue which was subjected to chromatography on silica gel with 20% EtOAc/hexane. The fractions were pooled and evaporated to yield 91 mg (45%) of compound 11a (designated MBX 1684) as a white solid: $R_f$ 0.52 (50% EtOAc-Hexanes); mp 136-138° C.; MS (ESI) m/z 368.0 [M+H]$^+$; $^1$H NMR (CDCl$_3$) δ 7.37 (d, 1H), 7.19 (dd, 1H), 6.91 (s, 1H), 6.85 (d, 1H), 6.76-6.68 (m, 3H), 5.95 (s, 2H), 4.73 (q, 1H), 4.39 (m, 2H), 1.64 (d, 3H).

8. Synthesis of N-[3,4-(methylenedioxy)benzyl]-(S)-2-(2,4-dichlorophenoxy)propanamide (compound 11b in Scheme 4, designated MBX-1686, which is the S-isomer of MBX 1641)

The synthesis of compound 11b was carried out in precisely the same manner as that of compound 11a, except ethyl (R)-lactate was used in the initial step of the sequence. The product was obtained as 98 mg (50%) of white powder: $R_f$ 0.52 (50% EtOAc-Hexanes); mp 140-142° C.; MS (ESI) m/z 367.9 [M+H]$^+$; $^1$H NMR (CDCl$_3$) δ 7.37 (d, 1H), 7.19 (dd, 1H), 6.91 (s, 1H), 6.85 (d, 1H), 6.76-6.68 (m, 3H), 5.95 (s, 2H), 4.73 (q, 1H), 4.39 (m, 2H), 1.64 (d, 3H).

Example 13

Synthesis of Morpholinone Compounds

This example provides a synthetic scheme for morpholinone compounds, such as the validated T3SS inhibitor compounds 3 and 4 in Table 3, above. The compound numbers in Scheme 5, below, are only relevant to the description of the specific synthetic scheme.

Synthetic Scheme 5

Morpholinone molecules of the general type 16 can be assembled beginning from the commercially available ethyl fumaryl chloride (12) and a commercially available or easily synthesized mono-alkylated ethanolamine. The resulting mono-amide 13 is then cyclized under the influence of base to provide the substituted morpholinone 14. This is then saponified to the corresponding acid and peptide coupling is used to introduce the amide functionality needed for the target molecule.

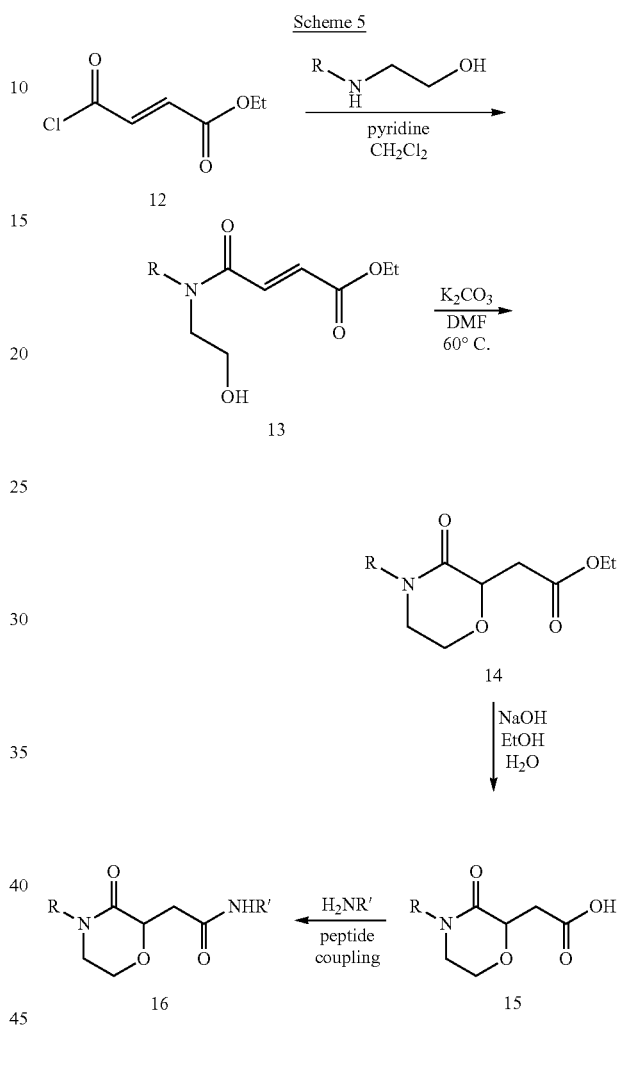

Scheme 5

Example 14

Synthesis of Fused Succinimide Compounds

This example provides a synthetic scheme for fused succinimide compounds, such as the validated T3SS inhibitor compounds 8 and 9 in Table 3, above. The compound numbers in Scheme 6, below, are only relevant to the description of the specific synthetic scheme.

Synthetic Scheme 6

Fused succinimide compounds of the general type 21 are synthesized from a fused succinic anhydride (20) that is made via the Diels-Alder cyclization of 2,5-dimethylfuran (17) and maleic anhydride (18). The intermediate 19 is reduced by hydrogenation to provide 20, which is then reacted with amines at high temperature to provide the target analogs 21.

Scheme 6

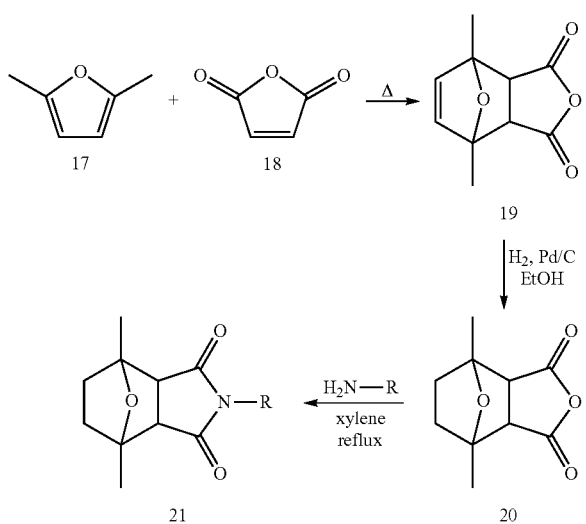

All publications, patent applications, patents, and other documents cited herein are incorporated by reference in their entirety. In case of conflict, the present specification, including definitions, will control. In addition, the materials, methods, and examples are illustrative only and not intended to be limiting.

Obvious variations to the disclosed compounds and alternative embodiments of the invention will be apparent to those skilled in the art in view of the foregoing disclosure. All such obvious variants and alternatives are considered to be within the scope of the invention as described herein.

REFERENCES CITED IN TEXT

1. Bradley, D. E. 1974. The adsorption of *Pseudomonas aeruginosa* pilus-dependent bacteriophages to a host mutant with nonretractile pili. Virology 58:149-63.
2. Carpino, L. A. 1993. 1-Hydroxy-7-azabenzotriazole. An Efficient Peptide Coupling Additive. J. Am. Chem. Soc. 115:4397-98.
3. Choi, K. H., A. Kumar, and H. P. Schweizer. 2006. A 10-min method for preparation of highly electrocompetent *Pseudomonas aeruginosa* cells: application for DNA fragment transfer between chromosomes and plasmid transformation. J Microbiol Methods 64:391-7.
4. Choi, K. H., and H. P. Schweizer. 2005. An improved method for rapid generation of unmarked *Pseudomonas aeruginosa* deletion mutants. BMC Microbiol 5:30.
5. Clatworthy, A. E., E. Pierson, and D. T. Hung. 2007. Targeting virulence: a new paradigm for antimicrobial therapy. Nat Chem Biol 3:541-8.
6. Cowell, B. A., D. Y. Chen, D. W. Frank, A. J. Vallis, and S. M. Fleiszig. 2000. ExoT of cytotoxic *Pseudomonas aeruginosa* prevents uptake by corneal epithelial cells. Infect Immun 68:403-6.
7. de Lorenzo, V., and K. N. Timmis. 1994. Analysis and construction of stable phenotypes in gram-negative bacteria with Tn5- and Tn10-derived minitransposons. Methods Enzymol 235:386-405.
8. Derouazi, M., B. Toussaint, L. Quenee, O. Epaulard, M. Guillaume, R. Marlu, and B. Polack. 2008. High-yield production of secreted active proteins by the *Pseudomonas aeruginosa* type III secretion system. Appl Environ Microbiol 74:3601-4.
9. Diaz, M. H., C. M. Shaver, J. D. King, S. Musunuri, J. A. Kazzaz, and A. R. Hauser. 2008. *Pseudomonas aeruginosa* induces localized immunosuppression during pneumonia. Infect Immun 76:4414-21.
10. El Solh, A. A., G. Choi, M. J. Schultz, L. A. Pineda, and C. Mankowski. 2007. Clinical and hemostatic responses to treatment in ventilator-associated pneumonia: role of bacterial pathogens. Crit. Care Med 35:490-6.
11. Engel, J., and P. Balachandran. 2009. Role of *Pseudomonas aeruginosa* type III effectors in disease. Curr Opin Microbiol 12:61-6.
12. Felise, H. B., H. V. Nguyen, R. A. Pfuetzner, K. C. Barry, S. R. Jackson, M. P. Blanc, P. A. Bronstein, T. Kline, and S. I. Miller. 2008. An inhibitor of gram-negative bacterial virulence protein secretion. Cell Host Microbe 4:325-36.
13. Franchi, L., T. Eigenbrod, R. Munoz-Planillo, and G. Nunez. 2009. The inflammasome: a caspase-1-activation platform that regulates immune responses and disease pathogenesis. Nat Immunol 10:241-7.
14. Frazzati-Gallina, N. M., R. L. Paoli, R. M. Mourao-Fuches, S. A. Jorge, and C. A. Pereira. 2001. Higher production of rabies virus in serum-free medium cell cultures on microcarriers. J Biotechnol 92:67-72.
15. Garrity-Ryan, L., B. Kazmierczak, R. Kowal, J. Comolli, A. Hauser, and J. N. Engel. 2000. The arginine finger domain of ExoT contributes to actin cytoskeleton disruption and inhibition of internalization of *Pseudomonas aeruginosa* by epithelial cells and macrophages. Infect Immun 68:7100-13.
16. Gauthier, A., M. L. Robertson, M. Lowden, J. A. Ibarra, J. L. Puente, and B. B. Finlay. 2005. Transcriptional inhibitor of virulence factors in enteropathogenic *Escherichia coli*. Antimicrob Agents Chemother 49:4101-9.
17. Goehring, U. M., G. Schmidt, K. J. Pederson, K. Aktories, and J. T. Barbieri. 1999. The N-terminal domain of *Pseudomonas aeruginosa* exoenzyme S is a GTPase-activating protein for Rho GTPases. J Biol Chem 274:36369-72.
18. Ha, U., and S. Jin. 2001. Growth phase-dependent invasion of *Pseudomonas aeruginosa* and its survival within HeLa cells. Infect Immun 69:4398-406.
19. Hauser, A. R. 2009. The type III secretion system of *Pseudomonas aeruginosa*: infection by injection. Nat Rev Microbiol 7:654-65.
20. Hoang, T. T., A. J. Kutchma, A. Becher, and H. P. Schweizer. 2000. Integration-proficient plasmids for *Pseudomonas aeruginosa*: site-specific integration and use for engineering of reporter and expression strains. Plasmid 43:59-72.
21. Holloway, B. W., V. Krishnapillai, and A. F. Morgan. 1979. Chromosomal genetics of *Pseudomonas*. Microbiol Rev 43:73-102.
22. Hudson, D. L., A. N. Layton, T. R. Field, A. J. Bowen, H. Wolf-Watz, M. Elofsson, M. P. Stevens, and E. E. Galyov. 2007. Inhibition of type III secretion in *Salmonella enterica* serovar Typhimurium by small-molecule inhibitors. Antimicrob Agents Chemother 51:2631-5.
23. Hueck, C. J. 1998. Type III protein secretion systems in bacterial pathogens of animals and plants. Microbiol. Mol Biol Rev 62:379-433.
24. Kauppi, A. M., R. Nordfelth, H. Uvell, H. Wolf-Watz, and M. Elofsson. 2003. Targeting bacterial virulence: inhibitors of type III secretion in *Yersinia*. Chem Biol 10:241-9.
25. Keyser, P., M. Elofsson, S. Rosell, and H. Wolf-Watz. 2008. Virulence blockers as alternatives to antibiotics: type III secretion inhibitors against Gram-negative bacteria. J Intern Med 264:17-29.

26. Kumar, A., K. L. Chua, and H. P. Schweizer. 2006. Method for regulated expression of single-copy efflux pump genes in a surrogate *Pseudomonas aeruginosa* strain: identification of the BpeEF-OprC chloramphenicol and trimethoprim efflux pump of *Burkholderia* pseudomallei 1026b. Antimicrob Agents Chemother 50:3460-3.

27. Lee, V. T., S. Pukatzki, H. Sato, E. Kikawada, A. A. Kazimirova, J. Huang, X. L1, J. P. Arm, D. W. Frank, and S. Lory. 2007. Pseudolipasin A is a specific inhibitor for phospholipase A2 activity of *Pseudomonas aeruginosa* cytotoxin ExoU. Infect Immun 75:1089-98.

28. Lee, V. T., R. S. Smith, B. Tummler, and S. Lory. 2005. Activities of *Pseudomonas aeruginosa* effectors secreted by the Type III secretion system in vitro and during infection. Infect Immun 73:1695-705.

29. Liberati, N. T., J. M. Urbach, S. Miyata, D. G. Lee, E. Drenkard, G. Wu, J. Villanueva, T. Wei, and F. M. Ausubel. 2006. An ordered, nonredundant library of *Pseudomonas aeruginosa* strain PA14 transposon insertion mutants. Proc Natl Acad Sci USA 103:2833-8.

30. Lomovskaya, O., M. S. Warren, A. Lee, J. Galazzo, R. Fronko, M. Lee, J. Blais, D. Cho, S. Chamberland, T. Renau, R. Leger, S. Hecker, W. Watkins, K. Hoshino, H. Ishida, and V. J. Lee. 2001. Identification and characterization of inhibitors of multidrug resistance efflux pumps in *Pseudomonas aeruginosa*: novel agents for combination therapy. Antimicrob Agents Chemother 45:105-16.

31. Marketon, M. M., R. W. DePaolo, K. L. DeBord, B. Jabri, and O, Schneewind. 2005. Plague bacteria target immune cells during infection. Science 309:1739-41.

32. Marshall, N. J., C. J. Goodwin, and S. J. Holt. 1995. A critical assessment of the use of microculture tetrazolium assays to measure cell growth and function. Growth Regul 5:69-84.

33. Miao, E. A., R. K. Ernst, M. Dors, D. P. Mao, and A. Aderem. 2008. *Pseudomonas aeruginosa* activates caspase 1 through Ipaf. Proc Natl Acad Sci USA 105:2562-7.

34. Mitsunobu, 0.1981. The use of diethyl azodicarboxylate and triphenylphosphine in synthesis and transformation of natural products. Synthesis 1981:1-28.

35. Moir, D. T., M. Di, R. A. Moore, H. P. Schweizer, and D. E. Woods. 2008. Cellular reporter screens for inhibitors of *Burkholderia* pseudomallei targets in *Pseudomonas aeruginosa*. Trans R Soc Trop Med Hyg 102 Suppl 1:S152-62.

36. Moir, D. T., M. Di, T. Opperman, H. P. Schweizer, and T. L. Bowlin. 2007. A high-throughput, homogeneous, bioluminescent assay for *Pseudomonas aeruginosa* gyrase inhibitors and other DNA-damaging agents. J Biomol Screen 12:855-64.

37. Moore, R. A., S. Reckseidler-Zenteno, H. Kim, W. Nierman, Y. Yu, A. Tuanyok, J. Warawa, D. DeShazer, and D. E. Woods. 2004. Contribution of gene loss to the pathogenic evolution of *Burkholderia pseudomallei* and *Burkholderia mallei*. Infect Immun 72:4172-87.

38. Muschiol, S., L. Bailey, A. Gylfe, C. Sundin, K. Hultenby, S. Bergstrom, M. Elofsson, H. Wolf-Watz, S, Normark, and B. Henriques-Normark. 2006. A small-molecule inhibitor of type III secretion inhibits different stages of the infectious cycle of *Chlamydia trachomatis*. Proc Natl Acad Sci USA 103:14566-71.

39. NCCLS. 1997. Approved standard M7-A4. Methods for dilution antimicrobial susceptibility tests for bacteria that grow aerobically, 4th ed. National Committee for Clinical Laboratory Standards, Wayne, Pa.

40. Negrea, A., E. Bjur, S. E. Ygberg, M. Elofsson, H. Wolf-Watz, and M. Rhen. 2007. Salicylidene acylhydrazides that affect type III protein secretion in *Salmonella enterica* serovar typhimurium. Antimicrob Agents Chemother 51:2867-76.

41. Nordfelth, R., A. M. Kauppi, H. A. Norberg, H. Wolf-Watz, and M. Elofsson. 2005. Small-molecule inhibitors specifically targeting type III secretion. Infect Immun 73:3104-14.

42. Ohman, D. E., S. J. Cryz, and B. H. Iglewski. 1980. Isolation and characterization of *Pseudomonas aeruginosa* PAO mutant that produces altered elastase. J Bacteriol 142:836-42.

43. Pallen, M. J., S. A. Beatson, and C. M. Bailey. 2005. Bioinformatics, genomics and evolution of non-flagellar type-III secretion systems: a Darwinian perspective. FEMS Microbiol Rev 29:201-29.

44. Pan, N.J., M. J. Brady, J. M. Leong, and J. D. Goguen. 2009. Targeting type III secretion in *Yersinia pestis*. Antimicrob Agents Chemother 53:385-92.

45. Rahme, L. G., E. J. Stevens, S. F. Wolfort, J. Shao, R. G. Tompkins, and F. M. Ausubel. 1995. Common virulence factors for bacterial pathogenicity in plants and animals. Science 268:1899-902.

46. Rello, J., D. Mariscal, F. March, P. Jubert, F. Sanchez, J. Valles, and P. Coll. 1998. Recurrent *Pseudomonas aeruginosa* pneumonia in ventilated patients: relapse or reinfection? Am J Respir Crit. Care Med 157:912-6.

47. Rietsch, A., I. Vallet-Gely, S. L. Dove, and J. J. Mekalanos. 2005. ExsE, a secreted regulator of type III secretion genes in *Pseudomonas aeruginosa*. Proc Natl Acad Sci USA 102:8006-11.

48. Roy-Burman, A., R. H. Savel, S. Racine, B. L. Swanson, N. S. Revadigar, J. Fujimoto, T. Sawa, D. W. Frank, and J. P. Wiener-Kronish. 2001. Type III protein secretion is associated with death in lower respiratory and systemic *Pseudomonas aeruginosa* infections. J Infect Dis 183:1767-74.

49. Schulert, G. S., H. Feltman, S. D. Rabin, C. G. Martin, S. E. Battle, J. Rello, and A. R. Hauser. 2003. Secretion of the toxin ExoU is a marker for highly virulent *Pseudomonas aeruginosa* isolates obtained from patients with hospital-acquired pneumonia. J Infect Dis 188:1695-706.

50. Shaver, C. M., and A. R. Hauser. 2006. Interactions between effector proteins of the *Pseudomonas aeruginosa* type III secretion system do not significantly affect several measures of disease severity in mammals. Microbiology 152:143-52.

51. Shaver, C. M., and A. R. Hauser. 2004. Relative contributions of *Pseudomonas aeruginosa* ExoU, ExoS, and ExoT to virulence in the lung. Infect Immun 72:6969-77.

52. Silver, D. R., I. L. Cohen, and P. F. Weinberg. 1992. Recurrent *Pseudomonas aeruginosa* pneumonia in an intensive care unit. Chest 101:194-8.

53. Stover, C. K., X. Q. Pham, A. L. Erwin, S. D. Mizoguchi, P. Warrener, M. J. Hickey, F. S. Brinkman, W. O. Hufnagle, D. J. Kowalik, M. Lagrou, R. L. Garber, L. Goltry, E. Tolentino, S. Westbrock-Wadman, Y. Yuan, L. L. Brody, S, N. Coulter, K. R. Folger, A. Kas, K. Larbig, R. Lim, K. Smith, D. Spencer, G. K. Wong, Z. Wu, I. T. Paulsen, J. Reizer, M. H. Saier, R. E. Hancock, S. Lory, and M. V. Olson. 2000. Complete genome sequence of *Pseudomonas aeruginosa* PA01, an opportunistic pathogen. Nature 406:959-64.

54. Urbanowski, M. L., G. L. Lykken, and T. L. Yahr. 2005. A secreted regulatory protein couples transcription to the secretory activity of the *Pseudomonas aeruginosa* type III secretion system. Proc Natl Acad Sci USA 102:9930-5.
55. Vallis, A. J., T. L. Yahr, J. T. Barbieri, and D. W. Frank. 1999. Regulation of ExoS production and secretion by *Pseudomonas aeruginosa* in response to tissue culture conditions. Infect Immun 67:914-20.
56. Vance, R. E., A. Rietsch, and J. J. Mekalanos. 2005. Role of the type III secreted exoenzymes S, T, and Y in systemic spread of *Pseudomonas aeruginosa* PA01 in vivo. Infect Immun 73:1706-13.
57. Veenendaal, A. K., C. Sundin, and A. J. Blocker. 2009. Small-molecule type III secretion system inhibitors block assembly of the *Shigella* type III secreton. J Bacteriol 191:563-70.
58. Veesenmeyer, J. L., A. R. Hauser, T. Lisboa, and J. Rello. 2009. *Pseudomonas aeruginosa* virulence and therapy: evolving translational strategies. Crit. Care Med 37:1777-86.
59. Wolf, K., H. J. Betts, B. Chellas-Gery, S. Hower, C. N. Linton, and K. A. Fields. 2006. Treatment of *Chlamydia trachomatis* with a small molecule inhibitor of the *Yersinia* type III secretion system disrupts progression of the chlamydial developmental cycle. Mol Microbiol 61:1543-55.
60. Zhang, J. H., T. D. Chung, and K. R. Oldenburg. 1999. A Simple Statistical Parameter for Use in Evaluation and Validation of High Throughput Screening Assays. J Biomol Screen 4:67-73.
61. Miret, S., de Groene, E. M., and Klaffke, W. 2006. Comparison of In Vitro Assays of Cellular Toxicity in the Human Hepatic Cell Line HepG2. J Biomol Screen 11(2):184-193.
62. Peternel, L., Kotnik, M., Rezelj, A., and Urleb, U. 2009. Comparison of 3 Cytotoxicity Screening Assays and Their Application to the Selection of Novel Antibacterial Hits. J Biomol Screen 14(2):142-150.

The invention claimed is:

1. A method for treating an individual infected with a Gram-negative bacterium comprising administering to said individual an effective amount to inhibit T3SS-mediated effector secretion of a compound selected from the group consisting of:

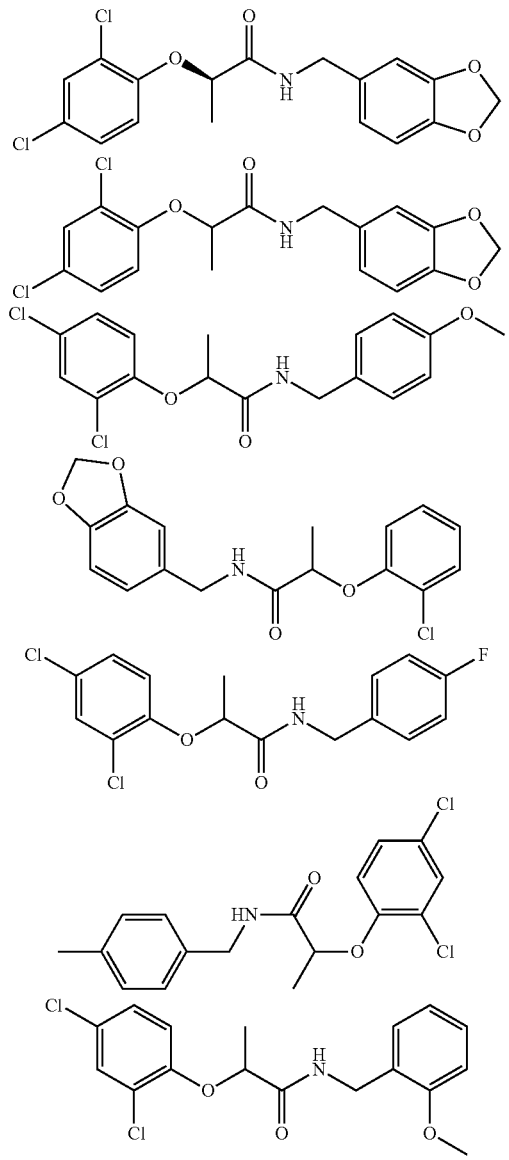

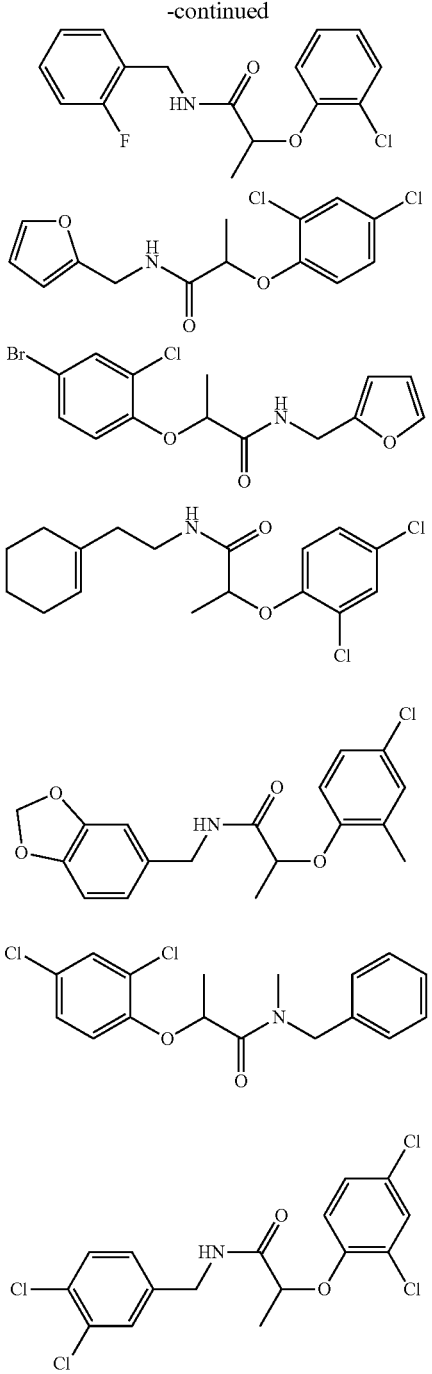

-continued

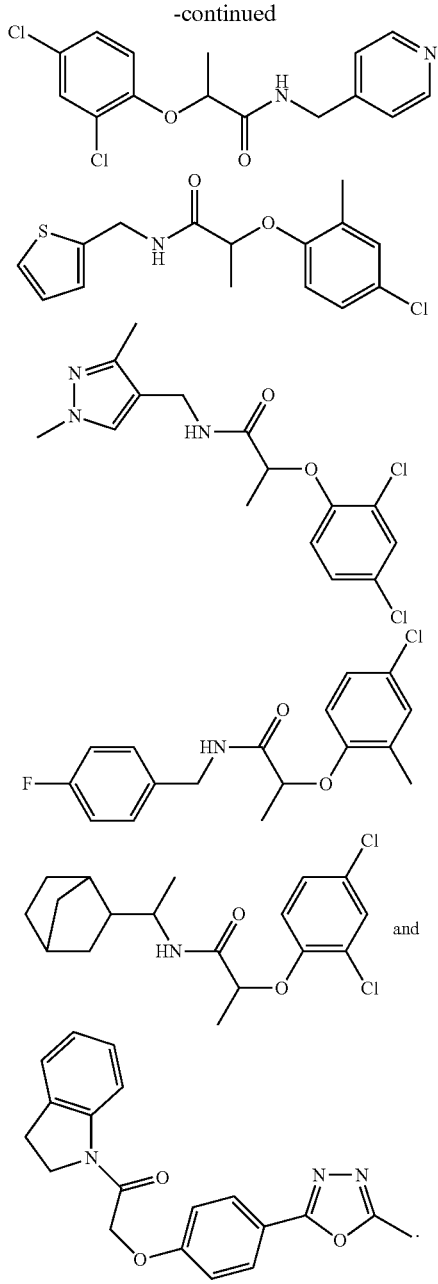

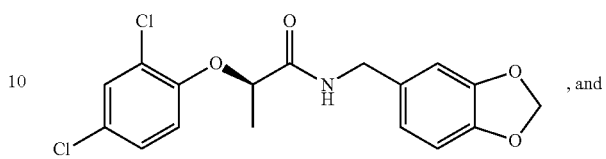

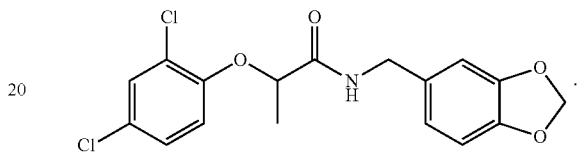

2. The method of claim 1, wherein said compound is selected from the group consisting of:

, and

.

3. The method according to claim 1, wherein said individual is human.

4. The method according to claim 1, wherein said Gram-negative bacterium is of the genus *Pseudomonas, Salmonella, Yersinia,* or *Chlamydia.*

5. The method according to claim 1, wherein said Gram-negative bacterium is *Pseudomonas aeruginosa, Yersinia pestis* or *Chlamydia trachomatis.*

6. The method according to claim 1, wherein said Gram-negative bacterium is *Pseudomonas aeruginosa.*

7. The method according to claim 1, further comprising administering an additional active ingredient selected from the group consisting of an antibiotic, an antibody, an antiviral agent, an anticancer agent, an analgesic, an immunostimulatory agent, a natural, synthetic or semi-synthetic hormone, a central nervous system stimulant, an antiemetic agent, an anti-histamine, an erythropoietin, a complement stimulating agent, a sedative, a muscle relaxant agent, an anesthetic agent, an anticonvulsive agent, an antidepressant, an antipsychotic agent, and combinations thereof.

* * * * *

```
                         SEQUENCE LISTING

<160> NUMBER OF SEQ ID NOS: 12

<210> SEQ ID NO 1
<211> LENGTH: 29
<212> TYPE: DNA
<213> ORGANISM: Artificial Sequence
<220> FEATURE:
<223> OTHER INFORMATION: PCR primer exoT-F+EcoRI

<400> SEQUENCE: 1
tactacgaat tcccaggaag caccgaagg                                         29

<210> SEQ ID NO 2
<211> LENGTH: 32
<212> TYPE: DNA
<213> ORGANISM: Artificial Sequence
<220> FEATURE:
<223> OTHER INFORMATION: PCR primer exoT-R+EcoRI

<400> SEQUENCE: 2
cattacgaat tcctggtact cgccgttggt at                                     32

<210> SEQ ID NO 3
<211> LENGTH: 20
<212> TYPE: DNA
<213> ORGANISM: Artificial Sequence
<220> FEATURE:
<223> OTHER INFORMATION: PCR primer exoT-out-F

<400> SEQUENCE: 3
tagggaaagt ccgctgtttt                                                   20

<210> SEQ ID NO 4
<211> LENGTH: 20
<212> TYPE: DNA
<213> ORGANISM: Artificial Sequence
<220> FEATURE:
<223> OTHER INFORMATION: PCR primer luxC-R

<400> SEQUENCE: 4
cctgaggtag ccattcatcc                                                   20

<210> SEQ ID NO 5
<211> LENGTH: 48
<212> TYPE: DNA
<213> ORGANISM: Artificial Sequence
<220> FEATURE:
```

<223> OTHER INFORMATION: PCR primer exoS-F+GWL

<400> SEQUENCE: 5
tacaaaaaag caggctagga acagacatg catattcaat cgcttcag         48

<210> SEQ ID NO 6
<211> LENGTH: 51
<212> TYPE: DNA
<213> ORGANISM: Artificial Sequence
<220> FEATURE:
<223> OTHER INFORMATION: PCR primer exoS(234)-R

<400> SEQUENCE: 6 atctttact ttcaccagcg tttctgggtg accgtcggcc gatactctgc t      51

<210> SEQ ID NO 7
<211> LENGTH: 20
<212> TYPE: DNA
<213> ORGANISM: Artificial Sequence
<220> FEATURE:
<223> OTHER INFORMATION: PCR primer BLA-F

<400> SEQUENCE: 7
cacccagaaa cgctggtgaa                                        20

<210> SEQ ID NO 8
<211> LENGTH: 38
<212> TYPE: DNA
<213> ORGANISM: Artificial Sequence
<220> FEATURE:
<223> OTHER INFORMATION: PCR primer BLA-R+GWR

<400> SEQUENCE: 8
tacaagaaag ctgggtttgg tctgacagtt accaatgc                    38

<210> SEQ ID NO 9
<211> LENGTH: 29
<212> TYPE: DNA
<213> ORGANISM: Artificial Sequence
<220> FEATURE:
<223> OTHER INFORMATION: PCR primer GW-attB1

<400> SEQUENCE: 9
ggggacaagt ttgtacaaaa aagcaggct                              29

<210> SEQ ID NO 10
<211> LENGTH: 29
<212> TYPE: DNA
<213> ORGANISM: Artificial Sequence
<220> FEATURE:
<223> OTHER INFORMATION: PCR primer GW-attB2

<400> SEQUENCE: 10
ggggaccact ttgtacaaga aagctgggt                              29

<210> SEQ ID NO 11
<211> LENGTH: 72
<212> TYPE: DNA
<213> ORGANISM: Artificial Sequence
<220> FEATURE:
<223> OTHER INFORMATION: PCR primer lux-F+GWL

<400> SEQUENCE: 11
tacaaaaaag caggctagga acagctatg acgaagaaga tcagttttat aattaacggc    60
caggttgaaa tc                                                       72

```
<210> SEQ ID NO 12
<211> LENGTH: 36
<212> TYPE: DNA
<213> ORGANISM: Artificial Sequence
<220> FEATURE:
<223> OTHER INFORMATION: PCR primer lux-R+GWR

<400> SEQUENCE: 12
tacaagaaag ctgggtgttt tcccagtcac gacgtt                    36
```